US009522908B2

(12) United States Patent
Brown et al.

(10) Patent No.: US 9,522,908 B2
(45) Date of Patent: Dec. 20, 2016

(54) EZRIN INHIBITORS AND METHODS OF MAKING AND USING

(71) Applicant: Georgetown University, Washington, DC (US)

(72) Inventors: Milton L. Brown, Brookeville, MD (US); Mikell Paige, Fairfax, VA (US); Jeffrey A. Torestsky, Silver Spring, MD (US); Aykut Uren, Rockville, MD (US); George Kosturko, Alexandria, VA (US); Gullay Bulut, Washington, DC (US)

(73) Assignee: Gerogetown University, Washington, DC (US)

( * ) Notice: Subject to any disclaimer, the term of this patent is extended or adjusted under 35 U.S.C. 154(b) by 0 days.

(21) Appl. No.: 14/047,362

(22) Filed: Oct. 7, 2013

(65) Prior Publication Data

US 2014/0135325 A1    May 15, 2014

Related U.S. Application Data

(63) Continuation of application No. 13/818,223, filed as application No. PCT/US2011/048635 on Aug. 22, 2011, now abandoned.

(60) Provisional application No. 61/375,823, filed on Aug. 21, 2010.

(51) Int. Cl.
| | | |
|---|---|---|
| *C07D 215/38* | (2006.01) |
| *A61K 31/535* | (2006.01) |
| *A61K 31/47* | (2006.01) |
| *C07D 413/12* | (2006.01) |
| *C07D 209/48* | (2006.01) |
| *C07D 215/24* | (2006.01) |
| *C07D 217/24* | (2006.01) |
| *C07D 401/12* | (2006.01) |
| *C07D 471/04* | (2006.01) |
| *C07D 237/30* | (2006.01) |
| *C07D 401/06* | (2006.01) |

(52) U.S. Cl.
CPC .......... *C07D 413/12* (2013.01); *C07D 209/48* (2013.01); *C07D 215/24* (2013.01); *C07D 215/38* (2013.01); *C07D 217/24* (2013.01); *C07D 237/30* (2013.01); *C07D 401/06* (2013.01); *C07D 401/12* (2013.01); *C07D 471/04* (2013.01)

(58) Field of Classification Search
None
See application file for complete search history.

(56) References Cited

U.S. PATENT DOCUMENTS 5,283,336 A    2/1994    Field et al.

FOREIGN PATENT DOCUMENTS

WO    2004/026305    4/2004

OTHER PUBLICATIONS

Greenwald, RB. et al. Drug Delivery Systems: Water Soluble Taxol 2'-Poly(ethylene glycol) Ester Prodrugs-Design and in Vivo Effectiveness. J. Med. Chem. 1996, vol. 39, p. 425.*
Testa, B. et al. Lessons Learned from Marketed and Investigational Prodrugs. J. Med. Chem. 2004, vol. 47(10), p. 2393.*
Lazo, JS. et al. Discovery and Biological Evaluation of a New Family of Potent Inhibitors of the Dual Specificity Protein Phosphatase Cdc25. Journal of Medicinal Chemistry. 2001, vol. 44, p. 4043, table 1, 663284, 677948, p. 4044.*
Folkers, K. et al. Synthesis of New Alkylamino- and Alkylaminomethyl-5,8-quinolinequinones as Inhibitors of Coenzyme Q and as Antimalarials. Journal of Medicinal Chemistry. 1972, vol. 15, p. 34.*
Kita, Y. et al. Total Synthesis of Discorhabdin C: A General Aza Spiro Dienone Formation from O-Silylated Phenol Derivatives Using a Hypervalent Iodine Reagent. Journal of American Chemical Society. 1992, vol. 114, p. 2176.*
Lazo, JS. et al. Discovery and Biological Evaluation of a New Family of Potent Inhibitors of the Dual Specificity Protein Phosphatase Cdc25. Journal of Medicinal Chemistry. 2001, vol. 44, p. 4043.*
Kita, Y. et al. An Intramolecular Cyclization of Phenol Derivatives Bearing Aminoquinones Using a Hypervalent Iodine Reagent. J. Org. Chem. 1996, vol. 61, p. 224.*
Lazo, JS. et al. Redox Regulation of Cdc25B by Cell-Active Quinolinediones. Molecular Pharmacology. 2005, vol. 68, p. 1813.*
Chen et al., "Wnt10b induces chemotaxis of osteosarcoma and correlates with reduced survival," Pediatr. Blood Cancer, 51(3): 349-355 (2008).
Dunn et al., "Metastatic osteosarcoma to lung: a clinicopathologic study of surgical biopsies and resections," Cancer, 40: 3054-3064 (1977).
Fivash et al., "BIAcore for macromolecular interaction," Curr. Opin. Biotechnol, 9(1): 97-101 (1998).
Flaugh et al., "Synthesis and evaluation of the antiovulatory activity of a variety of melatonin analogs," J. Med. Chem., 22(1): 63-69 (1979).
Gautreau et al., "Morphogenic effects of ezrin require a phosphorylation-induced transition from oligomers to monomers at the plasma membrane," J. Cell Biol., 150(1): 193-203 (2000).
Gomtsyan et al., "Novel Transient Receptor Potential Vanilloid 1 Receptor Antagonists for the Treatment of Pain: Structure—Activity Relationships for Ureas with Quinoline, Isoquinoline, Quinazoline, Phthalazine, Quinoxaline, and Cinnoline Moieties," J. Med. Chem., 48(3): 744-752 (2005).

(Continued)

Primary Examiner — Rita Desai
Assistant Examiner — Ben S Michelson
(74) Attorney, Agent, or Firm — Morgan, Lewis & Bockius LLP

(57) ABSTRACT

The invention encompasses compound and pharmaceutical composition comprising the compound of the following Formula (I): or pharmaceutically acceptable salts or prodrugs thereof, that are useful for inhibiting ezrin protein in a cell or for inhibiting the growth of a cancer cell.

10 Claims, 20 Drawing Sheets

(56) References Cited

OTHER PUBLICATIONS

Hayakawa et al., "Regioselective electrophilic fluorination of indoles: syntheses of 4-fluoroserotonin and 4-fluoromelatonin," J. Fluorine Chemistry, 97(1-2): 161-164 (1999).

Khanna et al., "Metastasis-associated differences in gene expression in a murine model of osteosarcoma," Cancer Res., 61(9): 3750-3759 (2001).

Kharasch et al., "The conversion of quaternary pyrrolidinium salts to open-chain diamines," J. Organic Chemistry, 9: 359-372 (1944).

Kimmel et al., "Stages of embryonic development of the zebrafish," Dev. Dyn., 203(3): 253-310 (1995).

Kita et al., "An Intramolecular Cyclization of Phenol Derivatives Bearing Aminoquinones Using a Hypervalent Iodine Reagent," J. Org. Chem. 61(1): 223-227 (1996).

Link et al., "Identification of regulators of germ layer morphogenesis using proteomics in zebrafish ," J. Cell Sci., 119: 2073-2083 (2006).

Malmqvist, ",BIACORE: an affinity biosensor system for characterization of biomolecular interactions" Biochem Soc Trans., 27(2): 335-340 (1999).

Matsui et al., "Rho-kinase phosphorylates COOH-terminal threonines of ezrin/radixinlmoesin (ERM) proteins and regulates their head-to-tail association," J. Cell Biol, 140(3): 647-657 (1998).

Mendoza et al., "Modeling metastasis biology and therapy in real time in the mouse lung," J. Clin. Invest., 120(8): 2979-2988 (2010).

Norman et al., "Novel Vanilloid Receptor-1 Antagonists: 1. Conformationally Restricted Analogues of trans-Cinnamides," J. Med. Chem., 50 (15): 3497-3514 (2007).

NSC305787, Compound Summary for: CID 5458659, PubChem Compound Database (Feb. 27, 2006).

NSC668394, Compound Summary for: CID 381594, PubChem Compound Database (Mar. 26, 2005).

Reczek et al., "Identification of EBP50: A PDZ-containing Phosphoprotein that Associates with Members of the Ezrin-Radixin-Moesin Family," J. Cell Biol, 139(1): 169-179 (1997).

Ren et al., "The actin-cytoskeleton linker protein ezrin is regulated during osteosarcoma metastasis by PKC," Oncogene, 28(6): 792-802 (2009).

Ryu et al., "Synthesis and antifungal activity of 6-arylamino-phthalazine-5,8-diones and 6,7-bis(arylthio)- phthalazine-5,8-diones," Bioorganic and Medical Chemistry Letters, 17(9): 2577-2580 (2007).

Shanab et al., "Synthesis and biological evaluation of novel cytotoxic azanaphthoquinone annelated pyrrolo oximes," Bioorganic & Medicinal Chemistry Letters, 17(22): 6091-6095 (2007).

International search Report and Written Opinion issued in the corresponding PCT Application No. PCT/US2011/048635, mailed Jul. 6, 2012.

International Preliminary Report on Patentability issued in the corresponding PCT Application No. PCT/US2011/048635, dated Feb. 26, 2013.

\* cited by examiner

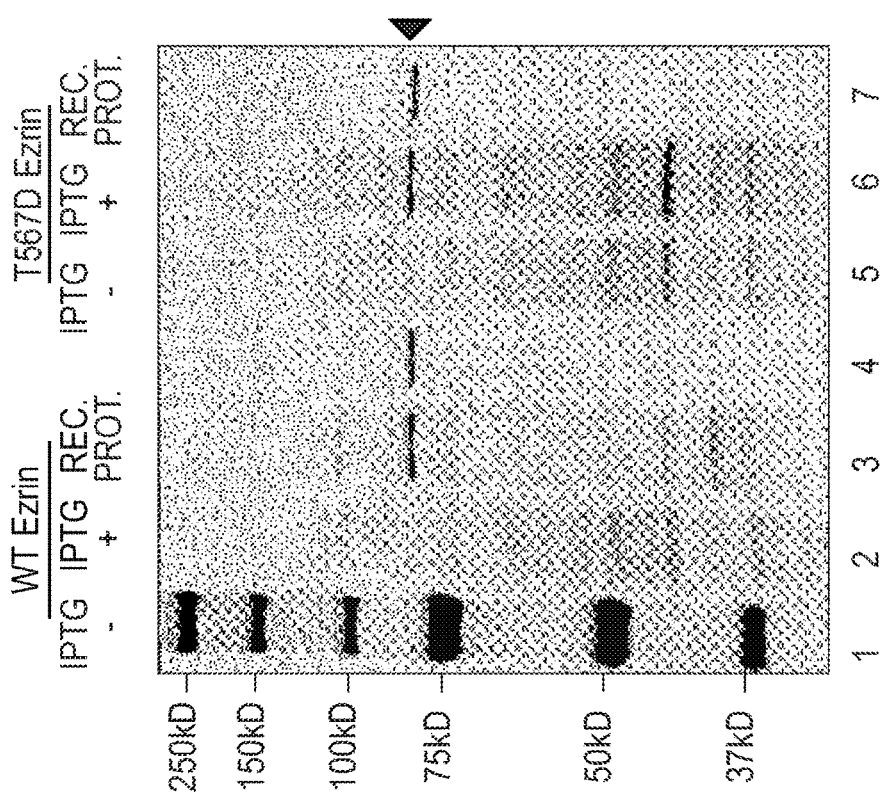
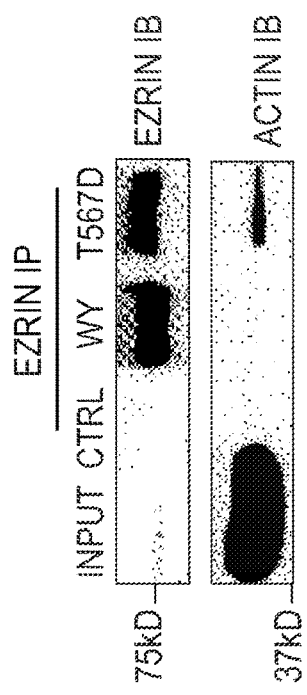
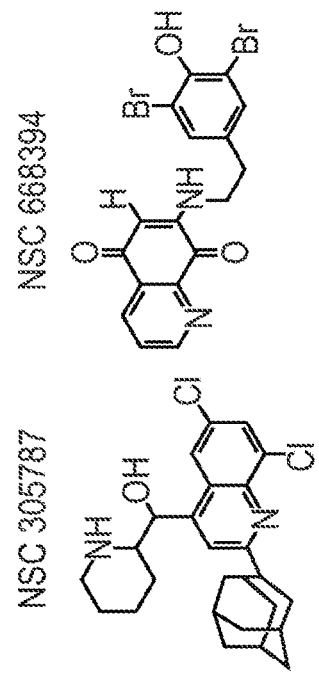
FIG. 1A
FIG. 1B
FIG. 1C

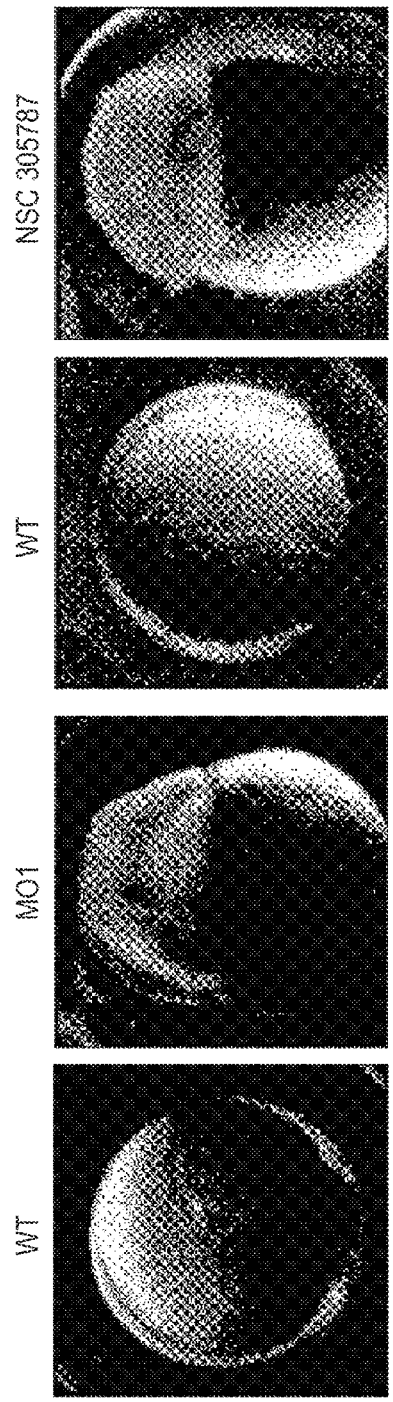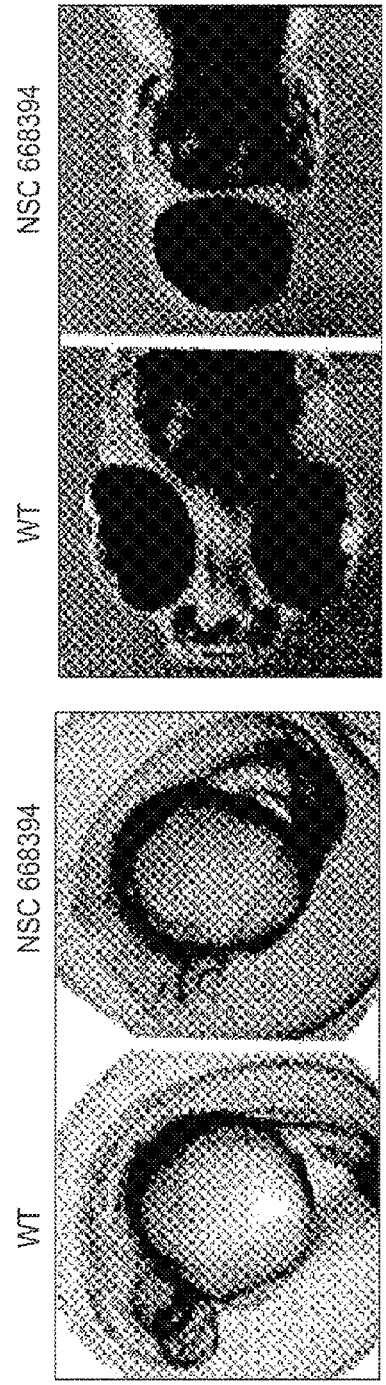

STRUCTURE CLASS: QUINOLINE-DIONE

| COMPOUND | R1 | R2 | R3 | KD (µM) | K7M2 IC$_{50}$ (µM) | K12 IC$_{50}$ (µM) |
|---|---|---|---|---|---|---|
| NSC 668394 | Br | OH | Br | 12.6 ± 6.3 | 5.9 ± 1.0 (P#19: 5-4-11) | 14.9 ± 2.2 (P#27: 05/10/11) |
| GK2-013 | H | H | H | NB | 5.87 ± 0.7 (P#15: 5-26-11) | 14.9 ± 0.5 (P#23: 05/26/11) |
| GK2-037 | Cl | H | H | NB | ND | |
| GK2-047 | Br | H | H | 9.1 | ND | 2.8 ± 0.3 (P#23: 07/11/11) |
| GK2-057 | Cl | OCH$_3$ | H | 7.0 ± 3.4 | 4.9 ± 1.3 (P#17: 7-10-11) | |
| GK2-025 | Br | OCH$_3$ | H | 309 (ST.STATE) | 6.8 ± 1.0 (P#15: 5-26-11) | 10.9 ± 0.8 (P#23: 05/26/11) |
| GK2-075 | H | OH | H | 6.2 | 10.2 ± 1.0 (P#17: 7-10-11) | 9.2 ± 0.5 (P#24: 07/15/11) |
| GK2-059 | OH | OH | H | 7.9 ± 1.8 | 14.8 ± 0.5 (P#20: 6-23-11) | 14.2 ± 0.4 (P#24: 06-23-11) |
| GK2-139 | OH | OH | OH | Agg | >50 | >75 |
| GK2-053 | OCH$_3$ | OCH$_3$ | H | NB | 10 | |
| GK3-129 | OBn | OBn | H | Agg | 3.9 ± 0.7 (P#18: 6-21-11) | 7.7 ± 1.5 (P#23: 6-21-11) |
| GK3-015 | Cl | OH | Cl | 8.0 ± 2.2 | 11.8 ± 0.5 (P#19: 5-4-11) | 13.0 ± 0.9 (P#27: 05/10/11) |
| GK3-189 | F | OH | F | 49.9 ± 12.2 | 12.7 ± 2.2 (P#19: 5-4-11) | 17.7 ± 0.2 (P#22: 05-24-11)* |
| GK3-209 | CH$_3$ | OH | CH$_3$ | 5.0 ± 0.6 | 6.5 ± 1.2 (P#20: 5-10-11) | 13.1 ± 0.2 (P#22: 05-24-11)* |

STRUCTURE CLASS: (1)NAPHTHYL-QUINONE, (2)ISOQUINOLINE-DIONE, (3)PHTHALAZINE-DIONE, (4)PHTHALIMIDE

| COMPOUND | R1 | R2 | R3 | KD (µM) | K7M2 IC$_{50}$ (µM) | K12 IC$_{50}$ (µM) |
|---|---|---|---|---|---|---|
| GK2-237-CLASS1 | Br | OH | Br | Agg | >50 (P#21: 06-09-11) | >75 (P#29: 06-09-11) |
| GK2-115-CLASS2 | Br | OH | Br | 40.1 ± 16.3 | 7.7 ± 1.1 (P#16: 6-17-11) | 12.0 ± 0.9 (P#21: 06-17-11) |
| GK2-135-CLASS3 | Br | OH | Br | Agg | 4.0 ± 0.1 (P#14: 7-7-11) | 4.1 ± 0.4 (P#21: 7-7-11) |
| GK2-185-CLASS3 | Cl | OH | Cl | Agg | | |
| GK2-201-CLASS3 | F | OH | F | NB | | |
| GK2-141-CLASS3 | OH | OH | H | 30.3 | 13.8 ± 0.6 (P#18: 6-3-11) | 2.5 ± 0.1 (P#26: 6-3-11) |
| GK2-103-CLASS3 | Br | OH | Br | NB | >50 (P#26: 05-16-11) | >75 (P#30: 05-16-11) |
| GK2-103-CLASS4 | OH | OH | H | NB | >50 (P#26: 05-16-11) | >75 (P#30: 05-16-11) |

EZRIN INHIBITORS AND METHODS OF MAKING AND USING

This application claims the benefit of U.S. provisional patent application No. 61/375,823, filed Aug. 21, 2010, which is incorporated herein by reference.

STATEMENT REGARDING FEDERALLY SPONSORED RESEARCH

Part of the work performed during development of this invention utilized U.S. Government funds under Department of Defense, Grant No. W81XWH-10-1-0137. The U.S. Government has certain rights in this invention.

SEQUENCE LISTING INFORMATION

A computer readable text file, entitled "036681-5010-01US SequenceListing.txt," with a file size of about 1 kb contains the sequence listing for this application and is hereby incorporated by reference in its entirety.

FIELD OF THE INVENTION

The invention encompasses novel compounds and pharmaceutically acceptable salts thereof. The invention also encompasses methods for inhibiting the function of ezrin protein in a cell and methods for inhibiting the cancer cell or tumor growth, which methods include administering at least one compound of the invention or a pharmaceutically acceptable salt thereof.

BACKGROUND OF THE INVENTION

Ezrin is a multifunctional protein that connects the actin cytoskeleton to extracellular matrix through transmembrane proteins. High ezrin expression is associated with lung metastasis and poor survival rates in cancer.

Osteosarcoma (OS) is the most common type of primary bone cancer in children and adolescents. The pathogenesis underlying the disease has been difficult to establish due to its heterogenous histology and complex etiology. Treatment of the localized disease has improved with introduction of neoadjuvant chemotherapy, increasing the 5-year survival to 60-70%. However, 5-year survival of patients with metastasis at diagnosis decreases to 30% (Zhang, P., et al., *Clin. Cancer Res.*, 14, 2962-2969 (2008); Rosen G., et al., *Cancer*, 49, 1221-1230 (1982); Ferrari, S. & Palmerini, E., *Curr. Opin. Oncol.*, 19, 341-346 (2007); Bacci, G., et al., *Cancer*, 106, 1154-1161 (2006)). In OS, the predominatnt site of recurrence and the main cause of death are pulmonary metastases (Dunn, D. & Dehner, L. P., *Cancer*, 40, 3054-3064 (1977)). Targeting the underlying molecular events that lead to metastasis could provide dramatic benefits for the treatment of patients with poor prognosis.

Ezrin is a member of the ERM (Ezrin/Radixin/Moesin) family of proteins and is conserved through evolution both structurally and functionally (Fievet, B., et al., *Biochim. Biophys. Acta*, 1773, 653-660 (2007)). By regulating membrane-cytoskeleton complexes, it plays key roles in normal cellular processes like maintenance of membrane dynamics, survival, adhesion, motility, cytokinesis, phagocytosis and integration of membrane transport with signaling pathways (Bretscher, A., et al., *Nat. Rev. Mol. Cell. Biol.*, 3, 586-599 (2002)). Both in vivo and in vitro studies show ezrin function is actively regulated by its conformational changes (Fievet, B., et al., *Biochim. Biophys. Acta*, 1773, 653-660 (2007)). Ezrin exists in an inactive conformation, in which the membrane and actin binding sites are masked by intramolecular interaction of the N-terminal and the last 100 amino acids of the long Carboxy terminal domains (Gary, R. & Bretscher, *Mol. Biol. Cell*, 6, 1061-1075 (1995)). In its active-open confirmation, it functions as a crosslinker between the plasma membrane and the cortical cytoskeleton. Two factors are reported to be involved in this conformational transition, binding of N-terminal domain to the phosphotidylinositol 4,5 biphosphates (PIP$_2$) and phosphorylation of a conserved threonine at residue 567 (T567) in the F-actin binding site (Fievet, B., et al., *Biochim. Biophys. Acta*, 1773, 653-660 (2007)). Several serine/threonine kinases, Rho kinase (ROCK), protein kinase C-alpha (PKCα) and MST4, are reported to be important for T567 phosphorylation (Matsui, T., et al. *J. Cell Biol.*, 140, 647-657 (1998); Ren, L., et al. *Oncogene*, 28, 792-802 (2009); Ten Klooster, J. P., et al. *Dev. Cell*, 16, 551-562 (2009)). In its active form, ezrin can interact with membrane proteins either directly or through adaptor proteins. It binds to adhesion related proteins with single transmembrane domains such as CD43, CD44, CD95, ICAM-1, -2, -3 and PA.2.26 antigen directly through their cytoplasmic tails (Louvet-Vallee, S., *Biol. Cell*, 92, 305-316 (2000)), which modulates cell motility and cellular morphology (Legg, J. W. & Isache, *Curr. Biol.*, 8, 705-708 (1998)). Ezrin binding to adaptor proteins such as EBP50/NHE-RF and E3KARP regulates the activity of ion transporters, endocytosis of plasma membrane proteins and interaction of F-actin to specific plasma membrane domains (Bretscher, A., et al., *Nat. Rev. Mol. Cell. Biol.*, 3, 586-599 (2002)). In addition to plasma membrane proteins, ezrin associates with cytoplasmic signaling proteins and is involved in several signaling pathways, such as but not limited to Rho and PI3K/Akt pathways (Gautreau, A., et al., *Proc. Natl. Acad. Sci. USA*, 96, 7300-7305 (1999); and Hirao, M., et al. *J. Cell Biol.*, 135, 37-51 (1996)). Ezrin can modulate these pathways at both upstream and the downstream levels.

Accumulating evidence from experimental mouse models, as well as canine and human patients validate that ezrin is a key factor in metastases. In this study, we identified that the compounds described herein directly interact with ezrin and inhibit its biological function in multiple assays.

SUMMARY OF THE INVENTION

The invention encompasses a compound of Formula (I),

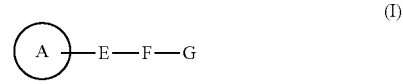

(I)

and salts or prodrugs thereof, wherein:
E, F and G are optionally independently present;

is

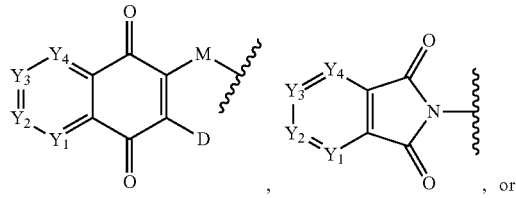

, or

-continued

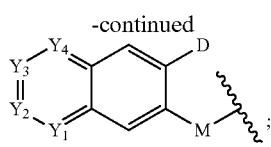

wherein $Y_1$, $Y_2$, $Y_3$, and $Y_4$ are each independently N or C—Z; wherein Z is H or a $C_1$ to $C_6$ linear, branched or cyclic alkyl group;

M and D are not both hydrogen;

D is H, halogen, OH, aryl, aryloxy, $NO_2$, CN, carboxy, SH, $CF_3$, $C_1$ to $C_{10}$ alkoxy, $NH_2$, or $NR_{13}R_{14}$; wherein $R_{13}$ and $R_{14}$ are each independently H, $C_1$ to $C_{15}$ straight chain or branched chain alkyl;

wherein when none of E, F and G are present, M is H, halogen, OH, aryl, aryloxy, $NO_2$, CN, carboxy, SH, $CF_3$, $C_1$ to $C_{10}$ alkoxy, $NH_2$, or $NR_{13}R_{14}$;

wherein when at least one of E, F and G are present, M is —NH—, —O—, or —S—;

E is a bond, linear, branched or cyclic $C_1$ to $C_{10}$ alkylene, alkene, alkyne, or ether;

F is a bond, O, S,

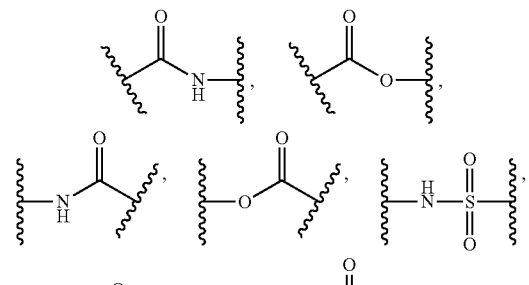

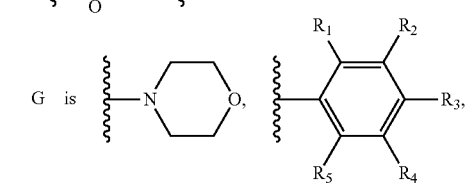

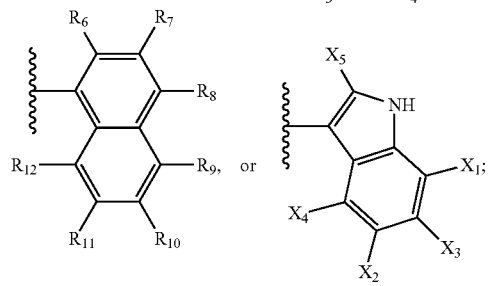

wherein $R_1$-$R_{12}$ and $X_1$-$X_5$ are each independently selected from H, halogen, OH, aryl, aryloxy, $NO_2$, CN, carboxy, SH, $CF_3$, $C_1$ to $C_5$ alkoxy group, $C_1$ to $C_5$ alkyl group, $NHCONH_2$, NH—$SO_2CH_3$, NH—NH—$NH_2$, $NH_2$, or $NR_{13}R_{14}$;

with the proviso that when $R_3$ is OH and

is

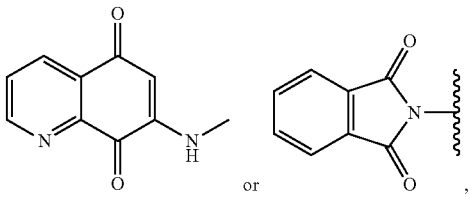

$R_2$ and $R_4$ are not both H, OH, or the same halogen.

According to one embodiment,

is

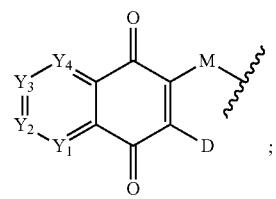

and none of E, F and G are present. In a more specific embodiment, D is hydrogen; and M is $NR_{13}R_{14}$ in the above-described compound.

According to another embodiment,

is

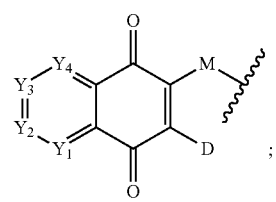

and none of E, F and G are present;

wherein at least one of M or D is $NH_2$ or $NR_{13}R_{14}$.

In other embodiments,

A is

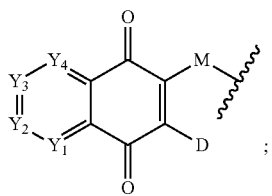

and
E, F and G are all present;
wherein M is —NH—. In a more specific embodiment, D is H, E is a $C_1$ to $C_5$ linear alkylene, F is a bond, and G is

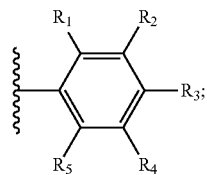

In other embodiments,

Ⓐ is

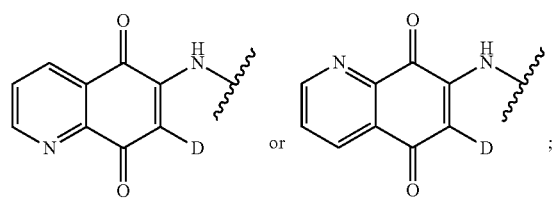 [SMILES: *NC1=C([2H])C(=O)c2ncccc2C1=O ; *NC1=C([2H])C(=O)c2cccnc2C1=O]

and
E is —$(CH_2)_2$—,
F is bond, and
G is

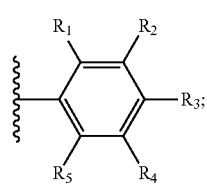

wherein $R_3$ is hydroxy or methoxy.
In other embodiments,

Ⓐ is

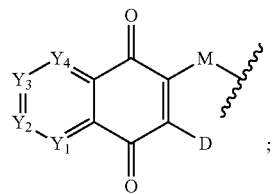

and
E, F and G are all present;
wherein F is a bond; and G is

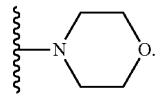

In other embodiments,

Ⓐ is

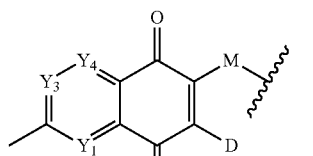 or

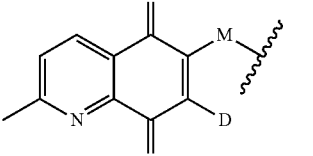 or

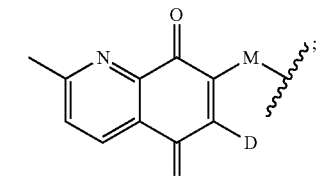

and
E, F and G are all present.
In other embodiments,

Ⓐ is

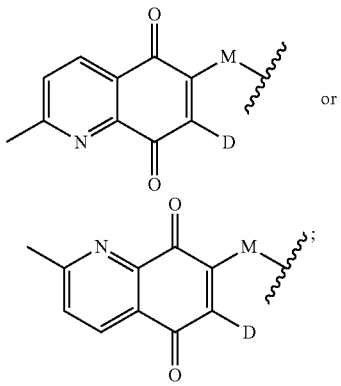

none of E, F, and G are present. In a more specific embodiment, M is a $C_1$ to $C_{10}$ alkoxy; and D is $NH_2$ in the above-described compound.

In other embodiments,

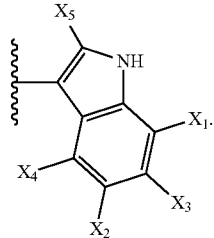

is

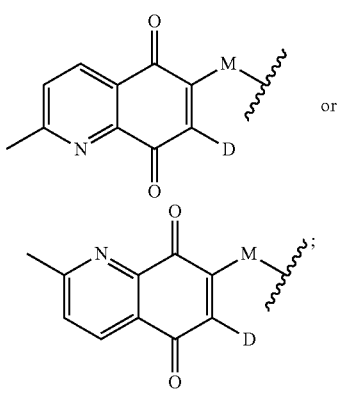

none of E, F, G are present, and M is methoxy.

In one specific embodiment,

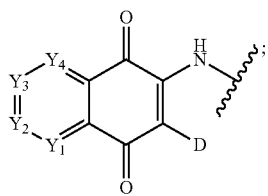

is

E is a $C_1$ to $C_5$ linear, branched or substitute alkylene;
F is a bond; and
G is

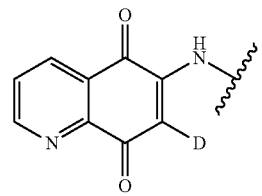

In another specific embodiment,

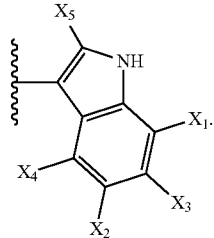

is

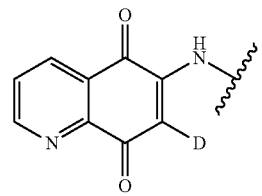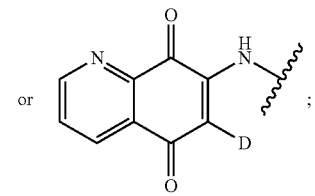

and
E is $—(CH_2)_2—$;
F is a bond;
G is

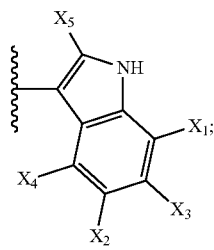

wherein $X_2$ is H, hydroxy, fluorine, methoxy or methyl.

In another embodiment, is
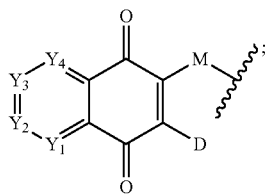
E is a $C_1$ to $C_5$ linear alkylene;
F is
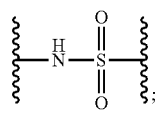
G is
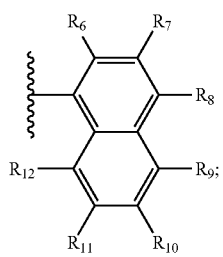
wherein $R_9$ is $NH_2$, $-N(CH_3)_2$, or $NR_{13}R_{14}$.
In specific embodiments,
Ⓐ
is
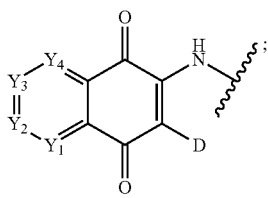
E is a $C_1$ to $C_5$ linear alkylene;
F is
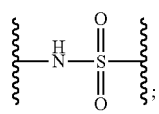
and
G is
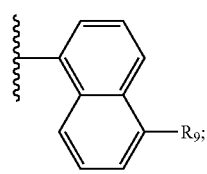
wherein $R_9$ is $NH_2$ or $NR_{13}R_{14}$.
In other embodiments,
Ⓐ
is
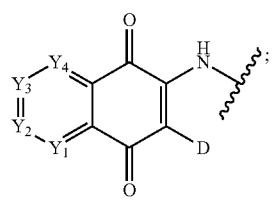
E is a $C_1$ to $C_5$ linear alkylene;
F is
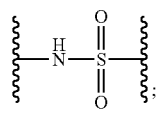
and
G is
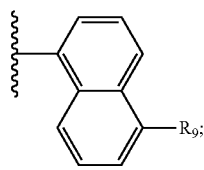
wherein D is hydrogen and $R_9$ is $-N(CH_3)_2$.
In other embodiments,
Ⓐ
is
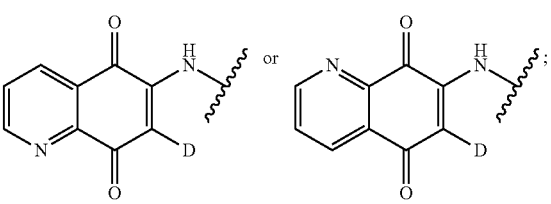 [SMILES: *NC1=C([2H])C(=O)c2ncccc2C1=O ; *NC1=C([2H])C(=O)c2cccnc2C1=O]

E is —(CH$_2$)$_2$—;

F is

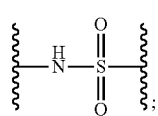 [SMILES: *NS(*)(=O)=O]

and

G is

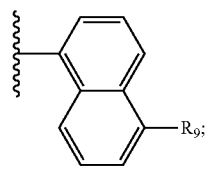

wherein R$_9$ is NH$_2$, —N(CH$_3$)$_2$, or NR$_{13}$R$_{14}$.

In other embodiments,

Ⓐ is

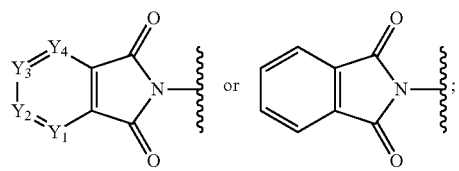

E is —(CH$_2$)$_2$—, or C$_1$ to C$_5$ linear alkylene;

F is a bond; and

G is

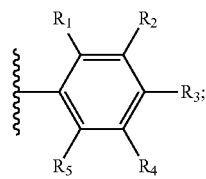

wherein R$_3$ is hydroxy or methoxy.

In other embodiments,

Ⓐ is

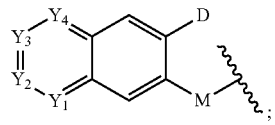

and none of E, F and G are present.

In other embodiments,

Ⓐ is

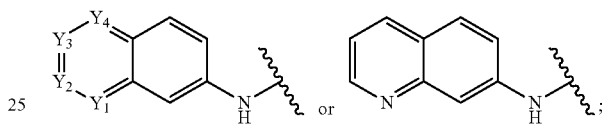

E is —(CH$_2$)$_2$—, or C$_1$ to C$_6$ linear, branched, or cyclic alkylene;

F is a bond; and

G is

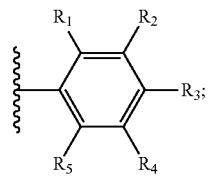

wherein R$^3$ is hydroxy or methoxy.

According to one embodiment,

Ⓐ is

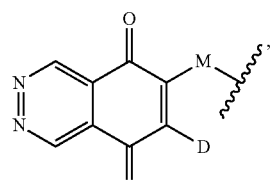

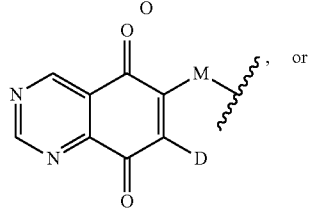

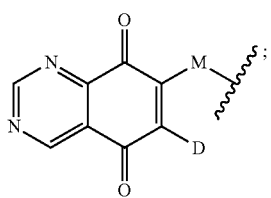
E is —(CH$_2$)$_2$—, or C$_1$ to C$_6$ linear, branched, or cyclic alkylene;
F is a bond; and
G is
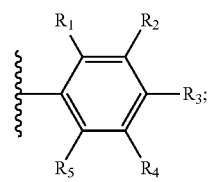
wherein D is hydrogen; M is —NH—; R$_1$ and R$_5$ are both hydrogen; R$_3$ is hydroxy or methoxy.
Specific embodiments of the invention encompass but are not limited to:
NSC 76886
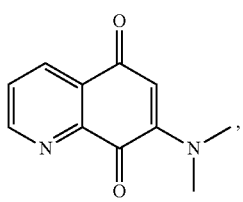
NSC 105808
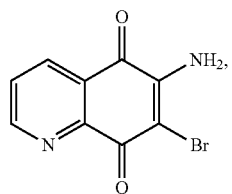
NSC 132493
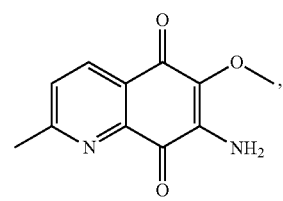
NSC 193688
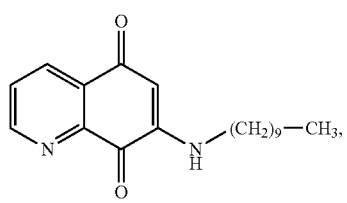
NSC 663284
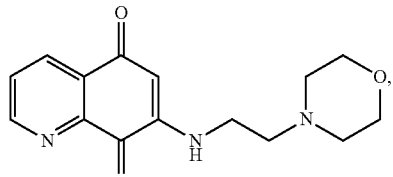
GK2-013
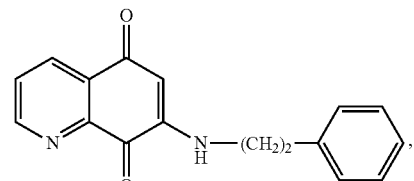
GK2-037
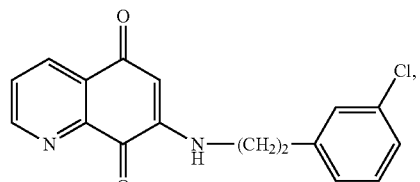
GK2-043
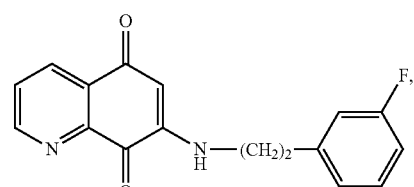
GK2-047
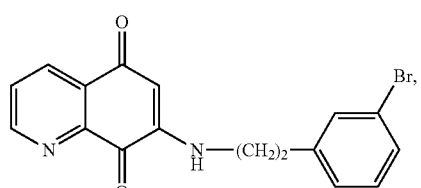
GK2-053
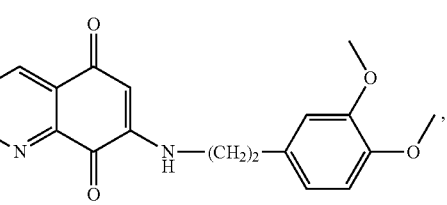
GK2-057
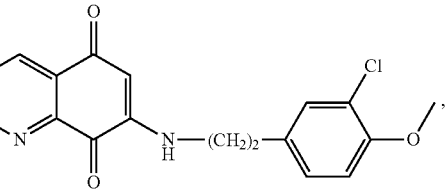
GK2-059
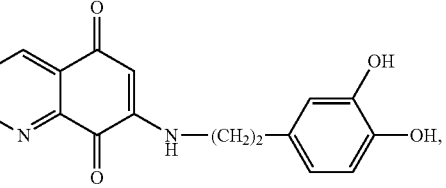

GK3-025
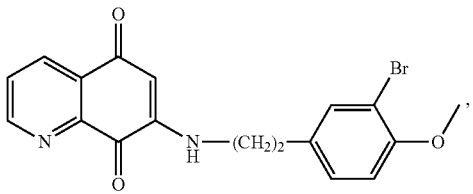
GK 2-085
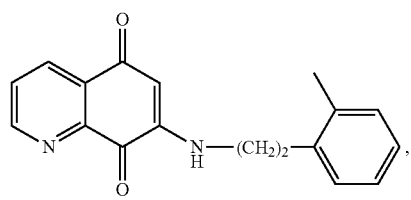
GK2087
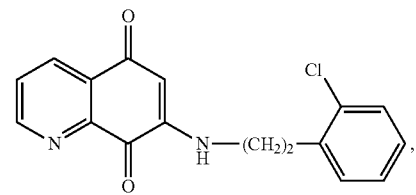
GK2-095
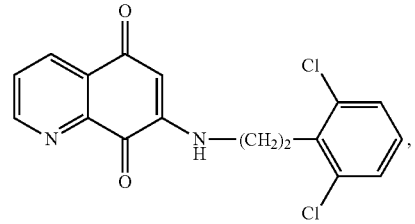
GK2-107
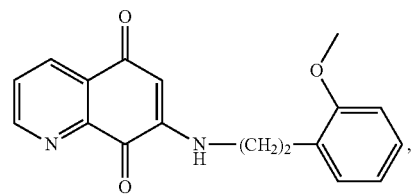
GK2-109
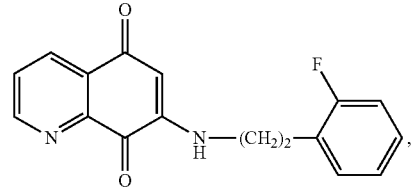
GK2-139
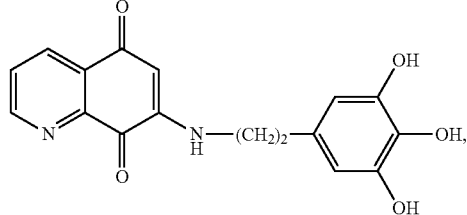
GK2-217
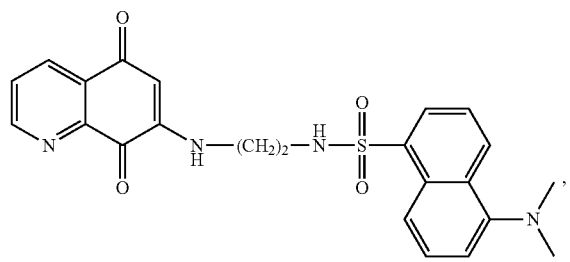
GK2-081
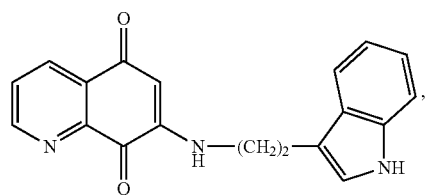
GK2-115
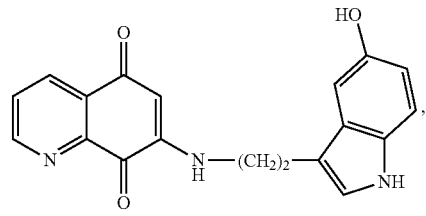
GK2-123
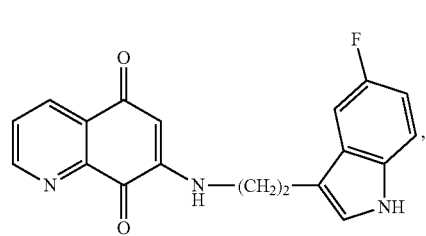
GK2-127
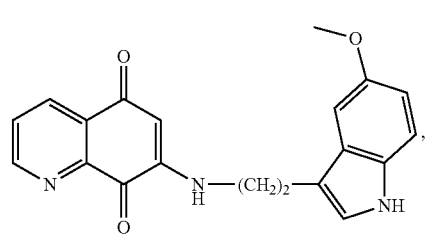
GK2-135
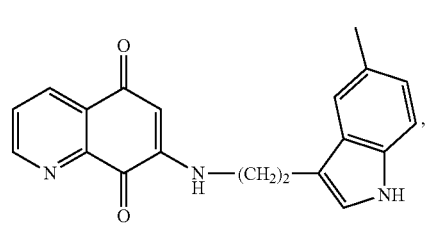
GK2-303
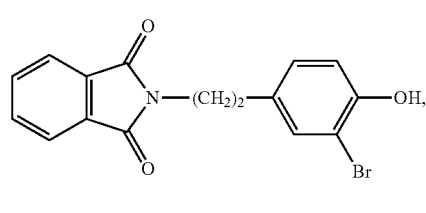

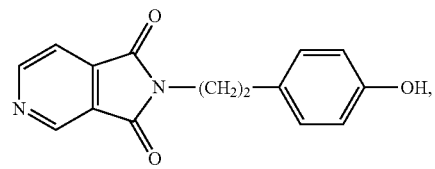
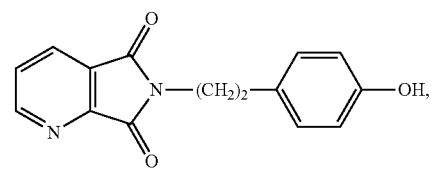
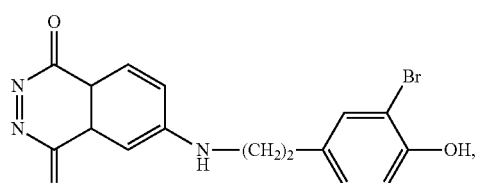
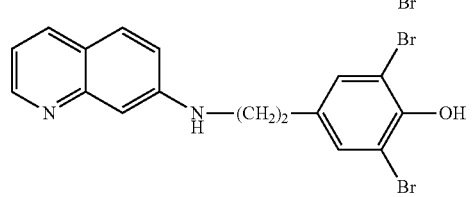
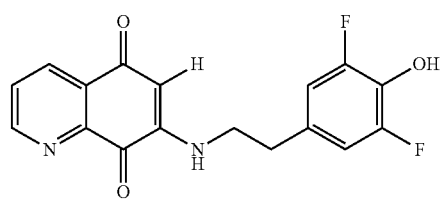
GK3-189
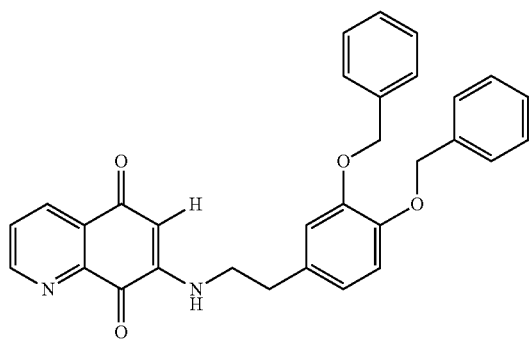
GK3-129
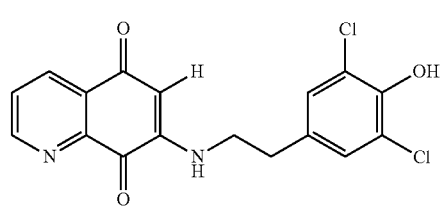
GK3-015
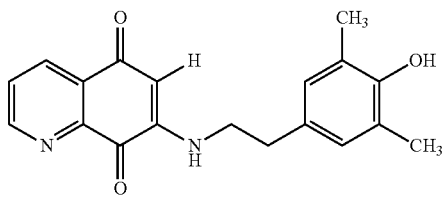
GK3-209
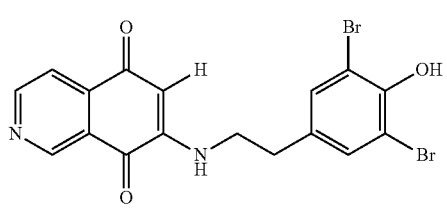
GK3-115
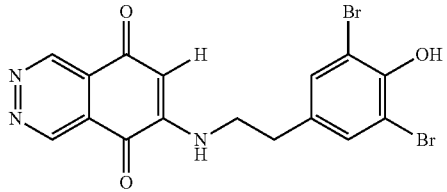
GK3-135
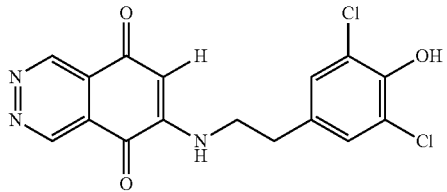
GK3-185
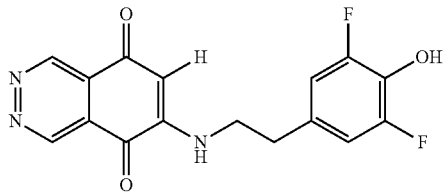
GK3-201
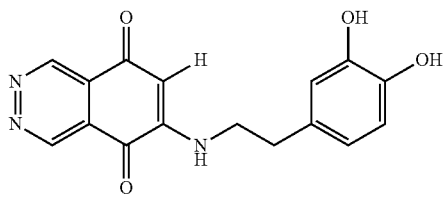
GK3-141
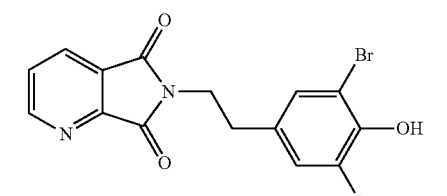
GK3-103
Notebook ID: GK3-103

-continued

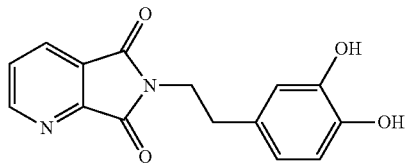

GK3-107

The present invention includes, but is not limited to compounds of Formula I and salts thereof.

In certain illustrative embodiment, the invention encompasses a pharmaceutical composition comprising a compound of formula I or a pharmaceutically acceptable salt thereof.

In one aspect, there is provided a method of inhibiting ezrin protein function in a cell comprising administering at least of one compound as described herein. In one embodiment, the cell is an abnormal cancer cell.

In another aspect, there is provided a method of inhibiting the growth of a cancer cell comprising administering to the cell at least one compound described, herein in an amount sufficient to inhibit the growth of the cancer cell. In one embodiment, the cell is selected from the group consisting of a lung cancer cell, a breast cancer cell, a colon cancer cell, a malignant melanoma cell, an ovarian carcinoma cell, a brain tumor cell, a soft tissue sarcoma cell, a rhabdomyosarcoma cell, a pancreatic cancer cell, a prostate cancer cell and an osteosarcoma cell. In one specific embodiment, the cell is an osteosarcoma cell. In another embodiment, the cell is in a subject, and the subject is in need of treatment for cancer.

In a further aspect of the present invention, there is provided a method reducing the likelihood of cancer metastasis in a subject in need of treatment thereof, the method comprising administering a therapeutically effective amount of at least one compound described herein. In one embodiment, the cancer is selected from the group consisting of lung cancer, breast cancer, colon cancer, malignant melanoma, ovarian carcinoma, brain tumors, soft tissue sarcomas, rhabdomyosarcoma, pancreatic cancer, prostate cancer and osteosarcoma. In one specific embodiment, the cancer is an osteosarcoma.

The present invention may be understood more fully by reference to the figures, detailed description, and examples, which are intended to exemplify non-limiting embodiments of the invention.

BRIEF DESCRIPTION OF THE DRAWINGS

FIG. 10 provide data showing compounds reduced T567 phosphorylation of ezrin and functional activity. K7M2 cells that were treated with embodied compounds and resolved protein lysates were immunoblotted for co-precipitated phosphorylated ezrin (TOP), or actin (BOTTOM). $4.0\times10^6$ K7M2 cells were plated in 15 cm dishes. After 24 h, the plates are at least 70% confluent. Media was removed and either 7 μM or 10 μM of compound in SF DMEM was added. After the ezrin protein was incubated for 5 h with the indicated compound, the plates were lysed with PLB containing Calyculin A. 2 μL of Ezrin Ab and 10 μM of the compound (prepared in PLB) were added to the lysate and allowed to incubate overnight (14 h), followed by tumbling with Agarose IgG beads. The mixture was run on 10% acrylamide gel and transferred overnight.

Figure 1D:
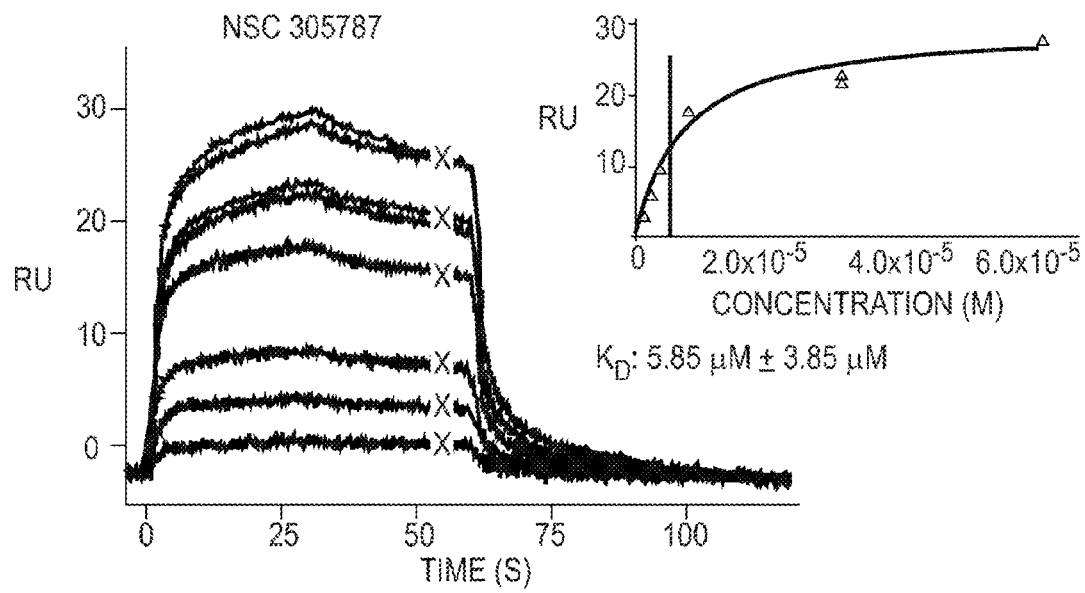
FIG. 1 illustrates that NSC305787 and NSC668394 directly interact with ezrin. (A) WT and T567D mutant forms of recombinant mouse ezrin proteins were expressed in bacteria. The most prominent band in total bacterial lysate following IPTG induction appeared just above 75 kD molecular weight marker on a 10% PAGE gel stained with coomassie blue (lanes 2 vs 3 and 5 vs 6). The best fractions from column chromatography purifications for each protein are shown on lanes 4 and 7 (arrow). (B) K12 OS cell lysate was mixed with ezrin proteins and subjected to immunoprecipitation (IP) with an ezrin antibody. Cellular actin binding to these two proteins was detected by immunoblotting (IB) with an actin antibody. Equal loading of ezrin proteins was determined by blotting with an ezrin antibody. T567D ezrin showed stronger binding to actin than the WT. (C) Chemical structures of NSC305787 and NSC668394 (D) Direct binding of NSC305787 to WT ezrin protein is analyzed by SPR. Average affinity for NSC305787 binding to ezrin from 5 independent experiments was calculated to be 5.85 µM (±s.d. 3.85 µM). A representative set of binding curves are presented with the steady state affinity curve given in the inset. (E) NSC668394 bound to WT ezrin with an average KD of 12.59 µM (data from 5 independent experiments with ±s.d. 6.35 µM). Black lines show actual data points, red lines show curve fits for 1:1 binding model in Biacore T-100 evaluation software.

Ezrin-PABP1 interaction was also evaluated in an ELISA experiment where recombinant ezrin protein was immmobilized on surface and total cell lysates from osteosarcoma cells were applied on top. Amount of PABP1 binding to ezrin on the surface was detected by a anti-PABP1 primary antibody followed by enzyme linked secondary antibody. (C) Immunoprecipitation and western experiment was prepared as described in panel A. Cells were treated with NSC305787 (compound 8) and NSC668394 (compound 16) for 60 min prior to immunoprecipitation. Both NSC305787 and NSC668394 inhibited interaction of PABP1 with ezrin

DETAILED DESCRIPTION OF THE INVENTION

As used herein and unless otherwise indicated, the term "alkyl" means a substituted or unsubstituted, saturated, monovalent linear or branched hydrocarbon chain. Examples of alkyl groups include, but are not limited to, $C_1$ to $C_{15}$ linear, branched or cyclic alkyl, such as methyl, ethyl, propyl, isopropyl, cyclopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, sec-butyl, t-butyl, cyclobutyl, pentyl, isopentyl, neopentyl, hexyl, and cyclohexyl and longer alkyl groups, such as heptyl, octyl, nonyl and decyl. An alkyl can be unsubstituted or substituted with one or two suitable substituents.

As used herein and unless otherwise indicated, the terms "alkoxy" or "alkyloxy" means an —O-alkyl, wherein alkyl is as defined herein. An alkoxy can be unsubstituted or substituted with one or two suitable substituents. Preferably, the alkyl chain of an alkyloxy is from 1 to 5 carbon atoms in length, referred to herein, for example, as "$(C_1-C_5)$alkoxy." Preferably, the alkyl chain of an alkyloxy is from 1 to 10 carbon atoms in length, referred to herein, for example, as "$(C_1-C_{10})$alkoxy."

As used herein and unless otherwise indicated, the term "alkylene" means a linear or branched or cyclic saturated divalent hydrocarbon radical. An alkylene can be unsubstituted or substituted with one or two suitable substituents. Examples of alkylene groups include, but are not limited to, $C_1$ to $C_{10}$ linear chain or branched chain alkylene, such as, methylene, ethylene, propylene, isopropylene, cyclopropylene, 2-methylpropylene, 2-methylpropylene, 2-methylbutylene, 3-methylbutylene, 2-methylbutylene, 2,2-dimethylpropylene, 2-methylpentylene, 3-methylpentylene, 4-methylpentylene, 2-methylpentylene, 3-methylpentylene, 4-methylpentylene, 2,2-dimethylbutylene, 3,3-dimethylbutylene, 2-ethylbutylene, butylene, isobutylene, t-butylene, cyclobutylene, pentylene, isopentylene, neopentylene, cyclopentylene, hexylene, 2-methylpentylene, 3-methylpentylene, and cyclohexylene.

As used herein and unless otherwise indicated, the terms "alkene" or "alkenyl group" means a monovalent linear, branched or cyclic hydrocarbon chain having one or more double bonds therein. The double bond of an alkene can be unconjugated or conjugated to another unsaturated group. An alkene can be unsubstituted or substituted with one or two suitable substituents. Suitable alkenes include, but are not limited to $(C_2-C_8)$alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl. An alkene can be unsubstituted or substituted with one or two suitable substituents.

As used herein and unless otherwise indicated, the terms "alkyne" or "alkynyl group" means monovalent linear, branched or cyclic hydrocarbon chain having one or more triple bonds therein. The triple bond of an alkynyl group can be unconjugated or conjugated to another unsaturated group. An alkyne can be unsubstituted or substituted with one or two suitable substituents. Suitable alkynes include, but are not limited to, $(C_2-C_8)$alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents.

As used herein and unless otherwise indicated, the term "aryl" means a monocyclic or polycyclic aromatic ring comprising carbon and hydrogen atoms. Examples of suitable aryl groups include, but are not limited to, phenyl, tolyl, anthacenyl, fluorenyl, indenyl, azulenyl, and naphthyl. An aryl group can be unsubstituted or substituted with one or two suitable substituents. Preferably, the aryl group is a monocyclic ring, wherein the ring comprises 6 carbon atoms, referred to herein as "$(C_6)$aryl."

As used herein and unless otherwise indicated, the term "aryloxy" means an —O-aryl group, wherein aryl is as defined herein. An aryloxy group can be unsubstituted or substituted with one or two suitable substituents. Preferably, the aryl ring of an aryloxy group is a monocyclic ring, wherein the ring comprises 6 carbon atoms, referred to herein as "$(C_6)$aryloxy."

As used herein and unless otherwise indicated, the term "ether" means a group of formula alkyl-O-alkyl, alkyl-O-alkynyl, alkyl-O-aryl, alkenyl-O-alkenyl, alkenyl-O-alkynyl, alkenyl-O-aryl, alkynyl-O-alkynyl, alkynyl-O-aryl, aryl-O-aryl, wherein "alkyl", "alkenyl", "alkynyl" and "aryl" are defined herein.

As used herein and unless otherwise indicated, the term "carboxy" means a radical of the formula: —COOH.

As used herein and unless otherwise indicated, the term "halogen" means fluorine, chlorine, bromine, or iodine. Correspondingly, the meaning of the terms "halo" and "Hal" encompass fluoro, chloro, bromo, and iodo.

As used herein and unless otherwise indicated, the terms "substituted" and "a suitable substituent" means a group that does not nullify the synthetic or pharmaceutical utility of the compounds of the invention or the intermediates useful for preparing them. Examples of substituted groups or suitable substituents include, but are not limited to: $(C_1-C_{10})$alkyl; $(C_1-C_{10})$alkenyl; $(C_1-C_{10})$alkynyl; $(C_6)$aryl; $(C_3-C_5)$heteroaryl; $(C_3-C_7)$cycloalkyl; $(C_1-C_{10})$alkoxy; $(C_6)$aryloxy; —CN; —OH; SH, oxo; halo, —$NO_2$, —$CO_2H$; —$NH_2$; —NHOH, —NH(($C_1-C_{10}$)alkyl); —N(($C_1-C_{10}$)alkyl)$_2$; —NH(($C_6$)aryl); —NHO(($C_1-C_{10}$)alkyl); —N(O($C_1-C_{10}$)alkyl)$_2$; —NH(O($C_6$)aryl); —S(($C_1-C_{10}$)alkyl); —S(($C_1-C_{10}$)alkyl)$_2$; —S(($C_6$)aryl); (=O); C(S), —N(($C_6$)aryl)$_2$; —CHO; —C(O)(($C_1-C_{10}$)alkyl); —C(O)(($C_6$)aryl); —$CO_2$(($C_1-C_{10}$)alkyl); and —$CO_2$(($C_6$)aryl), —C(S)(($C_1-C_{10}$)alkyl); —C(S)(($C_6$)aryl); —$SO_2$(($C_1-C_{10}$)alkyl); —$SO_2$(($C_6$)aryl), and —$SO_3H$, —C(S)O(($C_1-C_{10}$)alkyl); —C(S)(O(($C_6$)aryl). In certain illustrative embodiments, the substituents can be one or more than one suitable groups, such as, but not limited to, —F, —Cl, —Br, —I, —OH, azido, —SH, alkyl, aryl, heteroalky, alkyoxyl, alkylthiol, amino, hydroxylamino, N-alkylamino, —N,N-dialkylamino, —N,N-dimethylamino, acyl, alkyloxycarbonyl, sulfonyl, urea, —$NO_2$, triazolyl. One of skill in art can readily choose a suitable substituent based on the stability and pharmacological and synthetic activity of the compound of the invention.

As used herein and unless otherwise indicated, the term "compounds of the invention" means, collectively, the compounds of formula I and pharmaceutically acceptable salts thereof as well as compounds depicted herein. The compounds of the invention are identified herein by their chemical structure and/or chemical name. Where a compound is referred to by both a chemical structure and a chemical name, and that chemical structure and chemical name conflict, the chemical structure is determinative of the compound's identity. The compounds of the invention may contain one or more chiral centers and/or double bonds and, therefore, exist as stereoisomers, such as double-bond isomers (i.e., geometric isomers), enantiomers, or diastereomers. According to the invention, the chemical structures depicted herein, and therefore the compounds of the invention, encompass all of the corresponding compound's enantiomers and stereoisomers, that is, both the stereomerically pure form (e.g., geometrically pure, enantiomerically pure, or diastereomerically pure) and enantiomeric and stereoisomeric mixtures. Enantiomeric and stereoisomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and stereoisomers can also be obtained from stereomerically- or enantiomerically-pure intermediates, reagents, and catalysts by well known asymmetric synthetic methods.

The phrase "pharmaceutically acceptable salt(s)," as used herein includes but is not limited to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid salts of such basic compounds are those that form non-toxic acid salts, i.e., salts containing pharmacologically acceptable anions including, but not limited to, sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, compounds that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include compounds that comprise oligonucleotides, peptides, lipids, aliphatic and aromatic groups, or NO, $NO_2$, ONO, and $ONO_2$ moieties. Prodrugs can typically be prepared using well known methods, such as those described in Burger's Medicinal Chemistry and Drug Discovery, pp. 172, 178, 949, 982 (Manfred E. Wolff ed., 5th ed. 1995), and Design of Prodrugs (H. Bundgaard ed., Elsevier, N.Y. 1985).

Figure 11A:
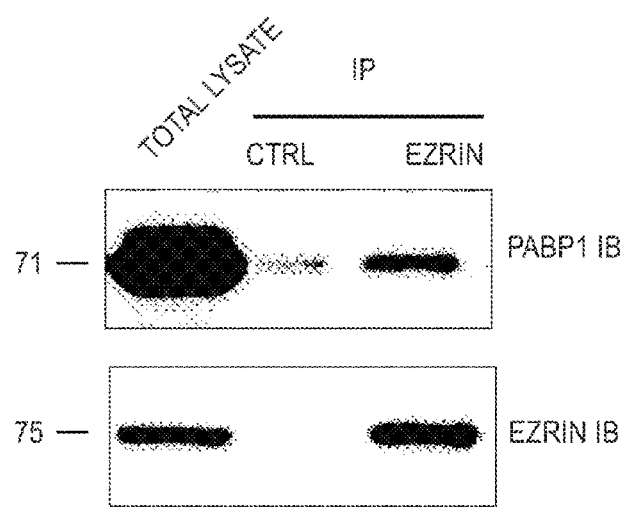
FIG. 11 shows the binding of ezrin and poly-A-binding protein 1 (PABP1) by immunoprecipitation and ELISA. (A) Total cell lysates from K7M2 osteosarcoma cells were immunoprecipitated by using an anti-ezrin antibody. As a control, non-specific total IgG was used. Immunoprecipitates were run on SDS-PAGE and Western Blot was performed using anti-ezrin (lower panel) and anti-PABP1 (upper panel) antibodies. PABP1 protein was detected in immunoprecipitates of ezrin, suggetsing that these two proteins interact with each other in a protein complex. (B)
Figure 11B:
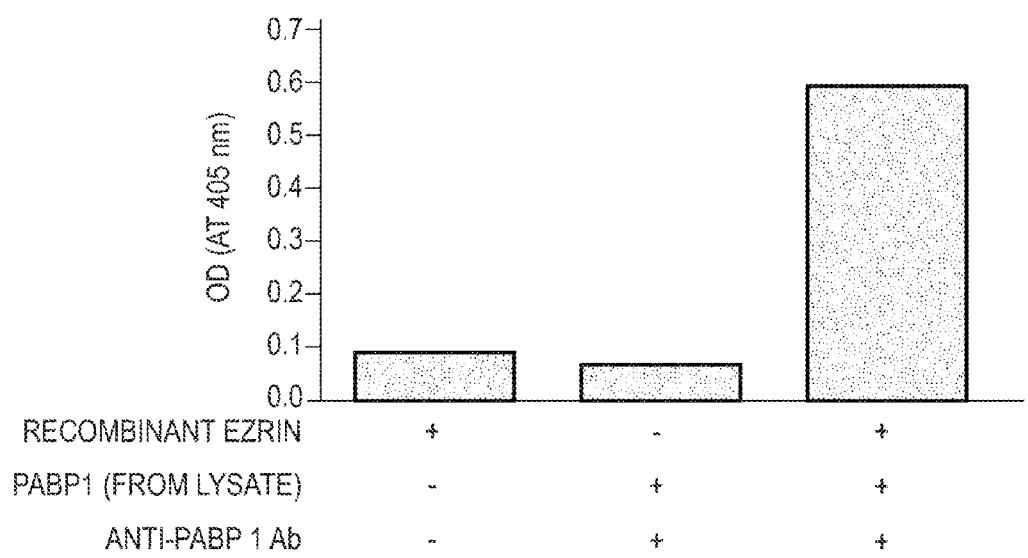
Figure 11C:
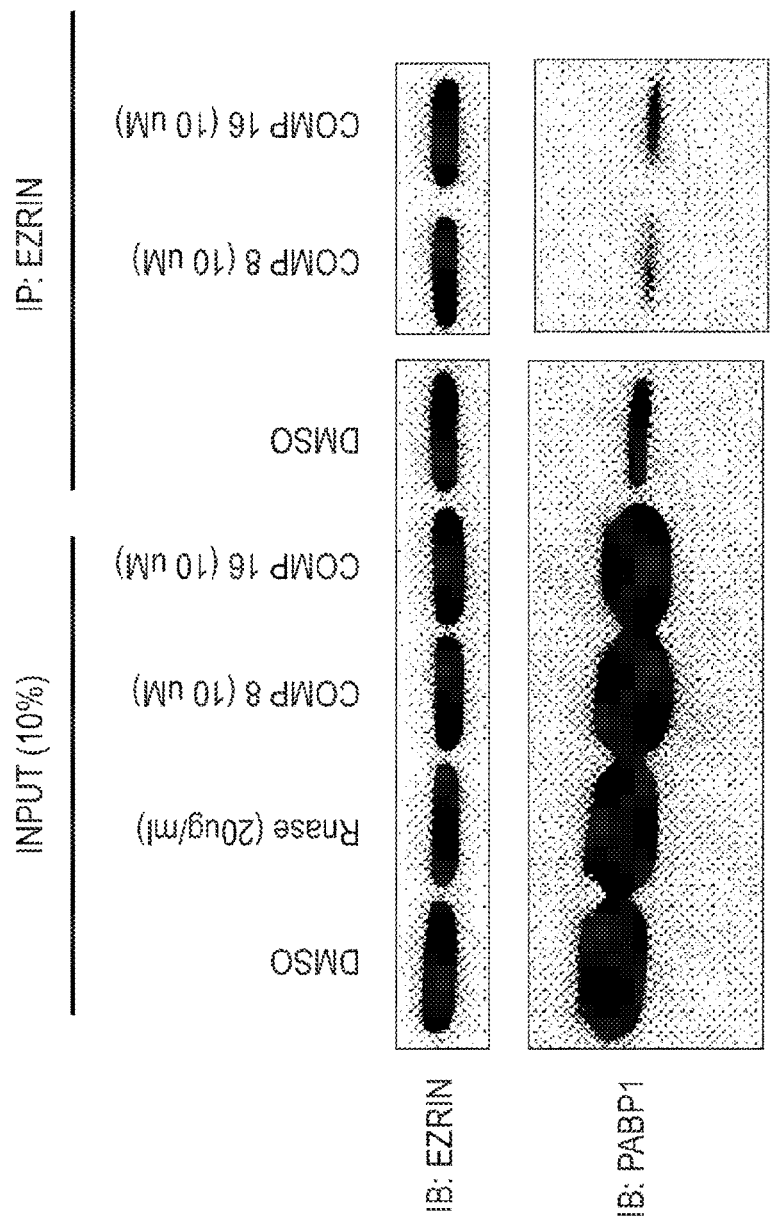

The term "ezrin" as used herein is used as it is in the art. It is understood that ezrin is a protein known to be involved in connections of cytoskeletal structures within the cell to the plasma cell membrane. Ezrin is known to have domains in common with talin protein. Ezrin exists in an inactive conformation, in which the membrane and actin binding sites are masked by intramolecular interaction of the N-terminal and the last 100 amino acids of the long carboxy terminal domains. In its active-open confirmation, ezrin functions as a crosslinker between the plasma membrane and the cortical cytoskeleton. Two factors are reported to be involved in this conformational transition, binding of N-terminal domain to the phosphotidylinositol 4,5 biphosphates ($PIP_2$) and phosphorylation of a conserved threonine at residue 567 (T567) in the F-actin binding site. Several serine/threonine kinases, Rho kinase (ROCK), protein kinase C-alpha (PKCα) and MST4, are also important for T567 phosphorylation. In its active form, ezin can interact with membrane proteins either directly or through adaptor proteins. Ezrin binds to adhesion related proteins with single transmembrane domains such as CD43, CD44, CD95, ICAM-1, -2, -3 and PA.2.26 antigen directly through their cytoplasmic tails, which modulates cell motility and cellular morphology. Ezrin binding to adaptor proteins such as EBP50/NHE-RF and E3KARP regulates the activity of ion transporters, endocytosis of plasma membrane proteins and interaction of F-actin to specific plasma membrane domains. In addition to plasma membrane proteins, ezrin associates with cytoplasmic signaling proteins and is involved in several signaling pathways, such as but not limited to Rho and PI3K/Akt pathways. In addition, ezrin may also be involved in the modulation of nuclear processes such as transcription and RNA processing. For example, ezrin may bind to one or more types of Forkhead Box (Fox) proteins, which would suggest that ezrin may also play a role in transcription. Ezrin can also bind to poly-A-binding protein 1 (PABP1), see FIG. 11, which suggests that ezrin may play a role in translation and/or possibly mRNA transport from the nucleus to the cytoplasm, which would also affect translation. Ezrin can modulate these pathways at both upstream and the downstream levels.

As used herein, "inhibiting the function of ezrin" can be related to any of these currently known functions of ezrin. Moreover, the term "inhibiting," when used in connection with ezrin function, means a reduction in any downstream effect in which ezrin has a role. The inhibition could be due to any aspect of normal ezrin function, such as but not limited to the reduced binding of ezrin to any of its natural binding partners, the inhibition or reduction of the phosphorylation of ezrin, a loss of association of ezrin with any of its adaptor proteins and the like.

As used herein and unless otherwise indicated, the term "subject" means mammals and non-mammals. Mammals means any member of the mammalia class including, but not limited to, humans, non-human primates such as chimpanzees and other ape and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex, and is used herein interchangeably with "patient."

The terms "treating" or "inhibiting" when used in connection with an abnormal condition, e.g., cancer, are intended to include preventing, eradicating, reducing the likelihood or preventing the resulting increase of undesired physiological activity associated with a disorder, for example, in the context of the therapeutic or prophylactic methods of the invention. In another embodiment, the term treating or inhibiting includes antagonistic effects, e.g., diminishment of the activity or production of mediators of a disorder, reducing the rate of proliferation of abnormal cells, etc.

As used herein and unless otherwise indicated, the terms "cancer" or "cancer cell" refer to abnormal cell growth or proliferation that may or may not include spontaneous or induced phenotypic changes. As used herein, "cancer" includes but is not limited to such abnormal conditions as hypertrophy, neoplasia, hyperplasia, benign and malignant cancer. As used herein, the term "tumor" is a general term that includes hypertrophies, neoplasias, hyperplasias, benign cancers and malignant cancers. Accordingly, certain embodiments of the present invention include but are not limited to treating a hypertrophy, a neoplasia, a hyperplasia, a benign or a malignant cancer in a subject. In additional embodiments, the present invention is directed to preventing or reducing the likelihood of metastasis and/or recurrence of a hypertrophy, a neoplasia, a hyperplasia, a benign or a malignant cancer within a subject comprising administering at least one compound of the present invention to the subject. For example, at least one compound of the present invention may be administered after tumor resection/removal/ablation, etc. to reduce the likelihood of recurrence of the tumor in the subject. In another example, at least one compound of the present invention may be administered to reduce the likelihood of metastasis of the tumor in the subject.

As used herein and unless otherwise indicated, the phrase "therapeutically effective amount" of a composition of the invention is measured by the therapeutic effectiveness of a compound of the invention, wherein at least one adverse effect of a disorder is ameliorated or alleviated.

When administered to a cell, the compounds of the invention can be optionally administered in isolated form. As used herein, "isolated" means that the compounds of the invention are separated from other components of either (a) a natural source, such as a plant or cell, preferably bacterial culture, or (b) a synthetic organic chemical reaction mixture. In one embodiment, the compounds of the invention are purified. As used herein, "purified" means that when isolated, the isolate contains at least about 80% of a compound of the invention by weight of the isolate. In one embodiment, the isolates contain at least about 90%, at least-about 95% or at least about 99% of the compound of the invention by weight.

The invention encompasses compound and pharmaceutical composition comprising the compound of the following Formula (I):

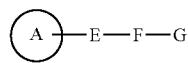

(I)

or pharmaceutically acceptable salts or prodrugs thereof.

According to one aspect the present invention provides a compound and pharmaceutical compositions comprising the compound of the following Formula (I):
or pharmaceutically acceptable salts and prodrugs thereof, wherein:

E, F and G are optionally independently present;

is

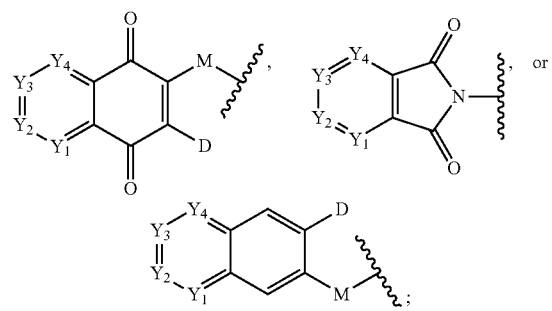

wherein
$Y_1$, $Y_2$, $Y_3$, and $Y_4$ are each independently N or C—Z; wherein Z is H or a $C_1$ to $C_6$ linear, branched or cyclic alkyl group;

M and D are not both hydrogen;

D is H, halogen, OH, aryl, aryloxy, $NO_2$, CN, carboxy, SH, $CF_3$, $C_1$ to $C_{10}$ alkoxy, $NH_2$, or $NR_{13}R_{14}$; wherein $R_{13}$ and $R_{14}$ are each independently H, $C_1$ to $C_{15}$ straight chain or branched chain alkyl;

wherein when none of E, F and G are present, M is H, halogen, OH, aryl, aryloxy, $NO_2$, CN, carboxy, SH, $CF_3$, $C_1$ to $C_{10}$ alkoxy, $NH_2$, or $NR_{13}R_{14}$;

wherein when at least one of E, F and G are present, M is —NH—, —O—, or —S—;

E is a bond, linear, branched or cyclic $C_1$ to $C_{10}$ alkylene, alkene, alkyne, or ether;

F is a bond, O, S,

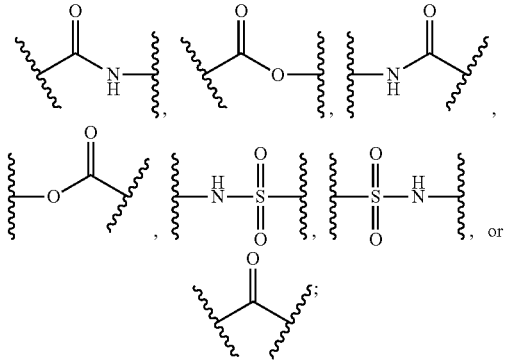

and
G is

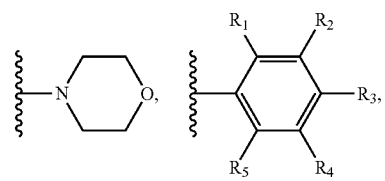

-continued

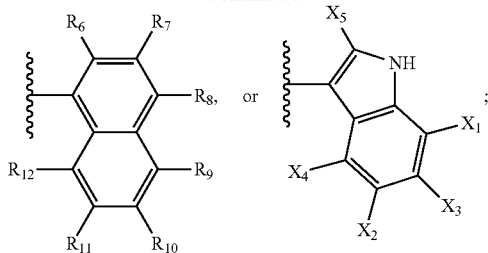 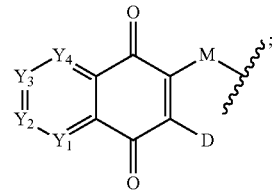

wherein
$R_1$-$R_{12}$ and $X_1$-$X_5$ are each independently selected from H, halogen, OH, aryl, aryloxy, $NO_2$, CN, carboxy, SH, $CF_3$, $C_1$ to $C_5$ alkoxy group, $C_1$ to $C_s$ alkyl group, $NHCONH_2$, $NH-SO_2CH_3$, $NH-NH-NH_2$, $NH_2$, or $NR_{13}R_{14}$;

with the proviso that when $R_3$ is OH and

is

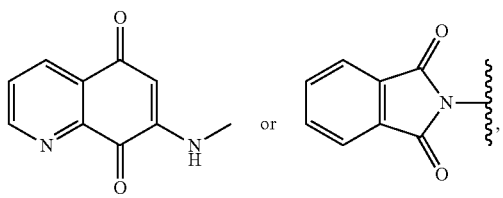

$R_2$ and $R_4$ are not both H, OH, or the same halogen.

According to one embodiment,

is

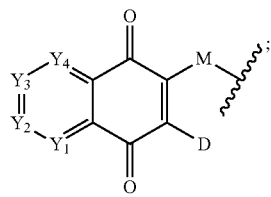

and
none of E, F and G are present. In a more specific embodiment, D is hydrogen; and
M is $NR_{13}R_{14}$ in the above-described compound.

According to another embodiment,

is

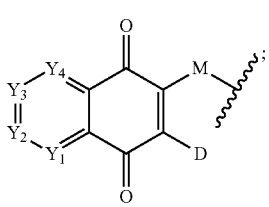

and
none of E, F and G are present;
wherein at least one of M or D is $NH_2$ or $NR_{13}R_{14}$.

In other embodiments,

is

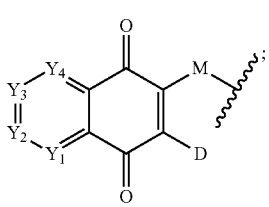

and
E, F and G are all present;
wherein M is $-NH-$. In a more specific embodiment, D is H, E is a $C_1$ to $C_5$ linear alkylene, F is a bond, and G is

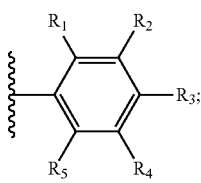

In other embodiments,

is

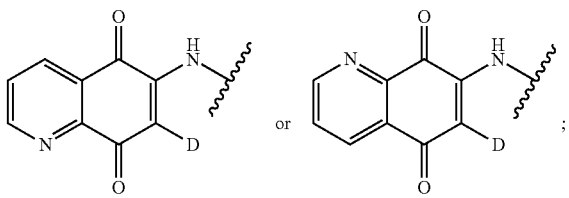 [SMILES: *NC1=C([2H])C(=O)c2ncccc2C1=O ; *NC1=C([2H])C(=O)c2cccnc2C1=O]

and

E is —(CH$_2$)$_2$—,

F is bond, and

G is

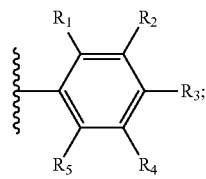

wherein R$_3$ is hydroxy or methoxy.

In other embodiments,

Ⓐ is

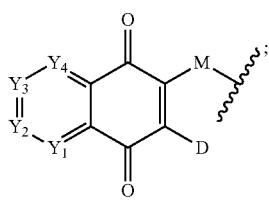

and

E, F and G are all present;

wherein F is a bond; and G is

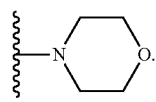 [SMILES: *N1CCOCC1]

In other embodiments,

Ⓐ is

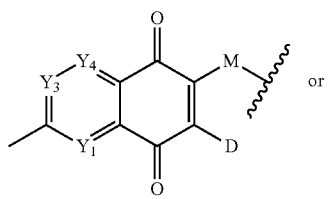

-continued

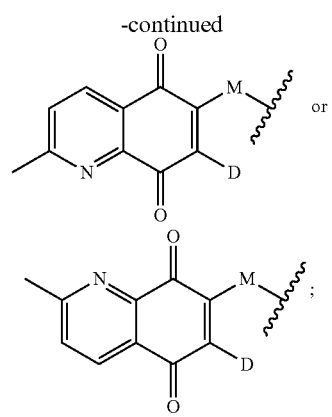

and

E, F and G are all present.

In other embodiments,

Ⓐ is

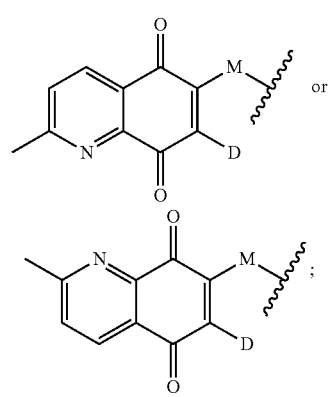

none of E, F, and G are present. In a more specific embodiment, M is a C$_1$ to C$_{10}$ alkoxy; and D is NH$_2$ in the above-described compound.

In other embodiments,

Ⓐ is

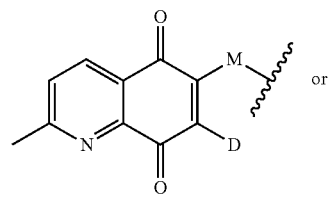

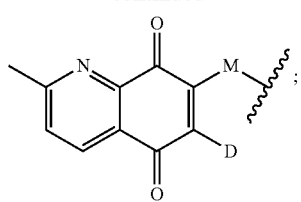
none of E, F, G are present, and M is methoxy.
In one specific embodiment,
Ⓐ is
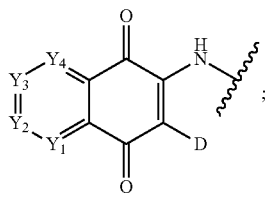
E is a C₁ to C₅ linear, branched or substitute alkylene;
F is a bond; and
G is
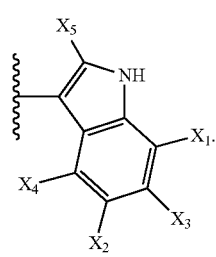
In another specific embodiment,
Ⓐ is
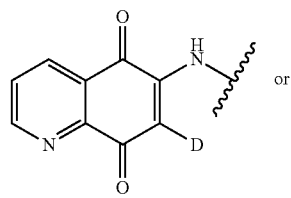 or
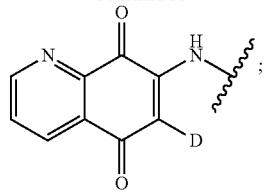
and
E is —(CH₂)₂—;
F is a bond;
G is
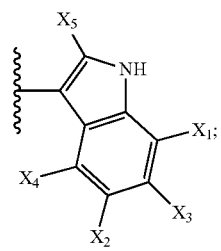
wherein $X_2$ is H, hydroxy, fluorine, methoxy or methyl.
In another embodiment,
Ⓐ is
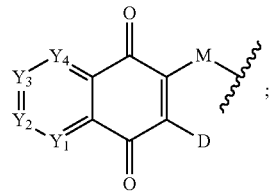
E is a C₁ to C₅ linear alkylene;
F is
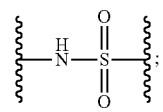
G is
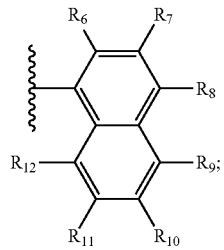
wherein $R_9$ is $NH_2$, —$N(CH_3)_2$, or $NR_{13}R_{14}$.

In specific embodiments,
is
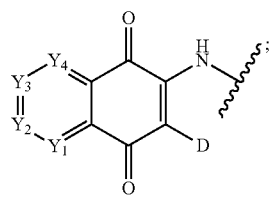
E is a $C_1$ to $C_5$ linear alkylene;
F is
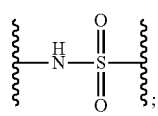 [SMILES: *NS(*)(=O)=O]
and
G is
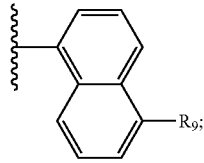
wherein $R_9$ is $NH_2$ or $NR_{13}R_{14}$.
In other embodiments,
is
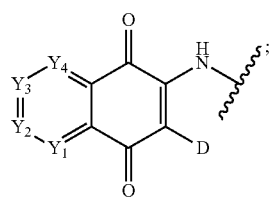
E is a $C_1$ to $C_5$ linear alkylene;
F is
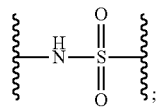
and
G is
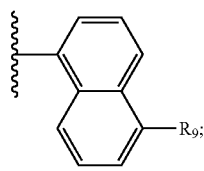
wherein D is hydrogen and $R_9$ is —$N(CH_3)_2$.
In other embodiments,
is
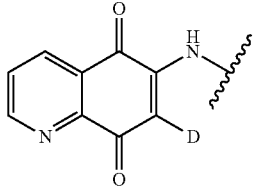 or 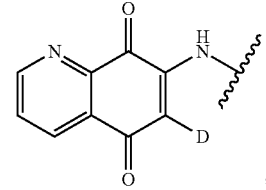 ;
E is —$(CH_2)_2$—;
F is
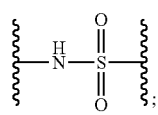
and
G is
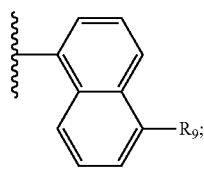
wherein $R_9$ is $NH_2$, —$N(CH_3)_2$, or $NR_{13}R_{14}$.

In other embodiments,

Ⓐ is

[chemical structure] or [chemical structure];

E is —(CH$_2$)$_2$—, or C$_1$ to C$_5$ linear alkylene;
F is a bond; and
G is

[chemical structure with R$_1$, R$_2$, R$_3$, R$_4$, R$_5$]

wherein R$_3$ is hydroxy or methoxy.

In other embodiments,

Ⓐ is

[chemical structure];

and
none of E, F and G are present.

In other embodiments,

Ⓐ is

[chemical structure] or [chemical structure];

E is —(CH$_2$)$_2$—, or C$_1$ to C$_6$ linear, branched, or cyclic alkylene;
F is a bond; and
G is

[chemical structure with R$_1$, R$_2$, R$_3$, R$_4$, R$_5$]

wherein R$^3$ is hydroxy or methoxy.

According to one embodiment,

Ⓐ is

[chemical structure], [chemical structure], or

[chemical structure];

E is —(CH$_2$)$_2$—, or C$_1$ to C$_6$ linear, branched, or cyclic alkylene;
F is a bond; and
G is

[chemical structure with R$_1$, R$_2$, R$_3$, R$_4$, R$_5$]

wherein D is hydrogen; M is —NH—; R$_1$ and R$_5$ are both hydrogen; R$_3$ is hydroxy or methoxy.

Specific embodiments of the invention encompass but are not limited to:

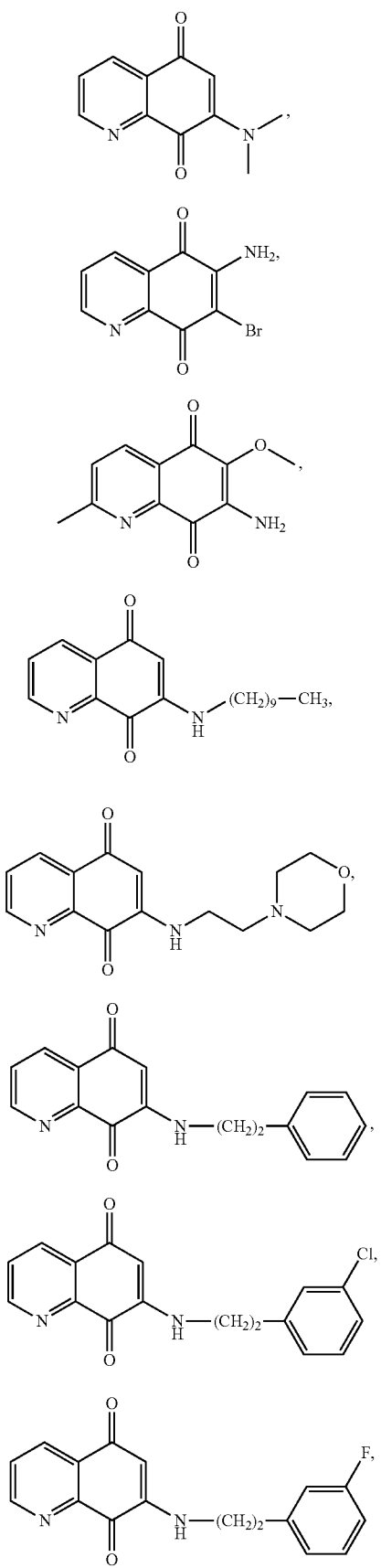
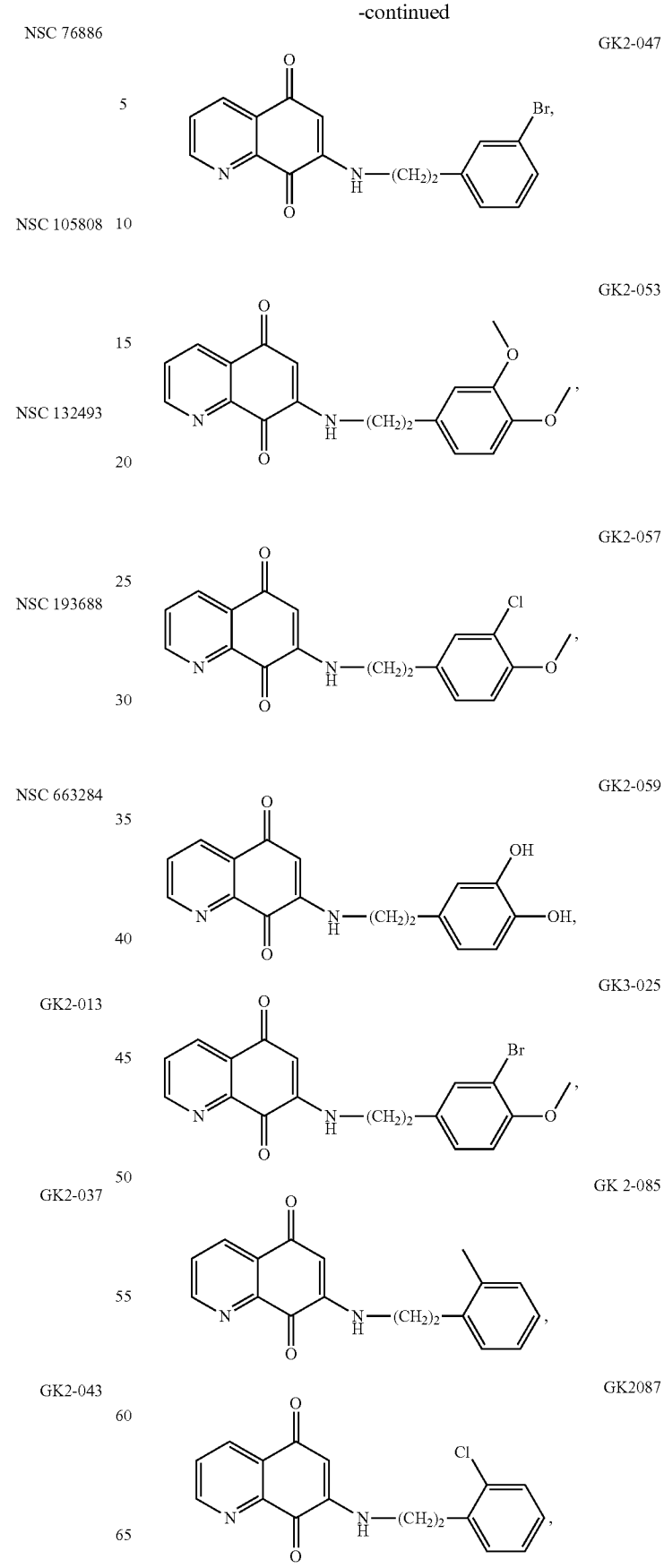

-continued
GK2-095
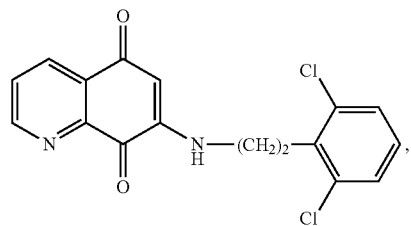
GK2-107
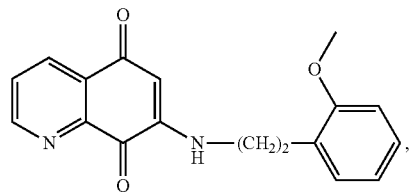
GK2-109
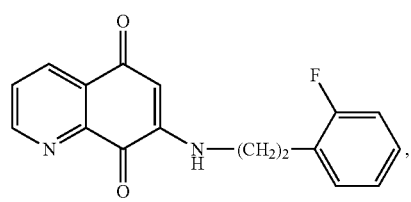
GK2-139
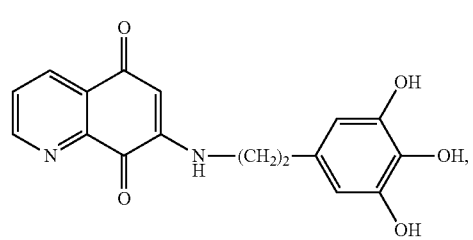
GK2-217
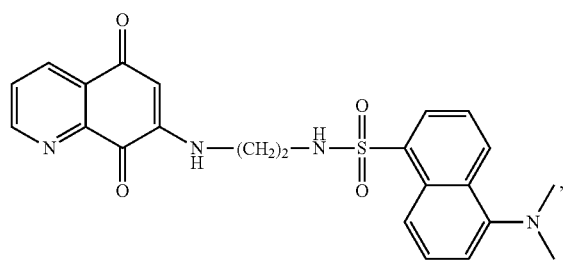
GK2-081
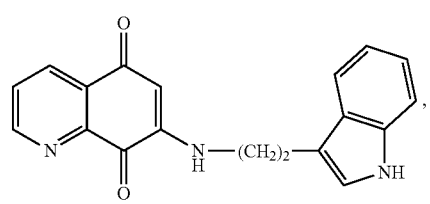
GK2-115
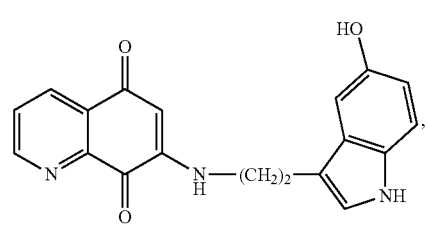
-continued
GK2-123
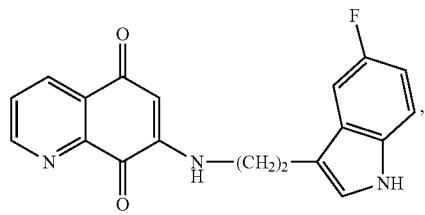
GK2-127
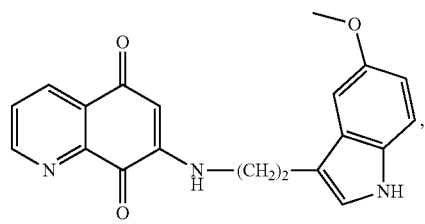
GK2-135
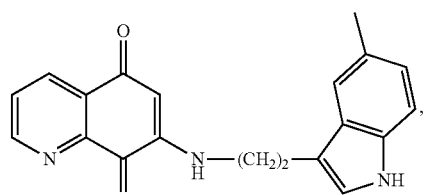
GK2-303
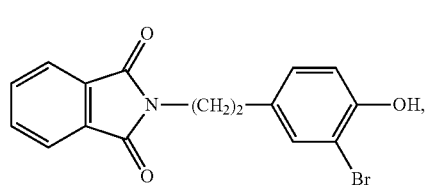
GK3-189
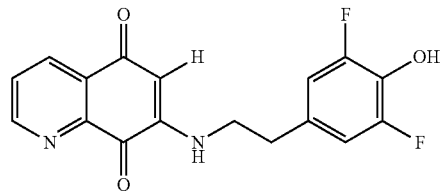
GK3-129
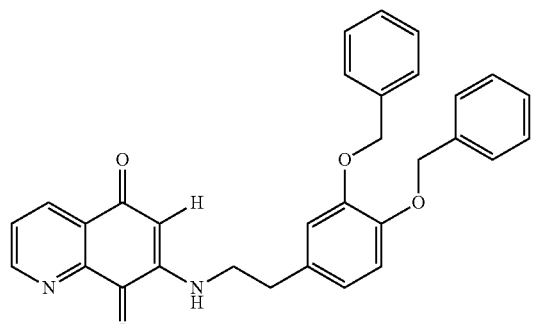
GK3-015
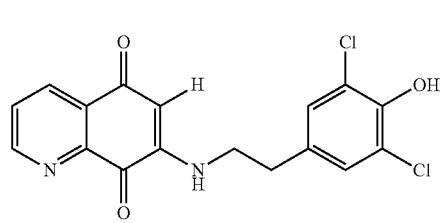

GK3-209

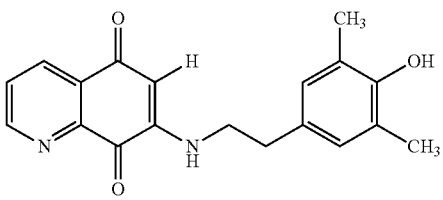

GK3-115

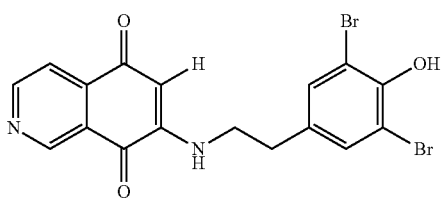

GK3-135

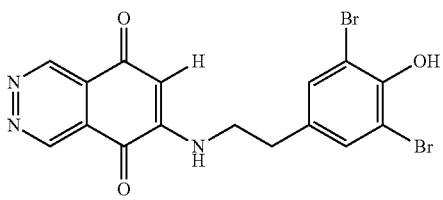

GK3-185

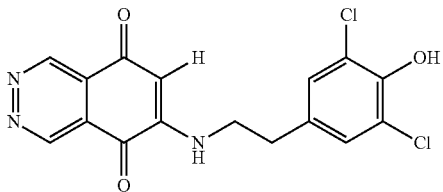

GK3-201

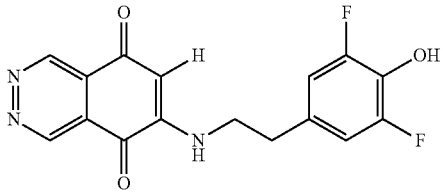

GK3-141

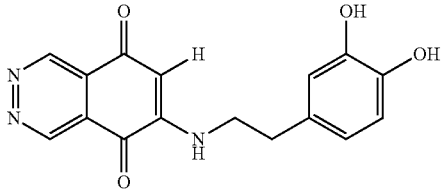

GK3-103

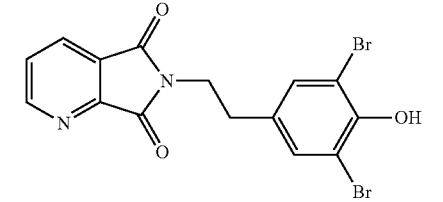

Notebook ID: GK3-103

GK3-107

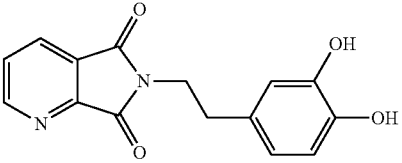

It will be understood that above compounds are illustrative only and not intended to limit the scope of the claims to only those compounds.

The compounds of the invention can be synthesized by organic chemistry techniques known to those of ordinary skill in the art.

In accordance with the invention, a composition comprising a compound of the invention or a pharmaceutically acceptable salt, is administered to a cell, such as lung cell, a breast cancer cell, a clong cancer cel, a malignant melanoma cell, an ovarian carcinoma cell, a brain tumor cell, a soft tissue sarcoma cell, and an osteosarcoma cell.

The invention also encompasses method of inhibiting the growth of a cancer cell, such as lung cancer cell, a breast cancer cell, a colon cancer cell, a malignant melanoma cell, an ovarian carcinoma cell, a brain tumor cell, a soft tissue sarcoma cell, a rhabdomyosarcoma cell, a pancreatic cancer cell, a prostate cancer cell and an osteosarcoma cell, which comprises administering to the cell a pharmaceutically effective amount of a composition comprising a compound of Formula I, or a pharmaceutically acceptable salt or prodrug thereof.

The invention also encompasses a method of reducing the likelihood of cancer metastasis, such as lung cancer metastasis, breast cancer metastasis, colon cancer metastasis, malignant melanoma metastasis, ovarian carcinoma metastasis, brain tumor metastasis, soft tissue sarcoma metastasis, rhabdomyosarcoma metastasis, pancreatic cancer metastasis, prostate cancer metastasis and osteosarcoma metastasis, which comprises administering to a subject in need of such treatment a therapeutically effective amount of a composition comprising a compound of Formula I, or a pharmaceutically acceptable salt or prodrug thereof.

In one embodiment, "treatment" or "treating" refers to an amelioration of a disease or disorder, or at least one detectable symptom thereof. In another embodiment, "treatment" or "treating" refers to an amelioration of at least one measurable physical parameter, not necessarily discernible by the patient. In yet another embodiment, "treatment" or "treating" refers to inhibiting the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, the compositions of the invention are administered to a patient, for example a human, as a preventative measure against diseases, including preventing the occurrence of a tumor or preventing the progression of a tumor.

As used herein, the term "prevent," as it relates to tumors and/or abnormal cell growth, indicates that a compound of the present invention is administered to a subject to at least partially inhibit the or reduce the likelihood of growth, division, spread, or proliferation of tumor cells. Of course, the term "prevent" also encompasses prohibiting entirely the emergence of new tumors or any of the associated symptoms from detectably appearing. Thus a subject may be "pretreated," by administering the one or more compounds of the present invention to prevent tumors from arising. The phrase "preventing the progression," as it relates to tumors, is used to mean a procedure designed to at least partially inhibit the detectable appearance of one or more additional tumors or aberrant cell growth in a patient already exhibiting one or more symptoms of the presence of a tumor or aberrant cell growth, and is also used to mean at least partially prohibiting the already-present symptoms of cancer from worsening in the subject.

As used herein, the term "administer" and "administering" are used to mean introducing at least one compound or composition into a subject. When administration is for the purpose of treatment, the substance is provided at, or after the diagnosis of an abnormal cell growth, such as a tumor. The therapeutic administration of this substance serves to inhibit cell growth of the tumor or abnormal cell growth.

As used herein, the term "coadminister" is used to mean that each of at least two compounds are administered during a time frame wherein the respective periods of biological activity overlap. Thus the term includes sequential as well as coextensive administration of the compositions of the present invention. If more than one substance is coadministered, the routes of administration of the two or more substances need not be the same. The scope of the invention is not limited by the identity of the substance which may be coadministered with the compositions of the present invention. For example, one of the compounds of the present invention may be co-administered with another compound of the present invention or another other pharmaceutically active substances, such as vinca alkaloids, nucleic acid inhibitors, platinum agents, interleukin-2, interferons, alkylating agents, antimetabolites, corticosteroids, DNA intercalating agents, anthracyclines, and ureas. Examples of specific agents in addition to those exemplified herein, include hydroxyurea, 5-fluorouracil, anthramycin, asparaginase, bleomycin, dactinomycin, dacabazine, cytarabine, busulfan, thiotepa, lomustine, mechlorehamine, cyclophosphamide, melphalan, mechlorethamine, chlorambucil, carmustine, 6-thioguanine, methotrexate, etc.

Due to the activity of the compounds of the invention, the compounds are advantageously useful in veterinary and human medicine. As described above, the compounds of the invention are useful for the treatment or prevention of conditions caused by uncontrolled cell growth, hyperproliferation of cells, tumor growth, and cancers, for example, lung cancer, pancreatic cancer, leukemia, breast cancer, liver cancer, kidney cancer, human glioblastoma and prostate cancer.

The invention provides methods of treatment and prophylaxis by administration to a subject of a therapeutically effective amount of a composition comprising a compound of the invention. The subject can be a mammal, including, but is not limited to, an animal such a cow, horse, sheep, pig, chicken, cat, dog, mouse, rat, rabbit, guinea pig, non-human primate or human.

The present compositions, which comprise one or more compounds of the invention can be administered intravenously, intravenously intramuscularly intraperitonealy and orally.

Suitable dosage ranges of the compounds of the invention, regardless of the route of administration, are generally about 0.0001 milligram to 2000 milligrams of a compound of the invention per kilogram body weight. In one specific embodiment, the dose is about 0.001 milligram to about 1500 milligrams per kilogram body weight, more specifically about 0.01 milligram to about 1000 milligrams per kilogram body weight, more specifically about 0.1 milligram to about 500 milligrams per kilogram body weight, and yet more specifically about 1 milligram to about 100 milligrams per kilogram body weight.

The compounds and the compositions of the invention may also be administered by any other route, for example, by infusion or bolus injection, by absorption through epithelial or mucocutaneous linings (e.g., oral mucosa, rectal and intestinal mucosa, etc.), and they may be administered together with another biologically active agent. Administration can be systemic or local. Various delivery systems are known, e.g., encapsulation in liposomes, microparticles, microcapsules, capsules, etc., and can be used to administer a compound or composition of the invention. In certain embodiments, more than one compound of the invention is administered to a patient. Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically. The preferred mode of administration is left to the discretion of the practitioner, and will depend in-part upon the site of the medical condition.

In specific embodiments, it may be desirable to administer one or more compounds or compositions of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as but not limited to silastic membranes, or fibers. In one embodiment, administration can be by direct injection at the site (or former site) of an atherosclerotic plaque tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and vehicles such as triglycerides.

The present compositions will contain a therapeutically effective amount of a compound of the invention, optionally more than one compound of the invention, preferably in purified form, together with a suitable amount of a pharmaceutically acceptable vehicle so as to provide the form for proper administration to the patient.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "vehicle" refers to a diluent, adjuvant, excipient, or carrier with which a compound of the invention is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents may be used. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The present compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In another embodiment, the compounds and/or compositions of the invention are formulated in accordance with routine procedures as a pharmaceutical composition adapted for intravenous administration to human beings. Typically, compounds and/or compositions of the invention for intravenous administration are solutions in sterile isotonic aqueous buffer. Where necessary, the compositions may also include a solubilizing agent. Compositions for intravenous administration may optionally include a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound of the invention is to be administered by infusion, it can be dispensed, for example, with an infusion bottle containing sterile pharmaceutical grade water or saline. Where the compound of the invention is administered by injection, an ampoule of sterile water for injection or saline can be provided so that the ingredients may be mixed prior to administration.

In one specific embodiment, the compositions of the invention can be administered orally. Formulations for oral delivery may be in the form of tablets, lozenges, aqueous or oily suspensions, granules, powders, emulsions, capsules, syrups, or elixirs, for example. Orally administered compositions may contain one or more optionally agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In one particular platform, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

The amount of a compound of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed in the compositions will also depend on the route of administration, and the seriousness of the disease or disorder, and should be decided according to the judgment of the practitioner and each patient's circumstances. In specific embodiments of the invention, the oral dose of at least one compound of the present invention is about 0.01 milligram to about 100 milligrams per kilogram body weight, or from about 0.1 milligram to about 50 milligrams per kilogram body weight, or from about 0.5 milligram to about 20 milligrams per kilogram body weight, or from about 1 milligram to about 10 milligrams per kilogram body weight.

Suitable dosage ranges for parenteral, for example, intravenous (i.v.) administration are 0.01 milligram to 100 milligrams per kilogram body weight, 0.1 milligram to 35 milligrams per kilogram body weight, and 1 milligram to 10 milligrams per kilogram body weight. Suitable dosage ranges for intranasal administration are generally about 0.01 pg/kg body weight to 1 mg/kg body weight. Suppositories generally contain 0.01 milligram to 50 milligrams of a compound of the invention per kilogram body weight and comprise active ingredient in the range of 0.5% to 10% by weight. Recommended dosages for intradermal, intramuscular, intraperitoneal, subcutaneous, epidural, sublingual, intracerebral, intravaginal, transdermal administration or administration by inhalation are in the range of 0.001 milligram to 200 milligrams per kilogram of body weight. Suitable doses of the compounds of the invention for topical administration are in the range of 0.001 milligram to 1 milligram, depending on the area to which the compound is administered. Effective doses may be extrapolated from dose-response curves derived from in vitro or animal model test systems. Such animal models and systems are well known in the art.

In other embodiments, a composition of the invention for parenteral, for example, intravenous administration includes about 0.001 milligram to about 2000 milligrams of a compound of the invention, more preferably about 0.01 milligram to about 1000 milligrams of a compound of the invention, more preferably about 0.1 milligram to about 500 milligrams of a compound of the invention, and yet more preferably about 1 milligram to about 200 milligrams of a compound of the invention.

The invention also provides pharmaceutical packs or kits comprising one or more containers filled with one or more compounds of the invention. Optionally associated with such container(s) can be a notice in the form prescribed by a governmental agency regulating the manufacture, use or sale of pharmaceuticals or biological products, which notice reflects approval by the agency of manufacture, use or sale for human administration. In a certain embodiment, the kit contains more than one compound of the invention.

The compounds of the invention can be assayed in vitro and in vivo, for the desired therapeutic or prophylactic activity, prior to use in humans. For example, in vitro assays can be used to determine whether administration of a specific compound of the invention or a combination of compounds of the invention can be used for treating a particular disorder or condition disclosed herein. The compounds of the invention may also be demonstrated to be effective and safe using animal model systems.

Other methods will be known to the skilled artisan and are within the scope of the invention.

EXAMPLES

The compounds of the invention showed pharmacological efficacy in treating or preventing various disorders.

Example 1

I. Synthetic Procedure for Novel 6- or 7-Substituted Aza- or Diazanaphthalene-5,8-Dione Scaffolds as Anti-metastatic Agents Targeting Osteosarcoma The novel 6- or 7-substituted aza- or diazanaphthalene-5,8-dione scaffolds were synthesized by the route illustrated in scheme 1. Condensation of the primary amine with the dione gives a mixture of 6- or 7-substituted adduct, which can be separated by silica gel chromatography.

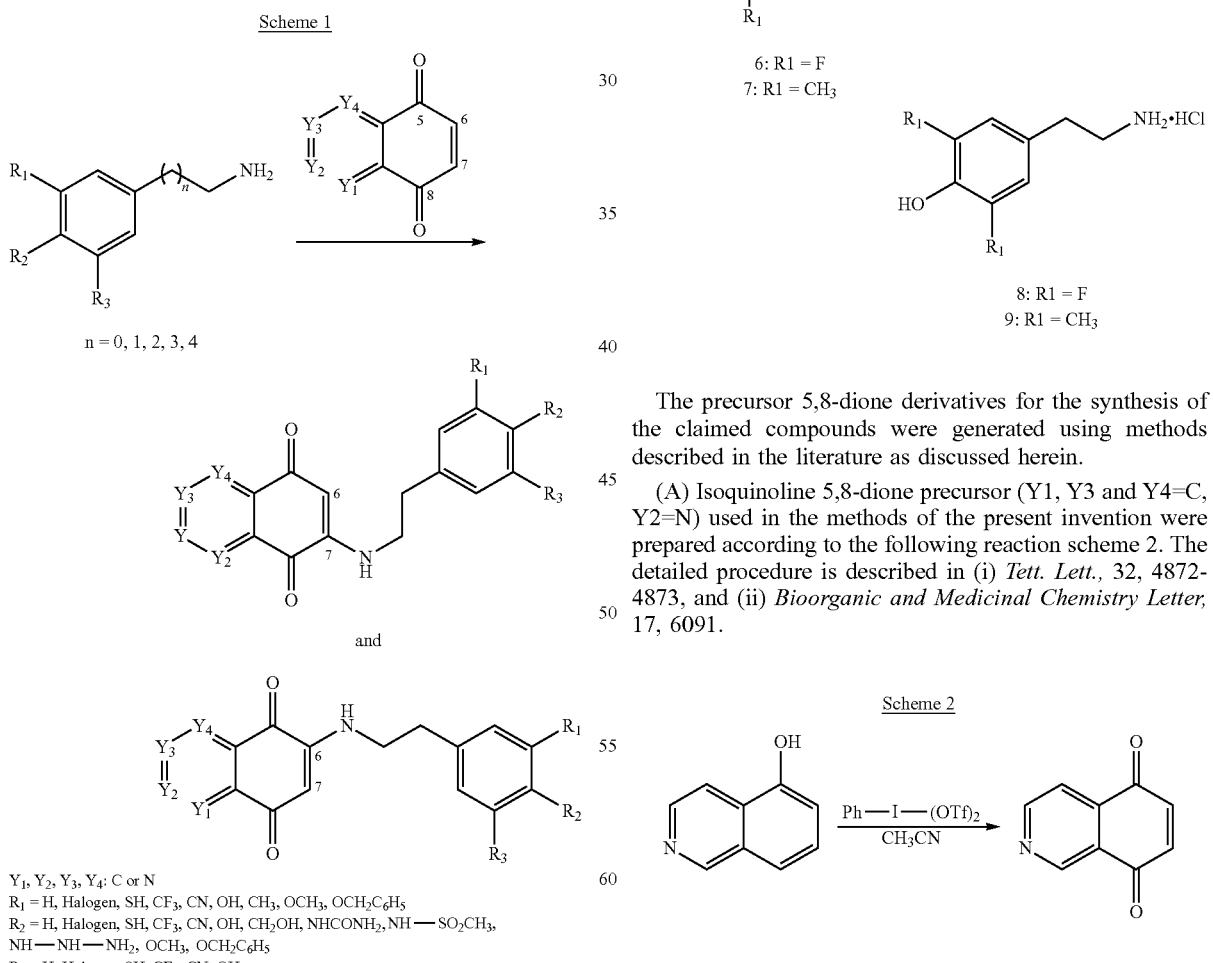

The starting material in the reaction above can be synthesized using the well-known "Henry Reaction," as disclosed in PCT Application No. PCT/US2003/026300 (Publication No. WO 2004/026305), which is incorporated by reference, as shown in Scheme 1a, below. Compounds 4 and 5 below were transformed to compounds 6 and 7 using the Henry reaction, and compounds 6 and 7 were transformed to compounds 8 and 9 using the reactions as disclosed in Kita, Y., et al., *J. Org. Chem.* 61:223-227 (1996), which is incorporated by reference.

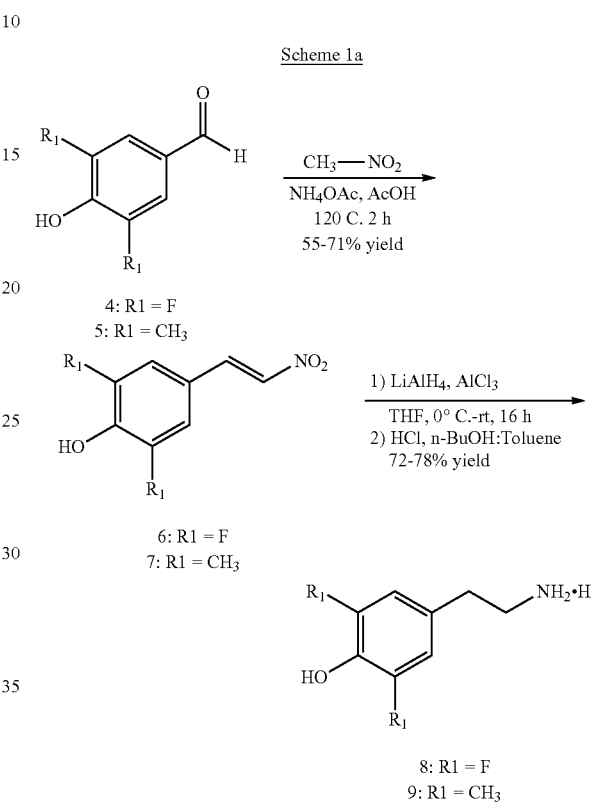

The precursor 5,8-dione derivatives for the synthesis of the claimed compounds were generated using methods described in the literature as discussed herein.

(A) Isoquinoline 5,8-dione precursor (Y1, Y3 and Y4=C, Y2=N) used in the methods of the present invention were prepared according to the following reaction scheme 2. The detailed procedure is described in (i) *Tett. Lett.*, 32, 4872-4873, and (ii) *Bioorganic and Medicinal Chemistry Letter*, 17, 6091.

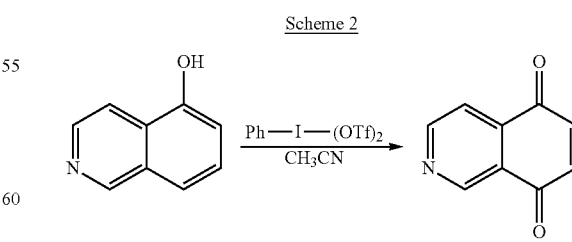

(B) Diazanaphthalene-5,8-diones precursor (Y2 and Y4=C, Y1 and Y3=N) used in the process of the present invention were prepared according to the following reaction scheme 3.

Scheme 3

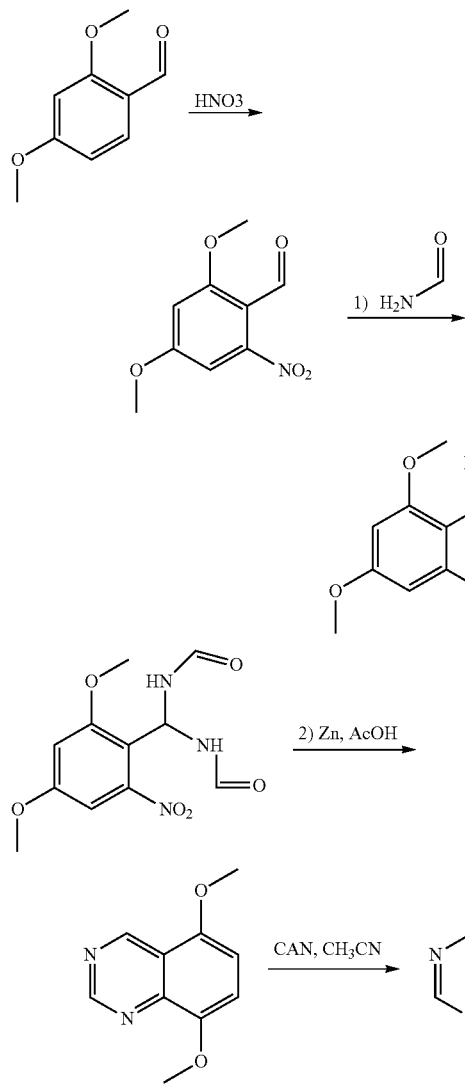

(C) Phthalazine-5,8-dione precursors (Y1 and Y4=C, Y2 and Y3=N) used in the process of the present invention were prepared according to the following reaction scheme 4. The detailed procedure is described in (i) *J. Med. Chem.*, 48, 744-752, and (ii) *Bioorganic and Medical Chemistry Letters*, 27, 2577-2580.

Scheme 4

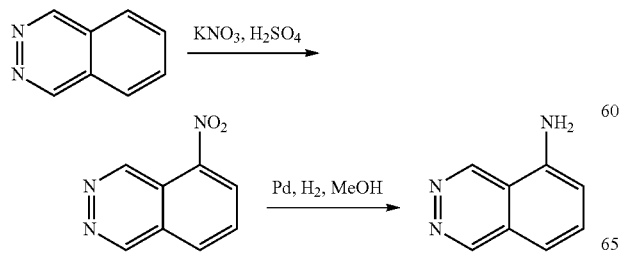

II. Synthetic Procedure for Novel Phthalimide Analogs as Anti-metastatic Agents Targeting Osteosarcoma Syntheses of the phthalimide analogs were accomplished by condensation of the primary amine with the requisite phthalic anhydride in acetic acid under microwave conditions for 1 hour. The isolated adduct was then purified by silica gel chromatography to give the product.

Scheme 5

[Reaction scheme showing condensation of substituted aryl amine with anhydride in AcOH, uWave, 160 C., 1 h]

n = 0, 1, 2, 3, 4

$Y_1, Y_2, Y_3, Y_4$ = C or N
$R^1$ = H, Halogen, SH, $CF_3$, CN, OH
$R^2$ = H, Halogen, SH, $CF_3$, CN, OH, $CH_2OH$, $NHCONH_2$, NH—$SO_2CH_3$, NH—NH—$NH_2$
$R^1$ = H, Halogen, SH, $CF_3$, CN, OH (A) The condensation of phthalic anhydride ($Y_1$=N, $Y_2$, $Y_3$ and $Y_4$=C) and the primary amine ($R_1$ and $R_3$=H, and $R_2$=OH, and n=2) of the above-described reaction is described in scheme 6.

Scheme 6

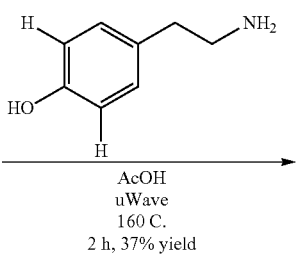

AcOH
uWave
160 C.
2 h, 37% yield

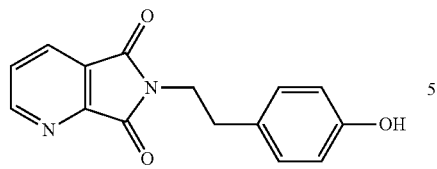

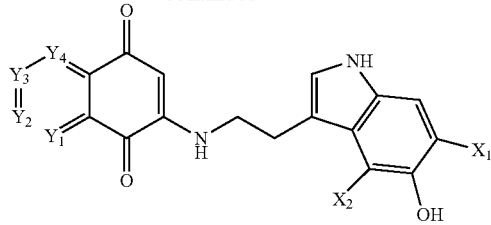

and

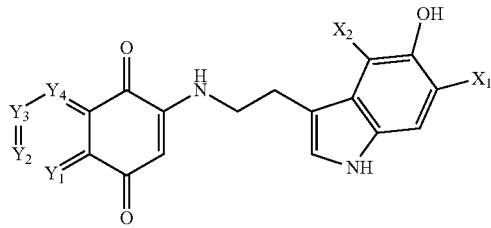

$Y_1, Y_2, Y_3, Y_4 = C$ or $N$
$X_1, X_2 = H$, Halogen, SH, $CF_3$, CN, OH (B) The condensation of phthalic anhydride ($Y_2=N$, $Y_4$, $Y_3$ and $Y_4=C$) and the primary amine ($R_1$ and $R_3=H$, and $R_2=OH$, and n=2) of the above-described reaction is described in scheme 7.

Synthesis of the precursor tryptamine analogs were accomplished according to the following reaction scheme 9. The detailed procedure is described in (i) *J. Med. Chem.*, 22, 63-69, and (ii) *J. Fluorine Chemistry*, 97, 161-164.

Scheme 7

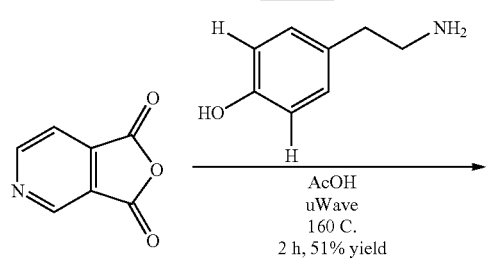

Scheme 9

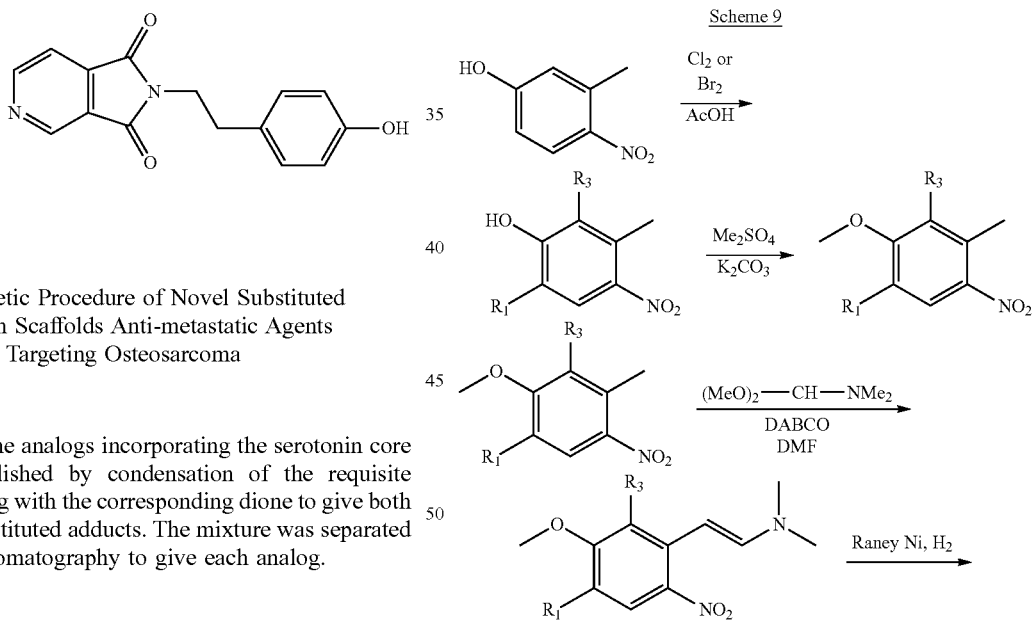

III. Synthetic Procedure of Novel Substituted Serotonin Scaffolds Anti-metastatic Agents Targeting Osteosarcoma Synthesis of the analogs incorporating the serotonin core can be accomplished by condensation of the requisite tryptamine analog with the corresponding dione to give both the 6- and 7-substituted adducts. The mixture was separated by silica gel chromatography to give each analog.

Scheme 8

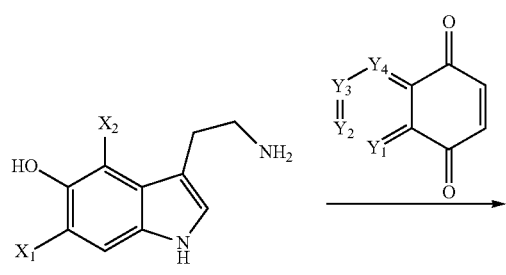

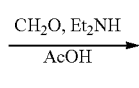

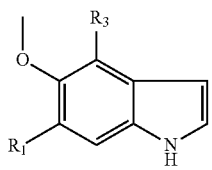

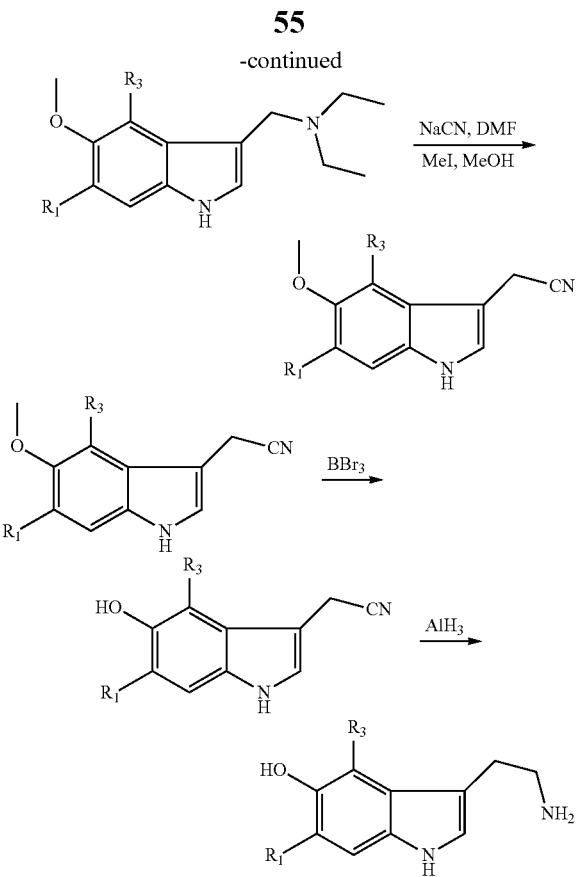

IV. Synthetic Procedure of Novel 3,4,5-trisubstituted benzylamino and benzamido Scaffolds 3,4,5-trisubstituted benzylamino and benzamido scaffolds used in the process of the present invention were prepared according to the following reaction scheme 10. The detailed procedure is described in (i) U.S. Pat. No. 5,283,336 and (ii) *J. Med. Chem.*, 50, 3497.

Scheme 10

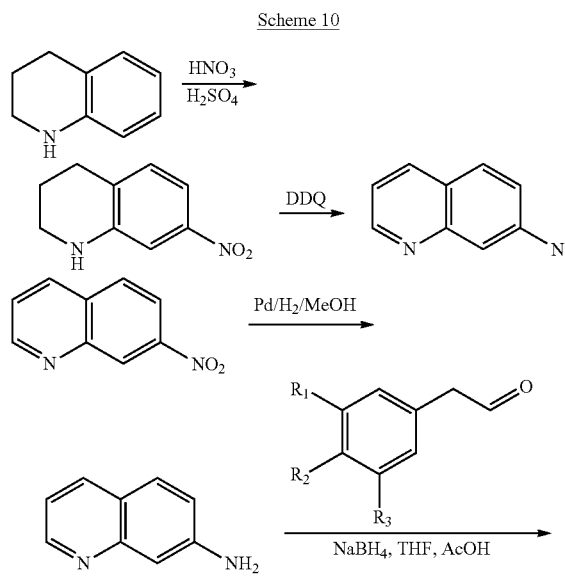

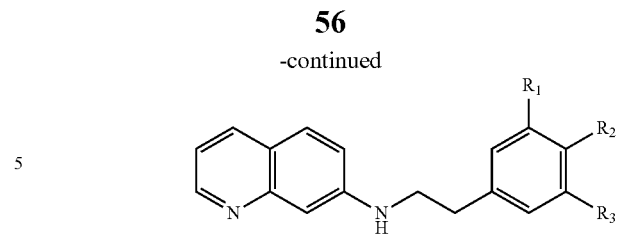

$R_1$ = H, Halogen, SH, $CF_3$, CN, OH
$R_2$ = H, Halogen, SH, $CF_3$, CN, OH, $CH_2OH$, $NHCONH_2$, NH—$SO_2CH_3$, NH—NH—$NH_2$
$R_3$ = H, Halogen, SH, $CF_3$, CN, OH

V. Synthetic Procedure of Chloro Derivatives

Chloro derivatices of the present invention were prepared according to the following reaction scheme 11. The detailed procedure is described in *J. Organic Chemistry*, 9, 359-372.

Scheme 11

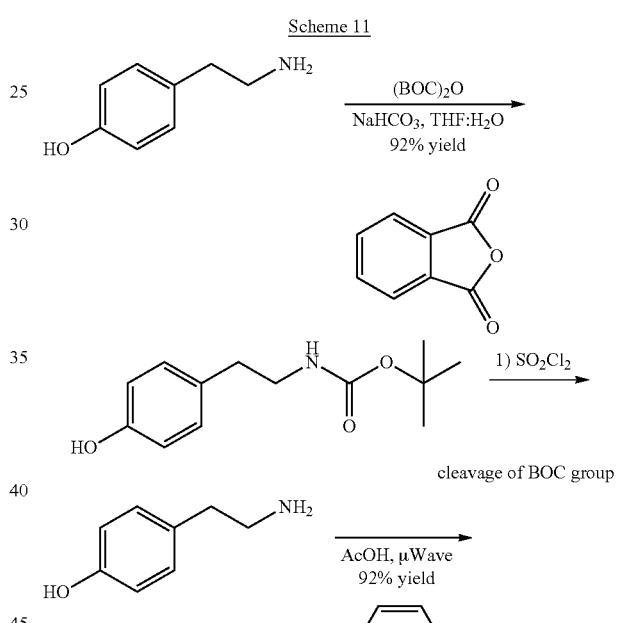

VI. Synthetic Procedure of GK3-015

GK3-015 was prepared according to the following reaction scheme 12.

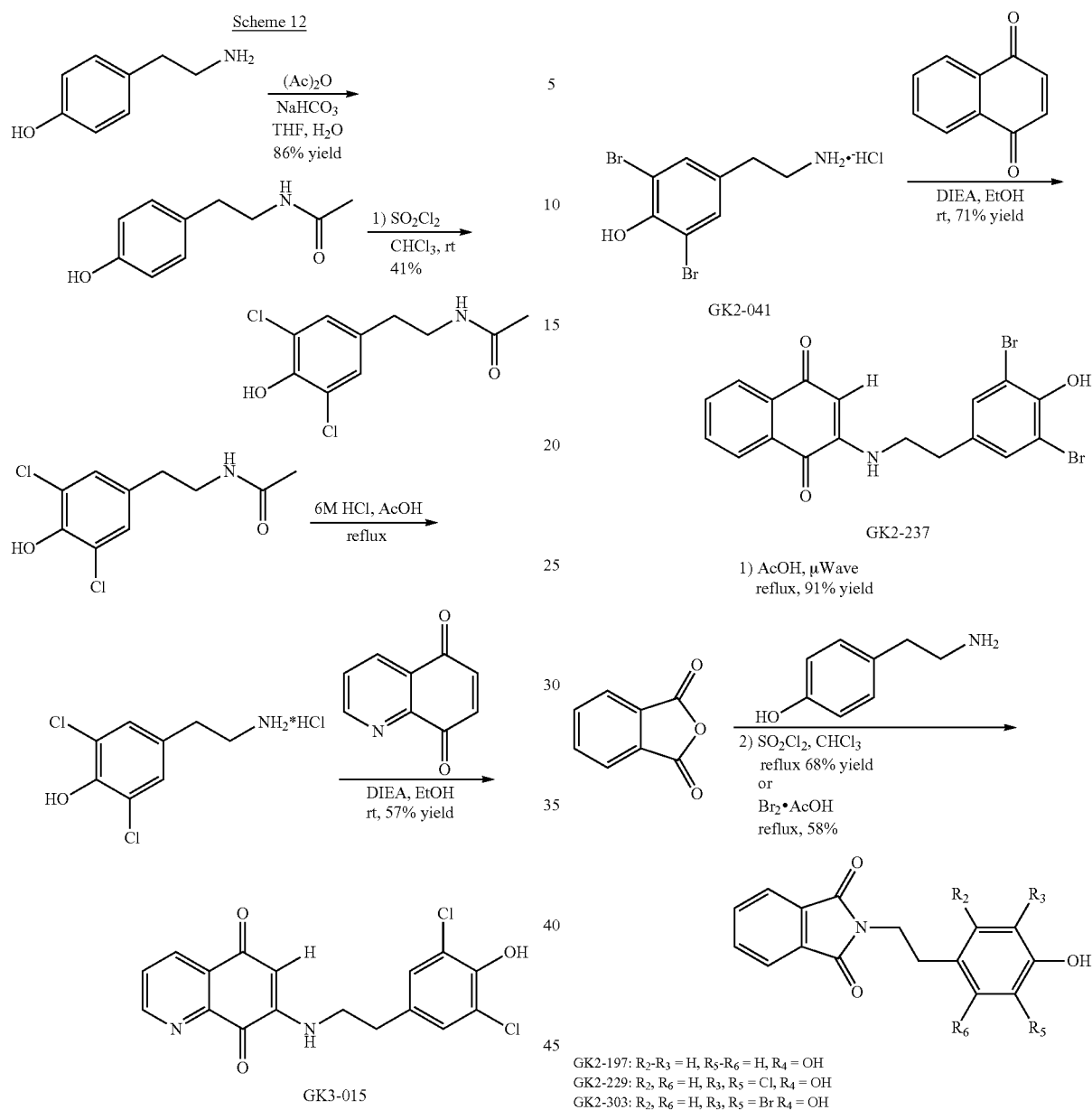
VII. Synthetic Procedures of GK2-197, GK2-229, GK2-303
GK2-197, GK2-229, GK2-303 were prepared according to the following reaction in scheme 13.
VIII. Synthetic Procedure of the 7-aminoquinoline
7-aminoquinoline was prepared according to the following reaction in scheme 14.
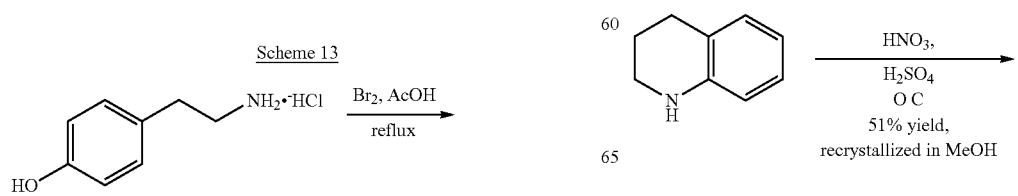

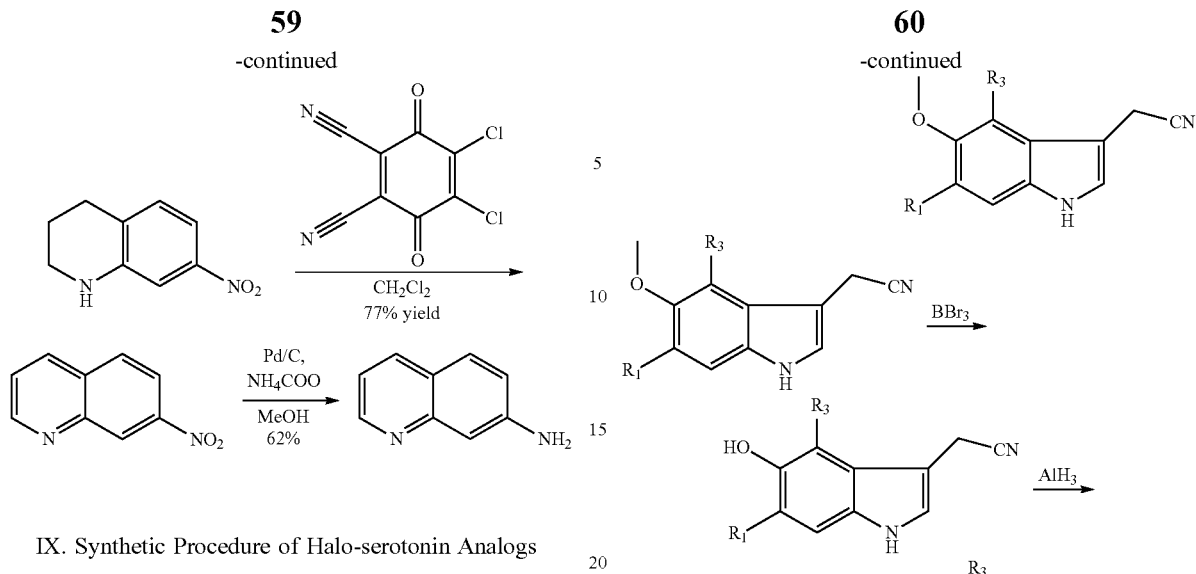

IX. Synthetic Procedure of Halo-serotonin Analogs

Halo-serotonin analogs were prepared according to the following reaction in scheme 15.

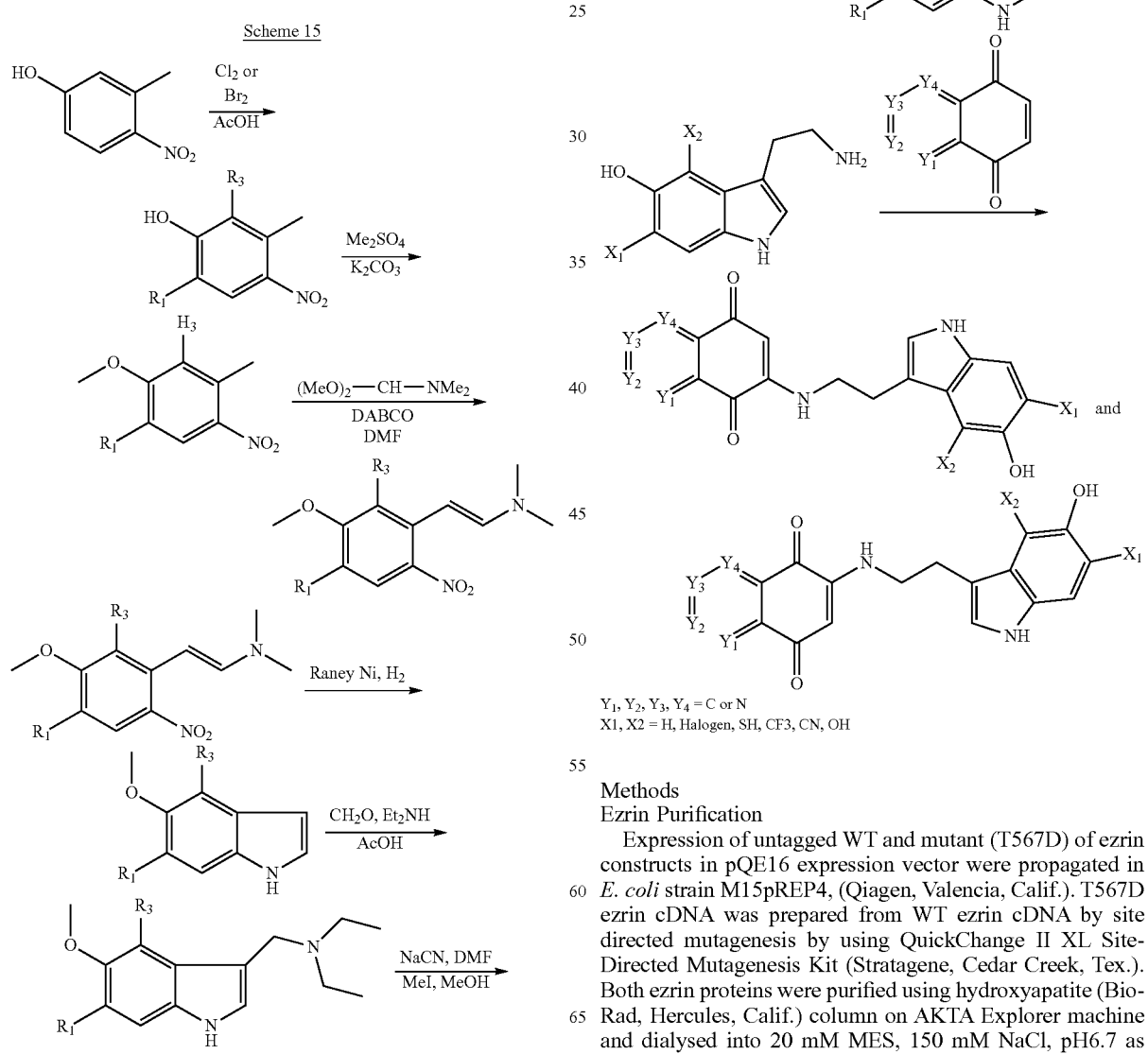

$Y_1, Y_2, Y_3, Y_4 = C$ or $N$
$X_1, X_2 = H$, Halogen, SH, CF3, CN, OH

Methods
Ezrin Purification

Expression of untagged WT and mutant (T567D) of ezrin constructs in pQE16 expression vector were propagated in *E. coli* strain M15pREP4, (Qiagen, Valencia, Calif.). T567D ezrin cDNA was prepared from WT ezrin cDNA by site directed mutagenesis by using QuickChange II XL Site-Directed Mutagenesis Kit (Stratagene, Cedar Creek, Tex.). Both ezrin proteins were purified using hydroxyapatite (Bio-Rad, Hercules, Calif.) column on AKTA Explorer machine and dialysed into 20 mM MES, 150 mM NaCl, pH6.7 as described previously (Reczek, D., et al., *J. Cell Biol.* 139, 169-179 (1997)). Protein purity was estimated based on absence of nonspecific bands on coomassie stained gels.

Immunoprecipitation

For analysis of actin binding to FL and mutant ezrin, K12 cell lysate was incubated with recombinant ezrin protein, then subjected to immunoprecipitation with ezrin antibody (Sigma, St. Louis, Mo.) and immunoblotted with actin antibody (Santa Cruz, Santa Cruz, Calif.). For analysis of inhibition of small molecules on ezrin phosphorylation and actin binding, K7M2 cell lysates were treated with compounds at 10 µM concentration for 6 hours, followed by immunoprecipitation with the ezrin antibody and immunoblotted with phospho-ezrin (Cell Signaling, Danvers, Mass.), actin and ezrin antibodies.

In vitro Kinase Assays 500 ng of recombinant ezrin protein in kinase assay mix (200 µM ATP) was incubated with the compounds at 1-100 µM concentrations for 15 minutes on ice, then 50 ng PKC,τ (Millipore, Billerica, Mass.) was added. Reaction was performed at 30° C. for 30 min and stopped by adding 2× sample buffer. NSC305787 and NSC668394 profiling on PKC, τ, α and γ were performed by utilizing the Kinase Inhibitor Compound Profiling Service at Kinexus Bioinformatics Corporation (Vancouver, Calif.).

Surface Plasmon Resonance (SPR)

Compounds for initial screening were acquired from 4 libraries (Challenge Set, Diversity Set, Mechanistic Set and Natural Product Set) of the Developmental Therapeutics Program, National Cancer Institute. Their direct ezrin binding potential was analyzed by using Biacore T100 v2.0.3 instrument (GE Healthcare, Piscataway N.J.). The technique requires immobilization of the ligand on sensorchip and the analyte is then injected over the chip surface through a fluidics system. Existing interactions are measured based on total mass change on the chip surface. Recombinant WT ezrin protein was used as the ligand and immobilized on to a Biacore CM5 sensorchip and compounds were injected one at a time as the binding interactions were recorded. HBS-P, which contained 10 mM Hepes (pH 7.4), 150 mM NaCl and 0.05% surfactant P-20 was used as the standard running buffer. At initial screening, each molecule was injected for 1 min at 10 or 100 µM concentrations. Any molecule giving more than 10 resonance units (RU) binding signal with an acceptable curve shape was selected as an initial hit. During detailed SPR analysis, NSC305787 was injected at 1 µM, 2 µM, 4 µM, 8 µM, 32 µM and 64 µM concentrations in duplicates. NSC668394 was injected at 1.5 µM, 3 µM, 6 µM, 12.5 µM, 25 µM, 50 µM and 100 µM concentrations in triplicates. Results were analyzed by using Biacore T-100 v2.0.3 analysis software.

Chemotaxis, Cell Viability Assays

Chemotaxis experiments were performed in 96 well Boyden chamber as described previously (Chen, K., et al., Pediatr. Blood Cancer, 51, 349-355 (2008)). To measure effect of compounds on cellular toxicity, WST viability assay (Roche, Indianapolis, Ind.) was performed in parallel to chemotaxis experiments.

Invasion Assays

The anti-invasive potential of NSC305787 and NSC668394 were evaluated by using electric cell impedance sensing (ECIS) on a Roche xCELLigence system (Roche, Indianapolis, Ind.). Briefly, HUVEC cells (25,000/well) were seeded in a 96-well plate in EGM-2 media (Lonza, Basel, CH). Following formation of a confluent HUVEC monolayer (app 32 hrs), EGM-2 media was aspirated and a layer of OS cells (10,000 cells/well) was added in DMEM media containing the compounds. This time point was accepted as 0 hr of treatment and invasion was monitored during the following 6 hrs by measuring changes in resistance at the cell-electrode interphase.

Zebrafish Embryo Development Assay

Animals. Zebrafish (Danio rerio) were raised, maintained and crossed as described before (Westerfield, M. University of Oregon Press, Eugene. Or., 1993). Development of embryos was studied at 28° C. and staging was determined by morphological characteristics (Kimmel, C. B., et al., Dev. Dyn. 203, 253-310 (1995)).

Morpholino Oligonucleotide Injections.

A translation blocking anti-ezrin morpholino oligonucleotide (MO), described and validated by Link et al. (Link, V., et al., J. Cell Sci., 119, 2073-2083 (2006)), MO1, 5'-CGC-GAACATTTACTGGTTTAGG (SEQ ID NO:1), was synthesized by Gene-Tools, LCC (Philomath, Oreg.). MOs were microinjected into one to four cell stage embryos.

Chemical Screening.

Zebrafish embryos were arrayed, three per well, in 96-well plates. Compounds were added at 1-33 µM concentrations. Embryos were observed, and photographed, at 70% epiboly, 24-28 hours post fertilization (hpf) and 48 hpf.

Pulmonary Metastasis Assay (PuMA)

The technique of isolated lung organ culture was performed as reported by Mendoza et al (Mendoza, A., et al., J. Clin. Invest., 120(8):2979-2988 (2010)).

In vivo Experimental Metastasis Model

GFP expressing K7M2 or MNNG tumor cells ($1 \times 10^6$) were delivered by tail vein to nude mice. One day after injection, vehicle, NSC305787 (240 µg/kg/inj) and NSC 608394 (226 µg/kg/inj) were injected 5 days a week intraperitoneally.

Statistical Analysis

Statistical analyses were performed with Prism (Graph-Pad Software, LaJolla, Calif.).

Results

Initial Screening of Small Molecules for Direct Binding to Ezrin

Small molecule libraries were screened to identify compounds that directly bind to ezrin protein. To achieve this goal, full-length recombinant ezrin protein was expressed in bacteria and the protein was purified by column chromatography as described earlier (Reczek, D., et al., J. Cell Biol., 139, 169-179 (1997)). Recombinant full length ezrin was prepared to a concentration of 100 µg/ml with >90% purity (FIG. 1a). To validate that recombinant mouse ezrin protein purified from bacteria has the appropriate tertiary structure, its actin binding ability was evaluated. Phosphorylation of threonine at position 567 provides an open conformation of ezrin and increases its actin binding capacity. A threonine (T) to aspartic acid (D) substitution was used to mimic phosphorylation in this residue (Gautreau, A., et al., J. Cell Biol., 150, 193-203 (2000)). Wild type (WT) and phosphomimicking mutant (T567D) of recombinant ezrin protein were purified (FIG. 1a). Actin binding of these two constructs was evaluated by immunoprecipitation. Cell lysates from low ezrin expressing K12 osteosarcoma cells were incubated with recombinant ezrin proteins. Cellular actin protein co-immunoprecipitated was detected by immunoblotting. Significantly higher levels of actin binding to the T567D mutant were detected compared to WT ezrin (FIG. 1b). Increased binding of T567D ezrin to purified actin was also demonstrated in an ELISA assay (data not shown). These results suggested that at least a portion of recombinant ezrin made in bacteria was folded properly to replicate expected mammalian structure.

Figure 1E:
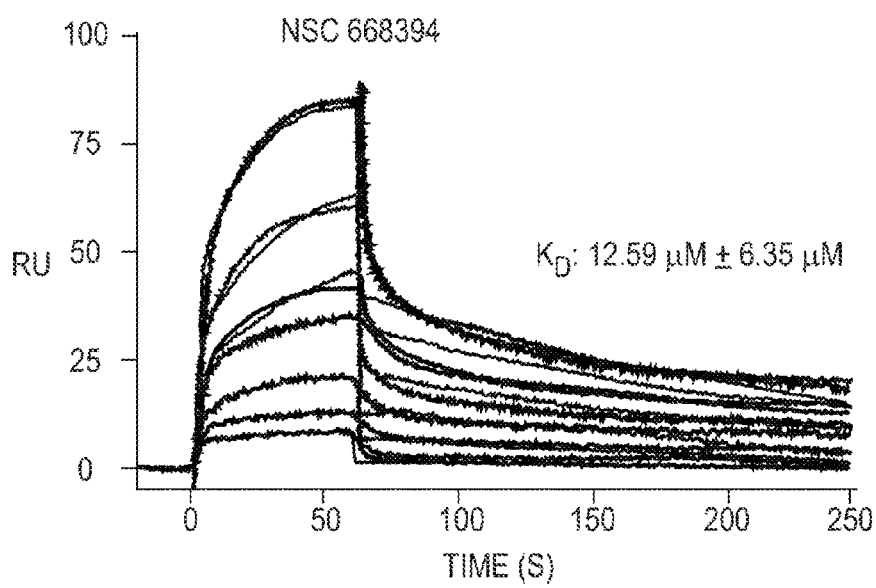

Surface plasmon resonance (SPR) allows measurement of direct molecular interactions in real-time and in a label free setting (Fivash, M., et al., *Curr. Opin. Biotechnol.*, 9, 97-101 (1998); Malmqvist, M., et al., *Biochem Soc Trans.*, 27, 335-340 (1999)). SDR to screen small molecule libraries for compounds that directly bind to recombinant WT ezrin protein. Ezrin was immobilized on Biacore T100 sensorchips and small molecules were injected over the surface one at a time at a single concentration (10 µM or 100 µM). Four libraries for screening (Challenge Set, Diversity Set, Mechanistic Set and Natural Product Set) were provided by Developmental Therapeutics Program of the National Cancer Institute. At this initial screen any molecule that showed meaningful binding to recombinant ezrin over the background values was selected as a primary hit. The 65 primary hits were evaluated with functional assays, which identified two lead compounds, NSC305787 and NSC668394 (FIG. 1c). These two compounds were used to develop and generate the novel compounds disclosed herein. Detailed SPR analysis of the two lead compounds in 5 independent experiments yielded an average KD of 5.85 µM (±s.d. 3.85 µM) for the affinity of NSC305787 (FIG. 1d) and 12.59 µM (±s.d. 6.35 µM) for the affinity of NSC668394 (FIG. 1e) binding to ezrin. $K_D$ values of NSC305787 and NSC668394 binding to actin, which was used as a negative control were 91.4 µM and 603 µM, respectively (data not shown). None of the 65 primary hits showed differential binding between WT and T567D mutant ezrin proteins.

The secondary functional assays used for lead compound selection included ezrin phosphorylation, actin binding, chemotaxis, zebrafish embryonic development and mouse lung organ culture. Furthermore, drugability based on their solubility, potential in vivo toxicity, chemical stability and potential for derivatization were also considered for elimination of some primary hits.

NSC305787 and NSC668394 Inhibit Endogenous Ezrin T567 Phosphorylation and Actin Binding.

Figure 2A:
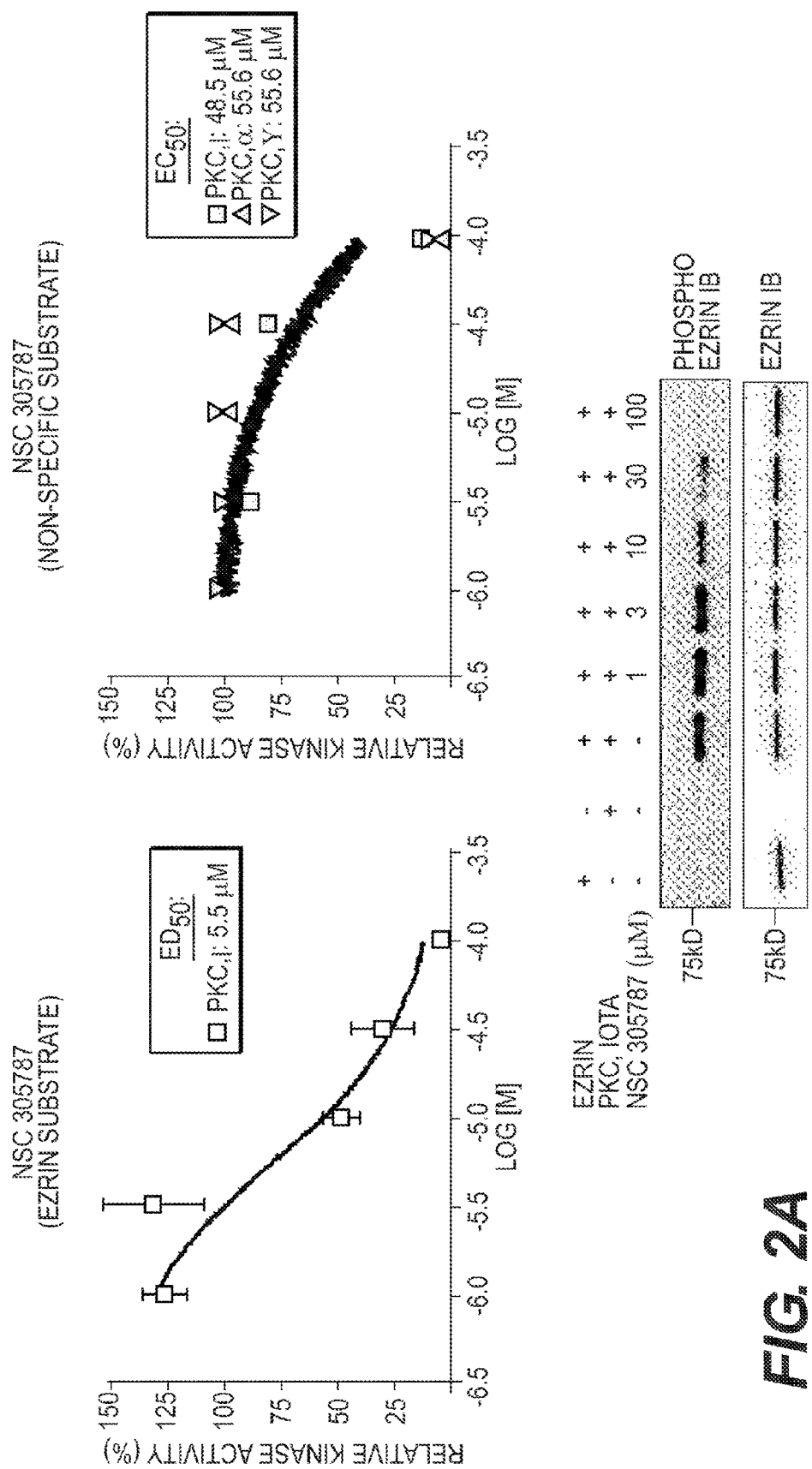
FIG. 2 illustrates NSC305787 and NSC668394 inhibit ezrin T567 phosphorylation. (A) K7M2 metastatic OS cell line was treated with NSC305787 (10 µM) and NSC668394 (10 µM) for 6 hours. NSC305787 and NSC668394 inhibited phosphorylation of endogenous ezrin protein and its interaction with actin without altering cellular ezrin protein levels (B and C). The effect of NSC305787 and NSC668394 on recombinant ezrin phosphorylation by recombinant PKC, was tested in an in vitro kinase assay. Phoshorylation of ezrin was detected by a phosphospecific antibody following PAGE and immunoblotting. Experiments were repeated three times and densitometric analysis of bands was used for calculation of % inhibition (graphs). Error bars represents s.d. from three independent experiments. Kinase activities of PKC,τ, PKC,α and PKC,γ were also evaluated with a nonspecific substrate in the presence of NSC305787 and NSC668394 by a radioactive in vitro kinase assay. Data analysis was done by using a sigmoidal dose-response equation where log $EC_{50}$ for each curve with the ezrin substrate and the non-specific substrate were compared to each other (P=0.0118 for NSC305787 and P=0.0084 for NSC668394).

Ezrin phosphorylation at T567 is critical for its activation, which then enables interaction of ezrin with other cellular proteins including actin (Matsui, T., et al., *J. Cell Biol.*, 140, 647-657 (1998)). Both NSC305787 and NSC668394 inhibited T567 phosphorylation and actin binding of ezrin at 10 µM concentration in K7M2 OS cells. Treatment with the compounds did not alter cellular ezrin protein levels (FIG. 2a).

Kinase Independent Inhibition of Ezrin T567 Phosphorylation by PKC, by Directly Targeting the Substrate.

Figure 2B:
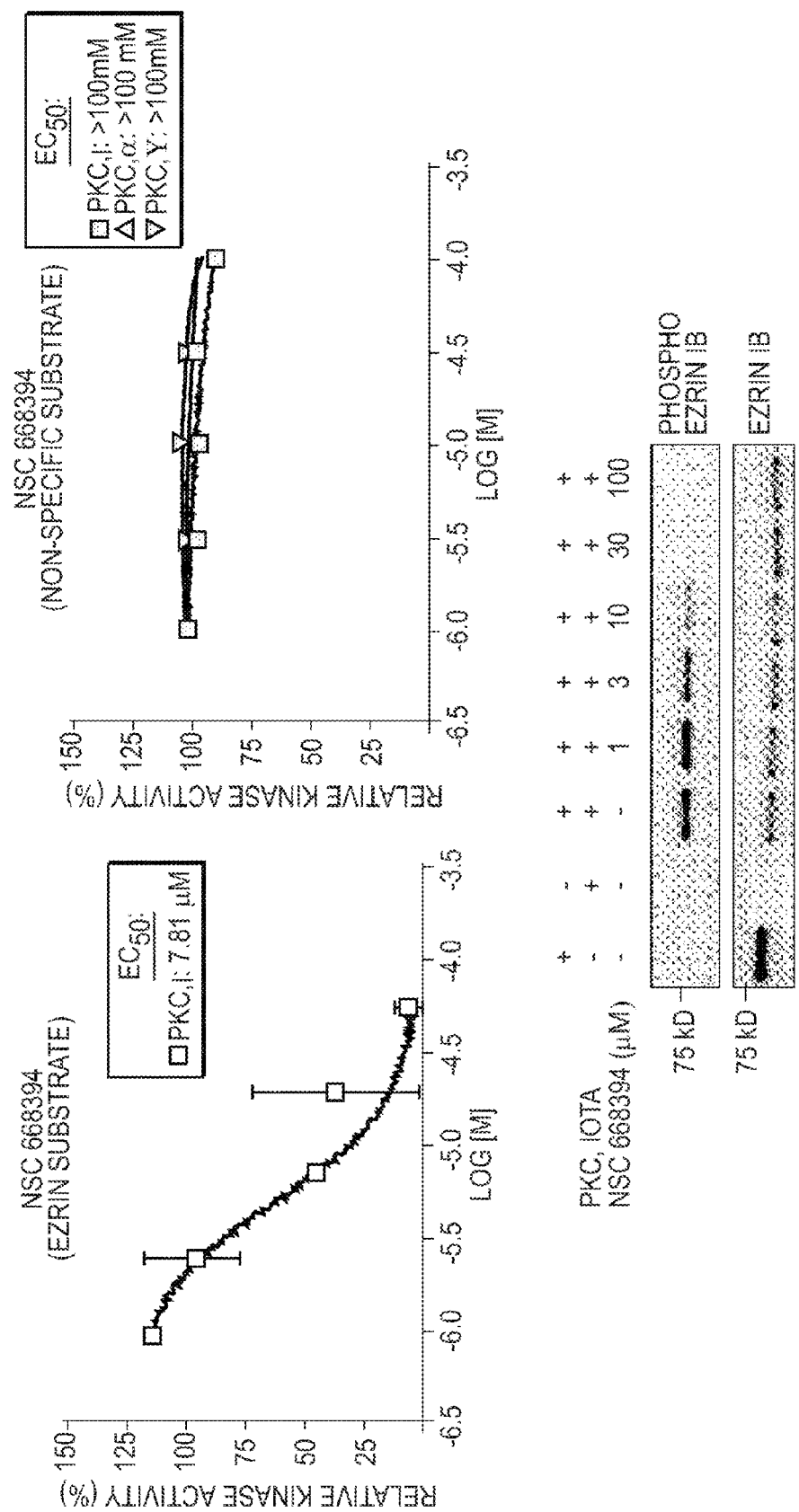
Figure 2C:
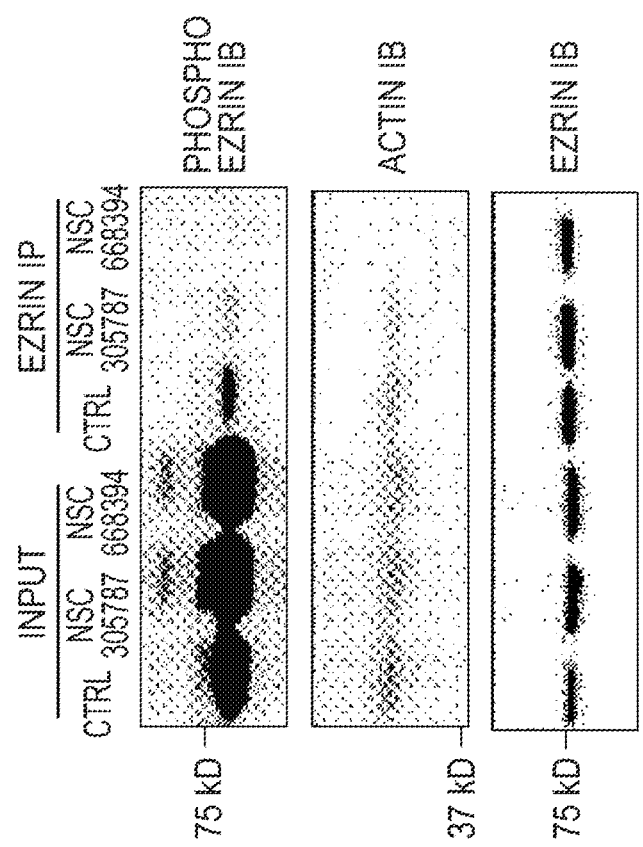

Dynamic regulation of ezrin phosphorylation during metastatic progression is linked to protein kinase C(PKC) activation. Members of this family of serine/threonine kinases that phosphorylate ezrin at T567 in OS cells include PKC, alpha (α), iota (τ) and gamma (γ) (Ren, L., et al., *Oncogene*, 28, 792-802 (2009)). Phosphorylation of ezrin by PKC,τ. was inhibited by NSC305787 with an $IC_{50}$ of 5.5 µM and by NSC668394 with an $IC_{50}$ of 7.81 µM (FIG. 2b,c). To determine whether reduced phosphorylation of ezrin resulted from inhibition of the kinase, the effect of lead compounds on three PKC isoforms (PKC,τ, PKC,α. and PKC,γ) with a nonspecific substrate was tested. NSC305787 required 10-fold higher concentration (~50 µM) to inhibit all three PKC isoforms than that required to inhibit ezrin phosphorylation (FIG. 2b). NSC668394 did not show any significant inhibition of PKC activity with the doses tested in this experiment (maximum 100 µM) (FIG. 2c).

Furthermore, direct interaction experiments with Biacore in SPR analysis revealed that NSC668394 bound to PKC,τ with a $K_D$ of 160.2 µM and NSC305787 bound to PKC,τ with a $K_D$ of 172.4 µM (data not shown). These results strongly suggest that NSC305787 and NSC668394 inhibit ezrin T567 phosphorylation primarily due to their binding to ezrin and not due to inhibition of PKC,τ kinase activity.

OS Cell's Invasive Phenotype is Inhibited by NSC305787 and NSC668394

Figure 3A:
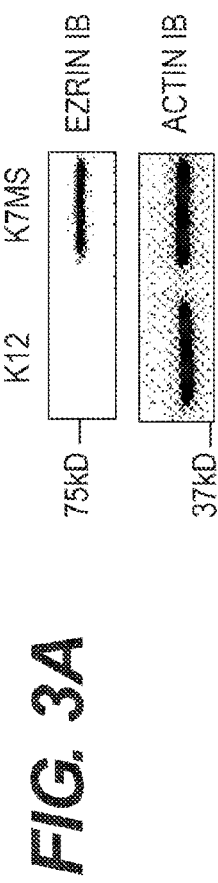
FIG. 3 illustrates NSC305787 and NSC668394 inhibit ezrin mediated invasion of OS cells. (A) Endogenous ezrin protein levels in K12 and K7M2 cells are shown. Equal loading is determined by blotting with an actin antibody. Both NSC305787 (B) and NSC668394 (C) at 1 µM and 10 µM concentrations inhibited invasion of K7M2 cells through a HUVEC monolayer when compared to the control (1% DMSO). NSC305787 did not inhibit invasion of less metastatic K12 cells at both concentrations. NSC668394 also did not inhibit invasion by these cells at 1 µM, but a slight inhibition was observed at 10 µM treatment. Error bars represent standard deviation from duplicate data points. The experiments were performed in duplicates. Cell index is a measurement parameter with no units. In this assay a decrease in cell index represents invasion of HUVEC layer by OS cells. It is measured according to the following formula: Cell index=((Rt−R0)/F where, Rt is resistance at time point t, R0 is background resistance (measured with media alone, no cells), and F is frequency at which measurement is taken (10 kHz).
Figure 3B:
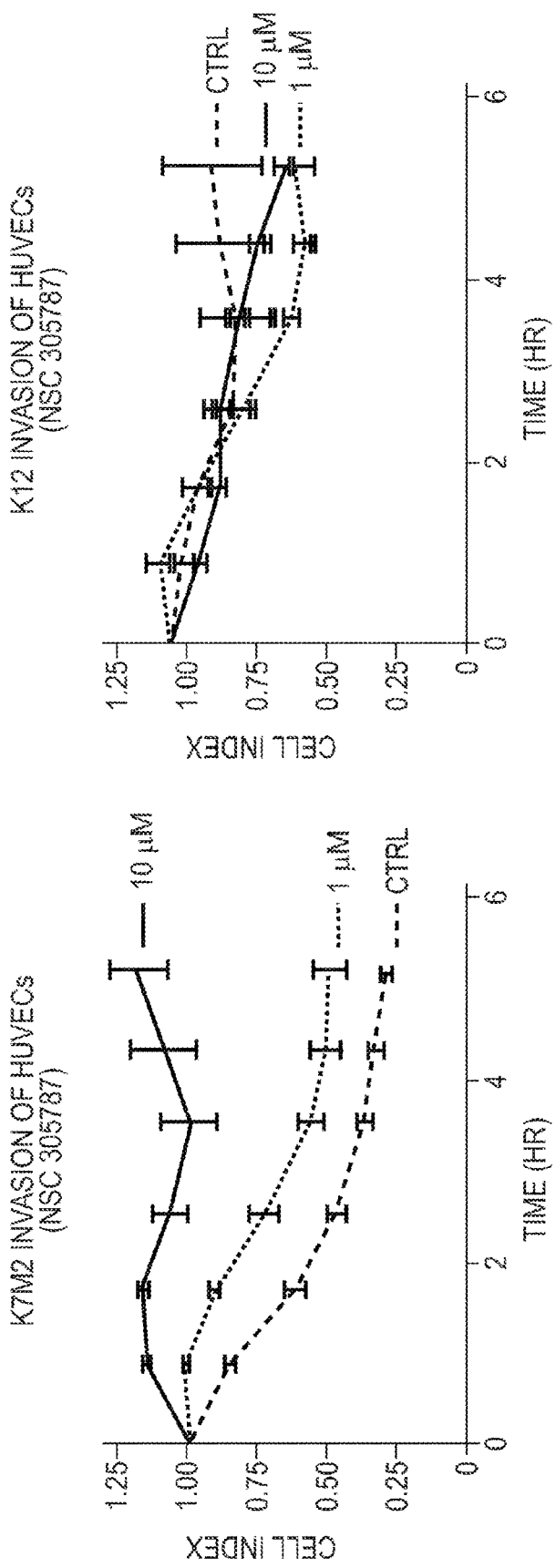
Figure 3C:
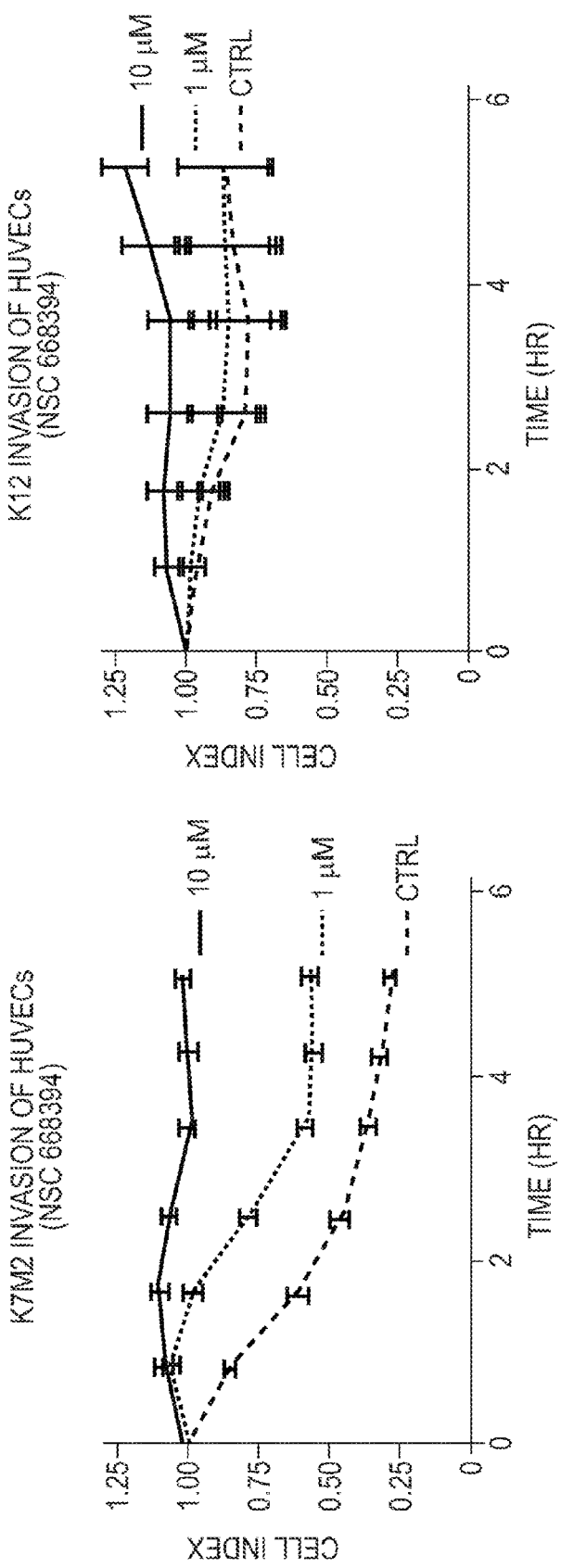

Higher levels of ezrin protein in K7M2 cells compared to K12 cells leads to enhanced metastatic potential of K7M2 cells (FIG. 3a) (Khanna, C., et al., *Cancer Res.*, 61, 3750-3759 (2001)). All 65 initial hits were tested for inhibiting cell motility of both cell lines in a modified Boyden chamber chemotaxis assay. Any molecule that inhibited chemotaxis without any cellular toxicity was given higher priority. The anti-invasive potential of NSC305787 and NSC668394 were further evaluated by using electric cell impedance sensing (ECIS) on a Roche xCELLigence system. This technique involves monitoring cell-cell interactions in real-time by measuring changes in cell resistance as a monolayer of human umbilical vein endothelial cells (HUVEC) is disrupted by invading tumor cells. Both NSC305787 and NSC668394 inhibited invasion of metastatic K7M2 cells on HUVEC monolayer (FIG. 3b,c). NSC305787 did not have any effect on invasion of K12 cells at 1 µM and 10 µM concentrations, whereas NSC668394 inhibited invasion by K12 cells slightly at 10 µM and did not have any effect at 1 µM concentration (FIG. 3b,c). Both compounds were not toxic to K7M2, K12 and HUVEC cells at these concentrations (data not shown).

Figure 4E:
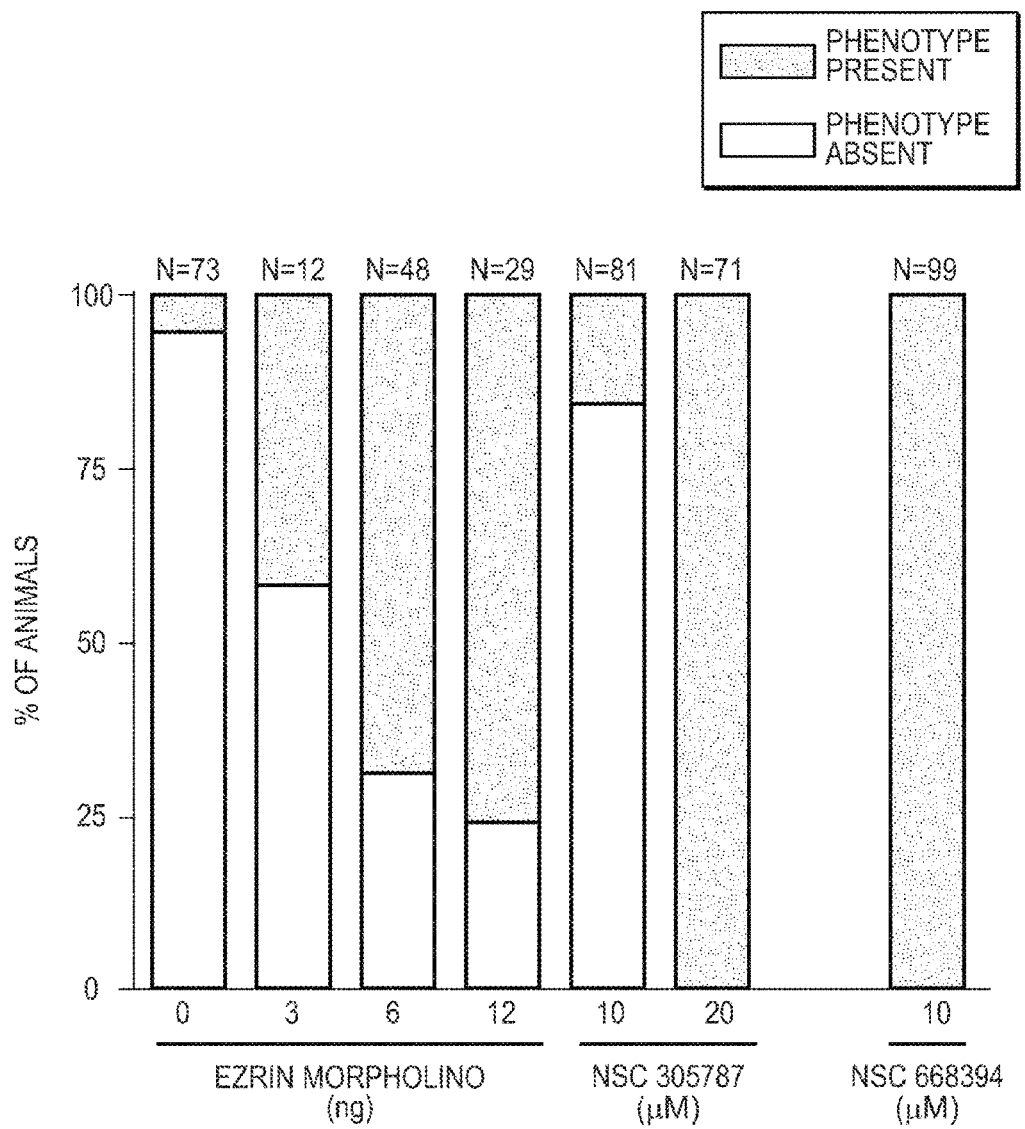
FIG. 4 illustrates NSC305787 and NSC668394 create reduced cell motility phenotypes in zebrafish. (A) Beginning in the late blastula period, blastodisc cells begin to spread over the yolk cell in the process of epiboly. Reduction of ezrin protein levels by antisense morpholino oligonucleotides (MO1) results in epiboly defects characterized by cells not spreading over the yolk cell but instead piling up at the animal pole. MO1 injected embryos were scored for epiboly defects at the 90% epiboly stage: WT (wild-type, not injected) 4/73 (5%); 3 ng MO1, 5/12 (42%); 6 ng MO1 33/48 (69%); 12 ng MO1 20/29 (69%). (B) When embryos were treated with 10 µM NSC305787, 12 of 81 embryos (15%) had epiboly defects that completely mimicked the MO1 injected embryos. At 20 µM NSC305787, 71 of 71 embryos (100%) had epiboly defects. (C) Normal eye development follows lateral movement of progenitor cells to form two eyes in untreated (WT) embryos. Treatment with 10 μM NSC668394 inhibited motility of eye progenitor cells resulting in cycloptic embryos at 28 hours post fertilization (hpf) in 97 of the 99 embryos (98%). (D) NSC668394 treated embryos continued to grow and formed a single functional eye at 6 days post fertilization. (E) Percentile of animals with the observed phenotypes upon MO1, NSC305787 and NSC668394 treatment are given.

NSC305787 and NSC668394 Inhibit Cell Motility During Zebrafish Embryonic Development Inhibition of ezrin protein expression by morpholino oligonucleotides (MO) results in a unique phenotype in zebrafish embryos (Link, V., et *J. Cell Sci.*, 119, 2073-2083 (2006)). All 65 primary hit compounds were tested on early zebrafish embryo development. Small molecules that killed the embryos prior to 70% epiboly during gastrulation were eliminated based on toxicity. The ezrin MO phenotype, characterized by reduced epiboly movements resulting from defective germ layer morphogenesis, was confirmed by microinjection of MO1 as described by Link et al. (FIG. 4a,e). Treatment with 10 µM NSC305787 mimicked the ezrin MO1 phenotype (FIG. 4b,e). Embryos treated with 10 µM NSC668394 showed normal development at earlier stages, but had a very distinctive cycloptic eye phenotype by 28 hpf (FIG. 4c,e). If NSC668394 was removed before 48 hpf, the animals survived up to 7 days, they were able to swim, and the cycloptic eye appeared to be otherwise functional as the single eye moved and responded to light (FIG. 4d). In normal zebrafish development, the eye field extends across the midline and as progenitor cells divide, they move laterally to form two separate eyes. Therefore, the observed cycloptic phenotype suggests stalling of eye precursor cells in the midline. Since inhibition of hedgehog pathway in sheep embryogenesis creates cycloptic lambs, we tested NSC668394 on Gli reporter assays in mammalian cell lines, but did not observe any significant inhibition (data not shown).

Prevention of Metastastatic Growth in a Lung Organ Culture Assay

In OS, the predominant site of recurrence and main cause of death is pulmonary metastasis (Dunn, D. & Dehner, L. P., *Cancer*, 40, 3054-3064 (1977)). An ex vivo mouse lung organ culture assay was performed to evaluate the inhibitory potential of the lead compounds. In this method, tumor cells reaching the lung following tail vein injection grew in the lung slices kept in organ culture, resembling in vivo lung metastasis (Ren, L., et al., *Oncogene*, 28, 792-802 (2009)).

Figure 5A:
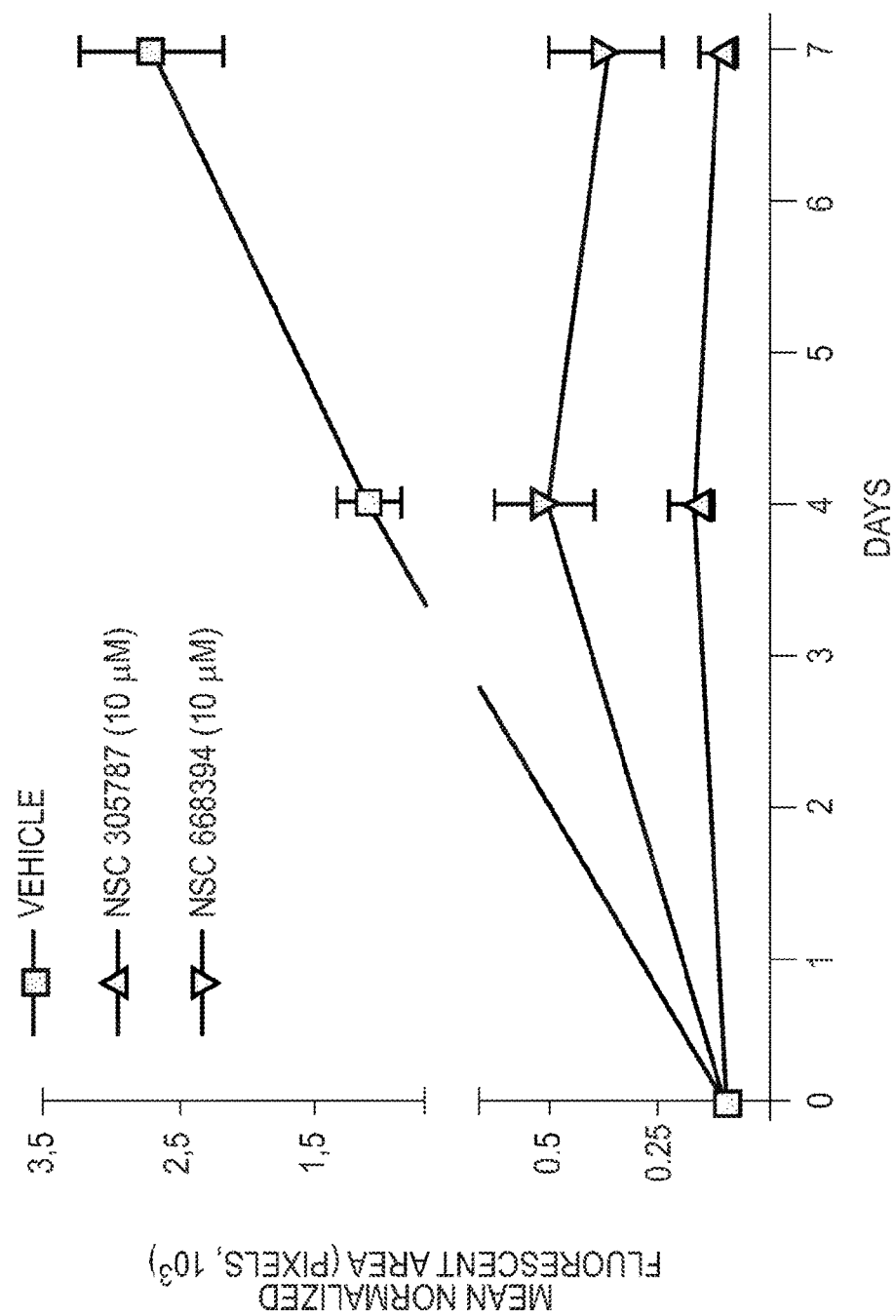
FIG. 5 illustrates NSC305787 and NSC668394 inhibit OS metastatic growth in lung organ culture. GFP expressing K7M2 OS cells ($2\times10^5$) were injected to tail vein of female BALB/c mice. Within 15 min of tumor cells injection, mice were euthanized and lungs were injected with a mixed agarose/medium solution and then were removed. Complete transverse sections (1-2 mm in thickness) were made from each lobe and 4-5 lung sections were placed on a single 1.5×0.7 cm sterile Gelfoam section. Lung sections were incubated at 37° C. in humidified conditions of 5% $CO_2$. Fresh medium or small molecules (10 μM) were replaced every other day. (A) Quantitation of the fluorescence signal from NSC305787 (10 μM) and NSC668394 (10 μM) treated organ cultures over time. Metastatic burden was quantified by measuring the fluorescent area of metastatic cells in each lung section at each time point and was expressed as mean fluorescent area (mean fluorescent area of each lung section over 4 lung sections). Mean fluorescent area was normalized to 100 pixels for day 0 to allow quantitative evaluation of metastatic progression over time. Data are represented as mean .s.d. from three independent experiments. (B) Fluorescence pictures of a representative culture treated with 10 μM NSC305787 and 10 μM NSC668394 are given on the right panel.
Figure 5B:
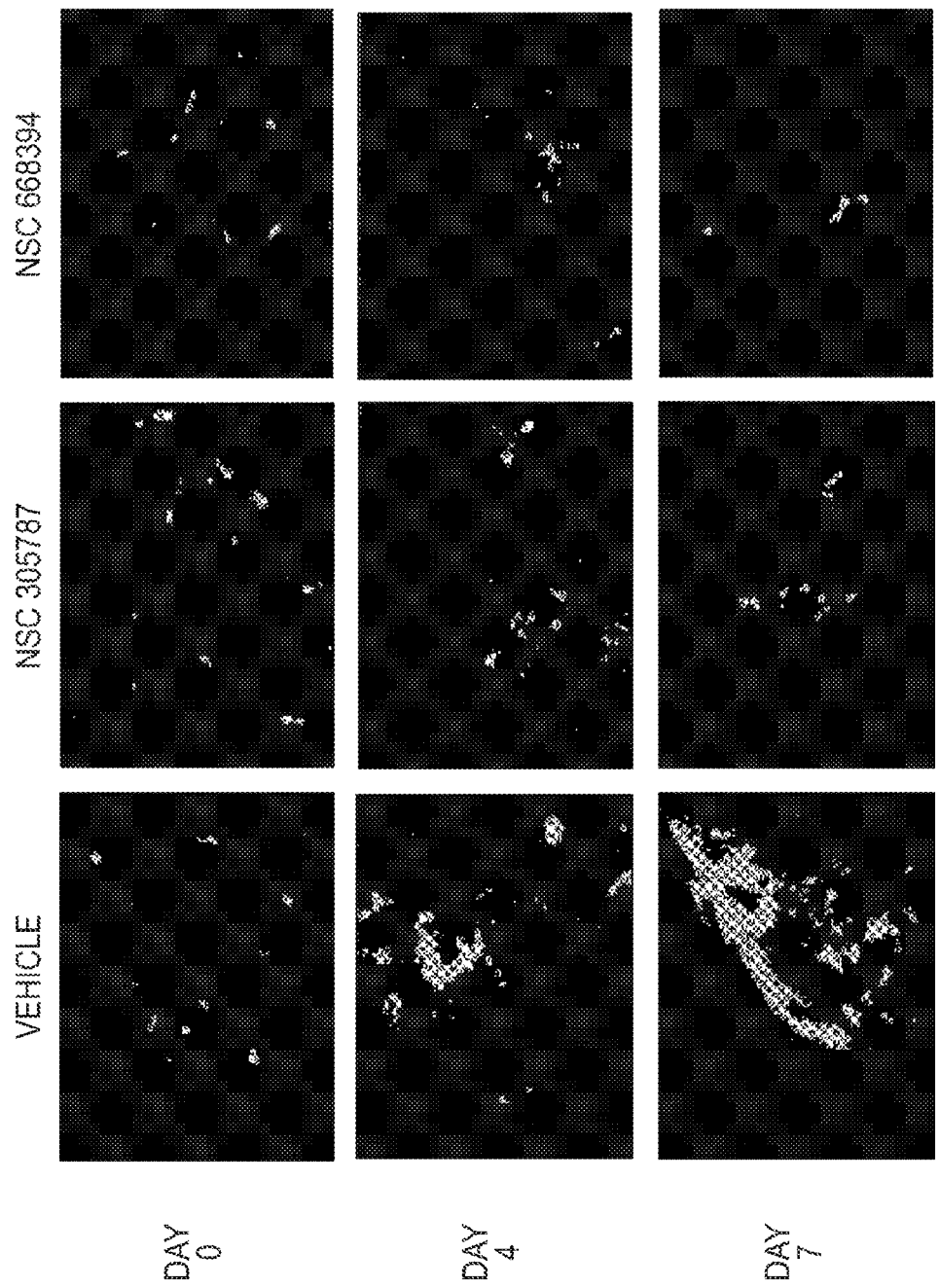

When green fluorescent protein (GFP) expressing metastatic K7M2 cells were injected through tail vein of mice, metastatic foci were followed up in the lung organ cultures, which was quantitated by GFP fluorescence. When mice were injected with less metastatic and low ezrin expressing K12 cells, no surviving tumor cells were observed in organ culture (data not shown). NSC305787 and NSC668394 treatment at 10 μM concentration significantly inhibited the lung metastasis of K7M2 high ezrin expressing OS cells in this organ culture assay (FIG. 5a,b).

NSC305787 and NSC668394 Inhibit Ezrin Dependent in vivo OS Metastasis Growth in Mouse Lung.

Figures 6A, 6B:
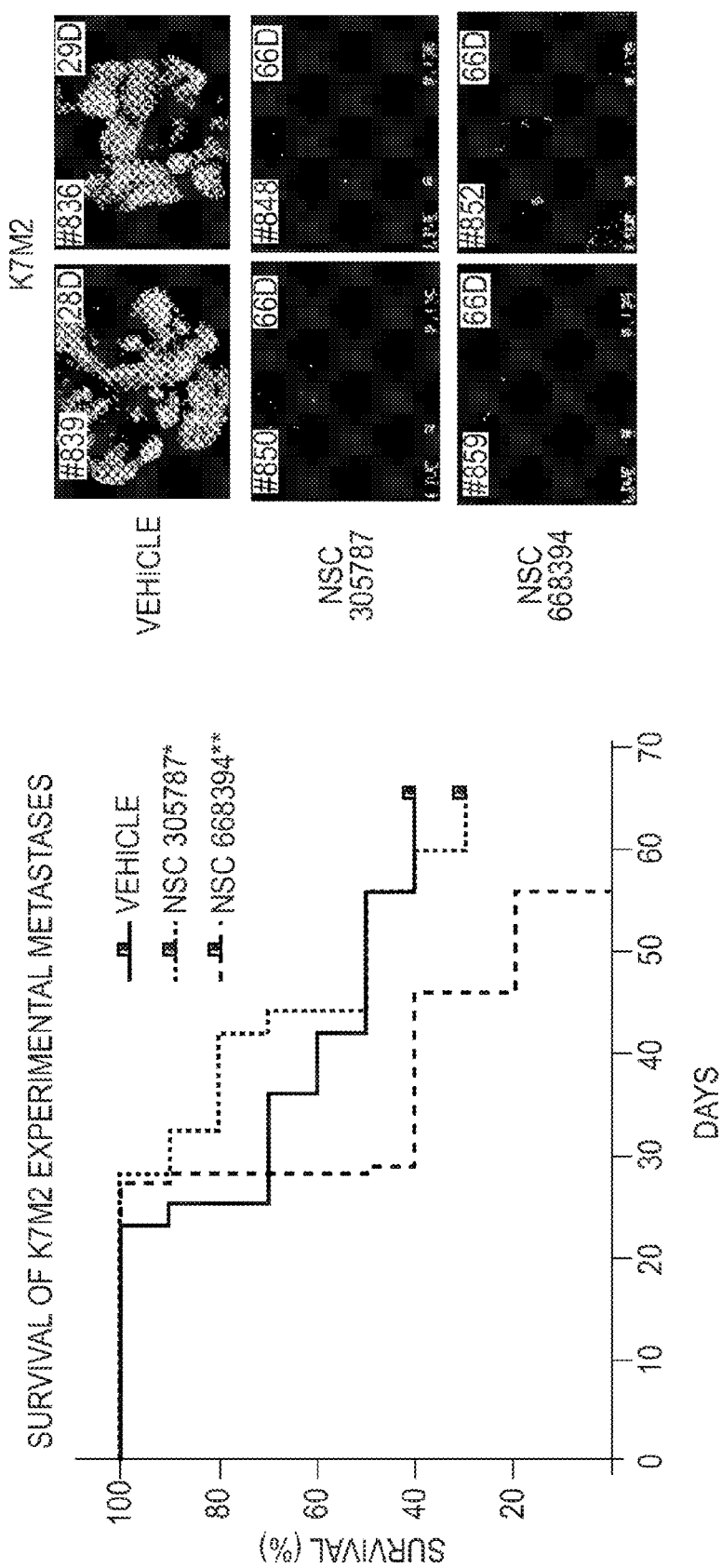
FIG. 6 illustrates NSC305787 and NSC668394 inhibit in vivo OS metastatic growth in lungs. (A) K7M2 metastatic OS tumor cells ($1\times10^6$) were injected via tail vein. Vehicle (1% DMSO), NSC305787 (240 μg/kg) and NSC668394 (226 μg/kg) were injected 5 days a week intraperitoneally. Kaplan-Meier survival curves show percent survival for NSC305787 and NSC668394 treatment over time. Median survival of vehicle, NSC305787 and NSC668394 treated K7M2 cells were 28.5, 50, and 49 days after tumor cell injection. Overall survival of NSC305787 treated mice is significantly different than the vehicle treated group (P value of NSC305787* is 0.0337 and NSC668394** is 0.0524). (B) Fluorescence pictures of whole lungs are given. There is a significant decrease in the number of the GFP expressing metastatic foci in the lung tissues of the NSC305787 and NSC668394 treated groups. (C) GFP expressing ezrin independent MNNG, human OS cells were injected to mice and treated with vehicle (1% DMSO), NSC305787 (240 μg/kg) and NSC668394 (226 μg/kg). Survival of each group is not different probably because MNNG is an ezrin independent cell line. Median survival of vehicle, NSC305787 and NSC668394 treated MNNG cells were 50.5, 49, and 48.5 days after tumor cell injection. (D) Fluorescent images of the lung tissues of this group are given. There is not a significant difference in the number of the GFP expressing metastatic foci in the lung tissues of the NSC305787 and NSC668394 treated groups.

After observing inhibition of lung metastatic growth in lung organ culture, the effects of NSC305787 and NSC668394 on in vivo lung metastasis model were tested. Following injection of GFP expressing K7M2 cells through tail vein, vehicle treated animals died due to progressive lung metastases in approximately 4 weeks (median survival 28.5 days). NSC305787 and NSC668394 treated animals survived up to 50 and 49 days, respectively (FIG. 6a). Overall survival of NSC305787 treated mice was significantly different than vehicle treated group (P=0.0337). NSC668394 treated group showed a very strong correlation (P=0.0524). When the lung tissues were harvested and analyzed, there was a significant difference between the vehicle treated and the small molecule treated groups (FIG. 6b).

Figures 6C, 6D:
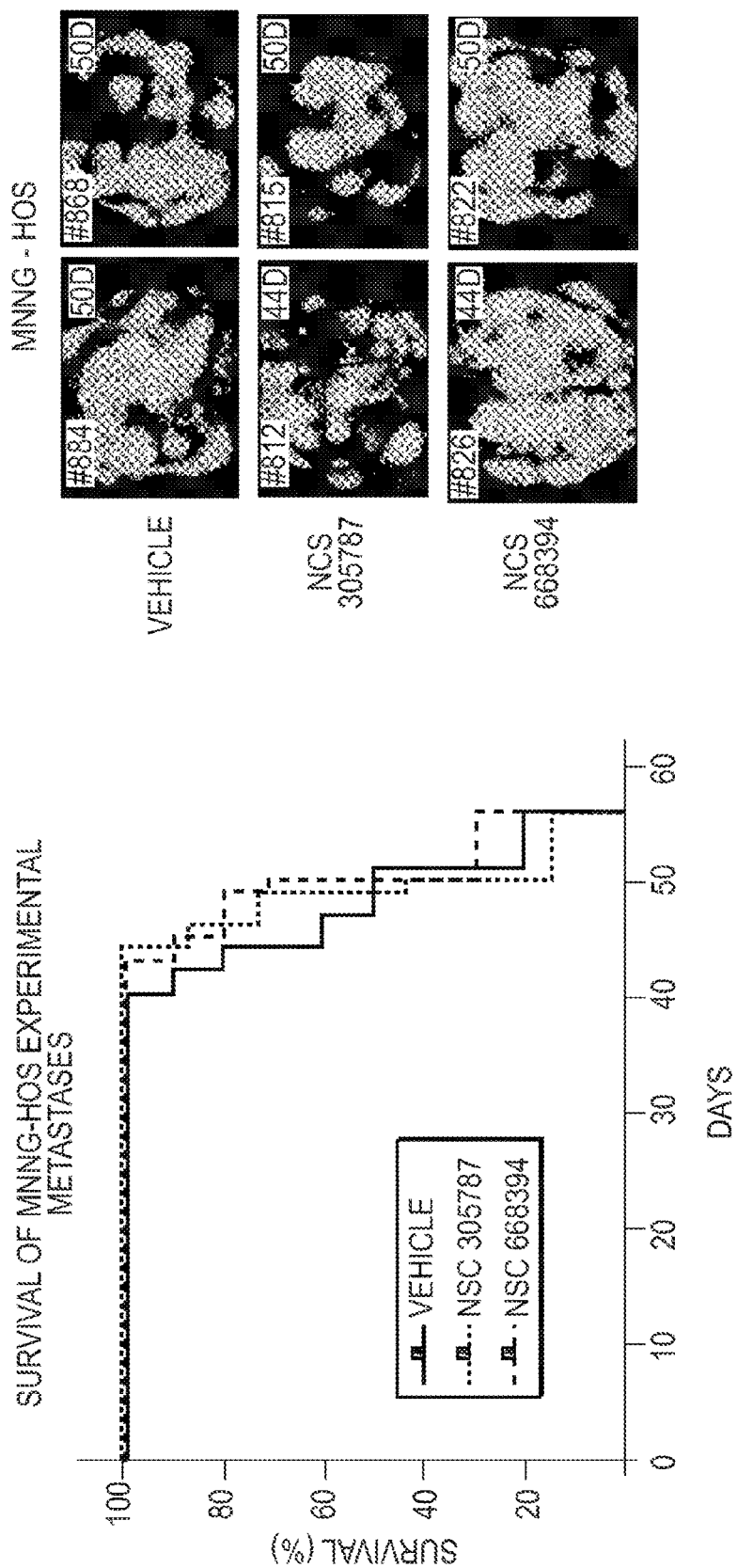
Figure 7:
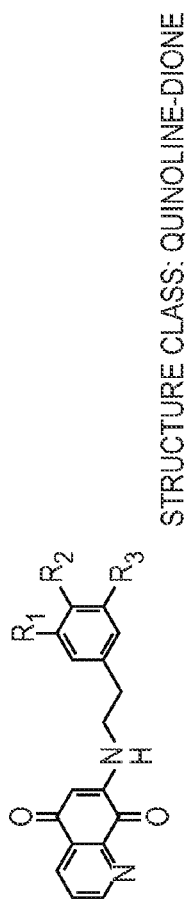
FIG. 7 provides results illustrating the functional activity of select compounds of the present invention on ezrin protein. The chemical structure of the embodied compounds is detailed and the corresponding binding and viability values are listed. The binding potential of select compounds to ezrin was analyzed by using SPR. Recombinant WT ezrin was immobilized onto a Biacore CM5 sensorchip and compounds were injected one-at-a-time at 6 different concentrations. SPR sensograms and $K_D$ values were determined using Biacore software. An average affinity for compounds binding to ezrin from 3 independent experiments was calculated. The embodied compounds have comparable affinity to WT ezrin as NSC 668394. The viability and growth inhibition activity of select compounds were determined by treatment of high ezrin expressed K7M2 and low ezrin expressed K12 osteosarcoma cells with a dose range of the select compound for 24 hours. $IC_{50}$ values, which represents the concentration at which growth is inhibited for 50% of total cell number, was measured by WST-1 (ROCHE). The embodied compounds show parallel growth inhibition activity to that of NSC 668394.
Figure 7:
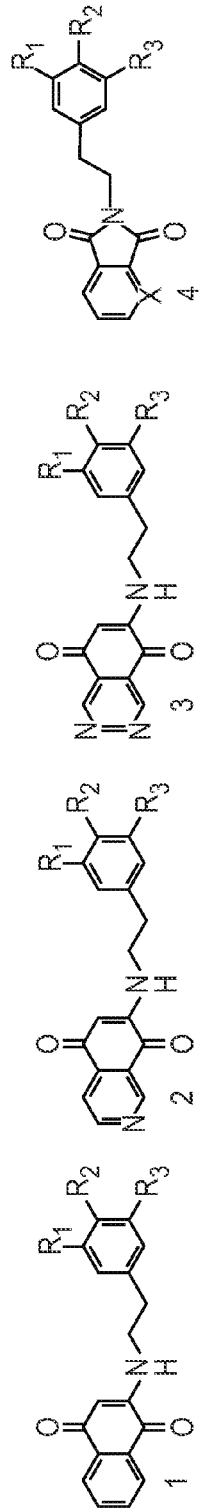
Figure 8:
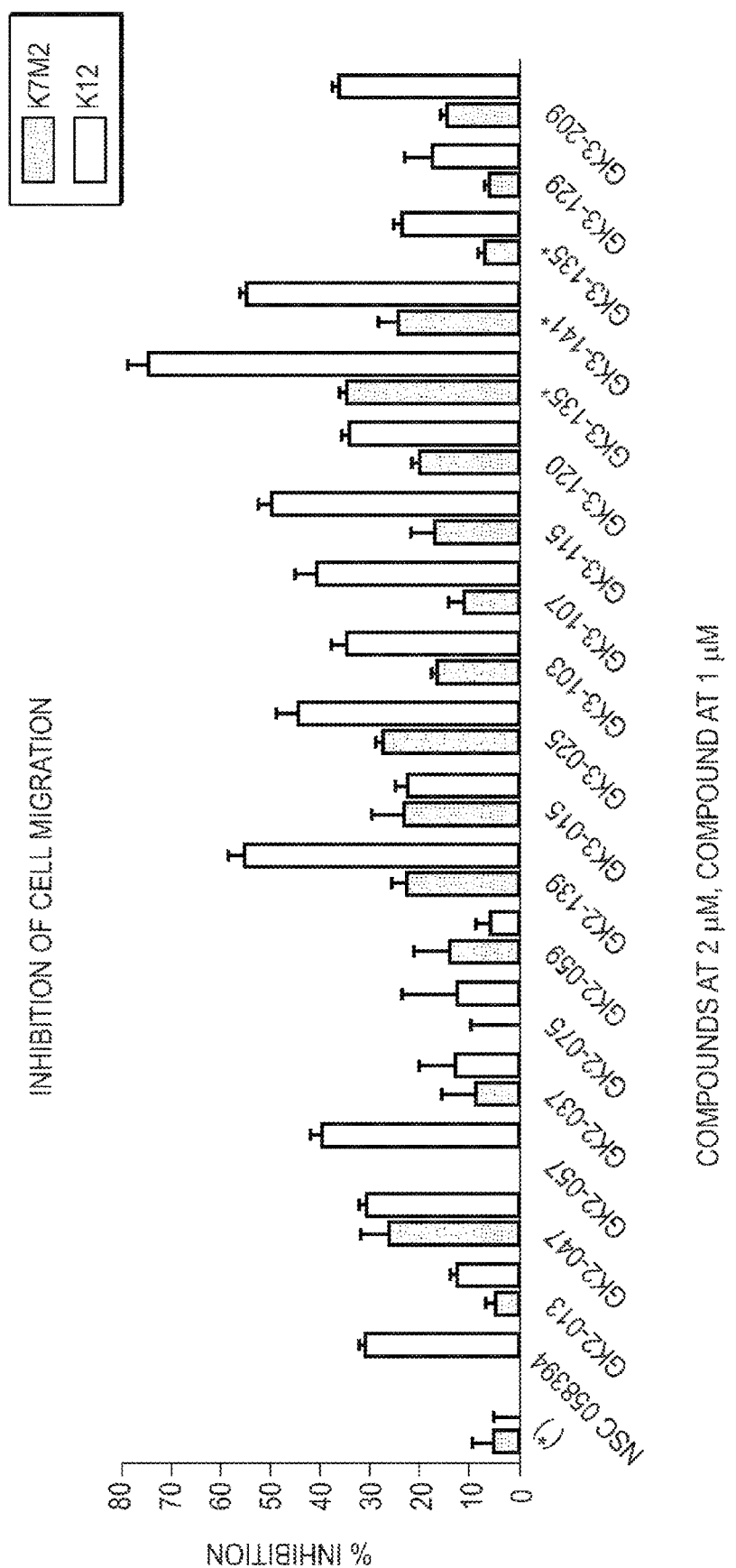
FIG. 8 illustrates that select compounds inhibit ezrin mediated migration. Anti-migration potential of the embodied compounds were validated using an electric cell migration system. High ezrin expressed K7M2 cells and low ezrin expressed K12 cells were treated with non-toxic concentrations of a compound and their corresponding anti-migration activity was measured. Data is represented as the ratio of compound K7M2 anti-migration activity divided by the K12 anti-migration activity. The X-axis details the non-toxic concentration of the compound used in the study. Embodied compounds GK2-057 has greater anti-migratory activity on the high ezrin expressed, metastatic osteosarcoma cells compared to NSC 668394, while benign to the K12 cell line.
Figure 9:
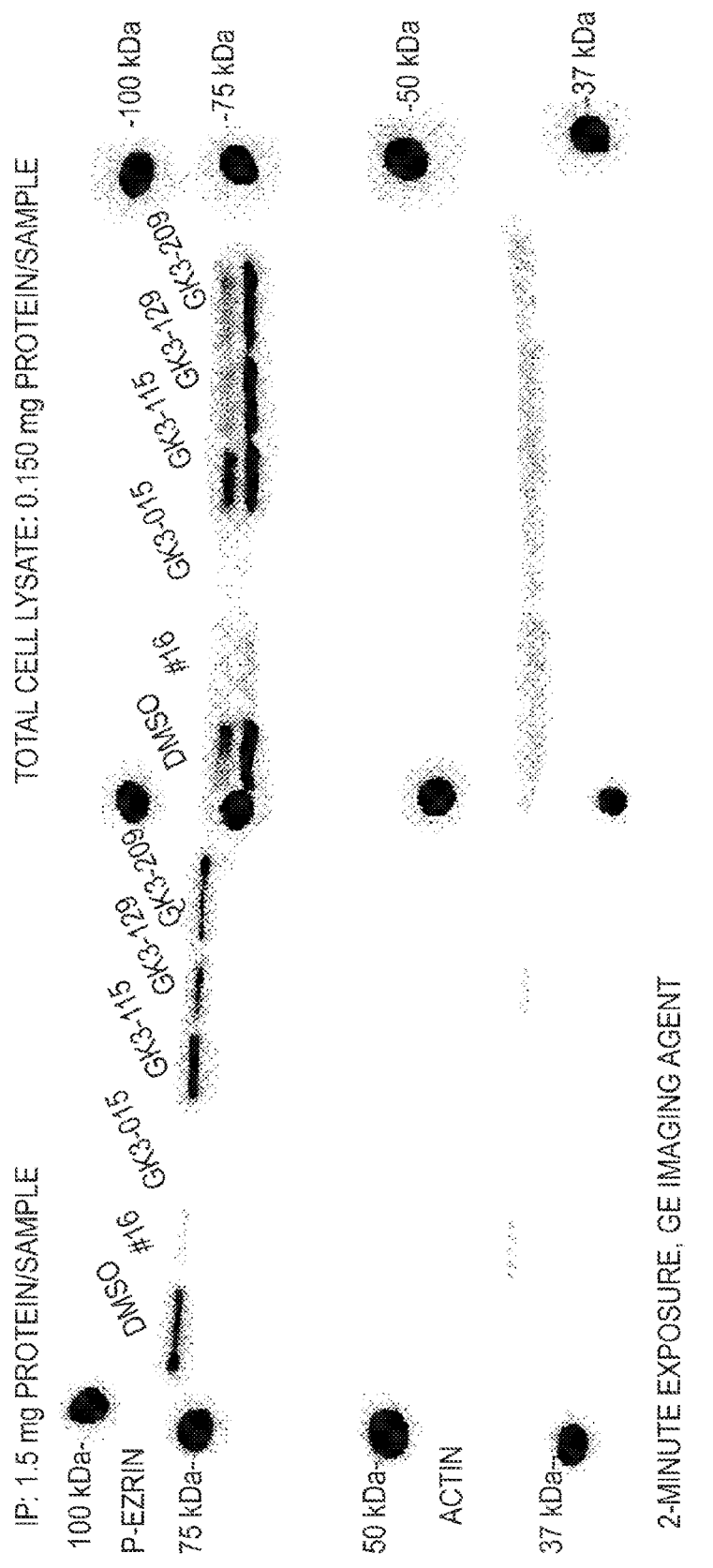
FIGS. 9 and 10 provide data showing compounds reduced T567 phosphorylation of ezrin and functional activity. K7M2 cells that were treated with embodied compounds and resolved protein lysates were immunoblotted for co-precipitated phosphorylated ezrin (TOP), or actin (BOTTOM). $4.0\times10^6$ K7M2 cells were plated in 15 cm dishes. After 24 h, the plates are at least 70% confluent. Media was removed and 10 μM of compound in SF DMEM was added. After the ezrin protein was incubated for 5 h with the indicated compound, the plates were lysed with PLB containing Calyculin A. 2 μL of Ezrin Ab and 10 μM of the compound (prepared in PLB) were added to the lysate and allowed to incubate overnight (14 h), followed by tumbling with Agarose IgG beads. The mixture was run on 10% acrylamide gel and transferred overnight.
Figure 10:
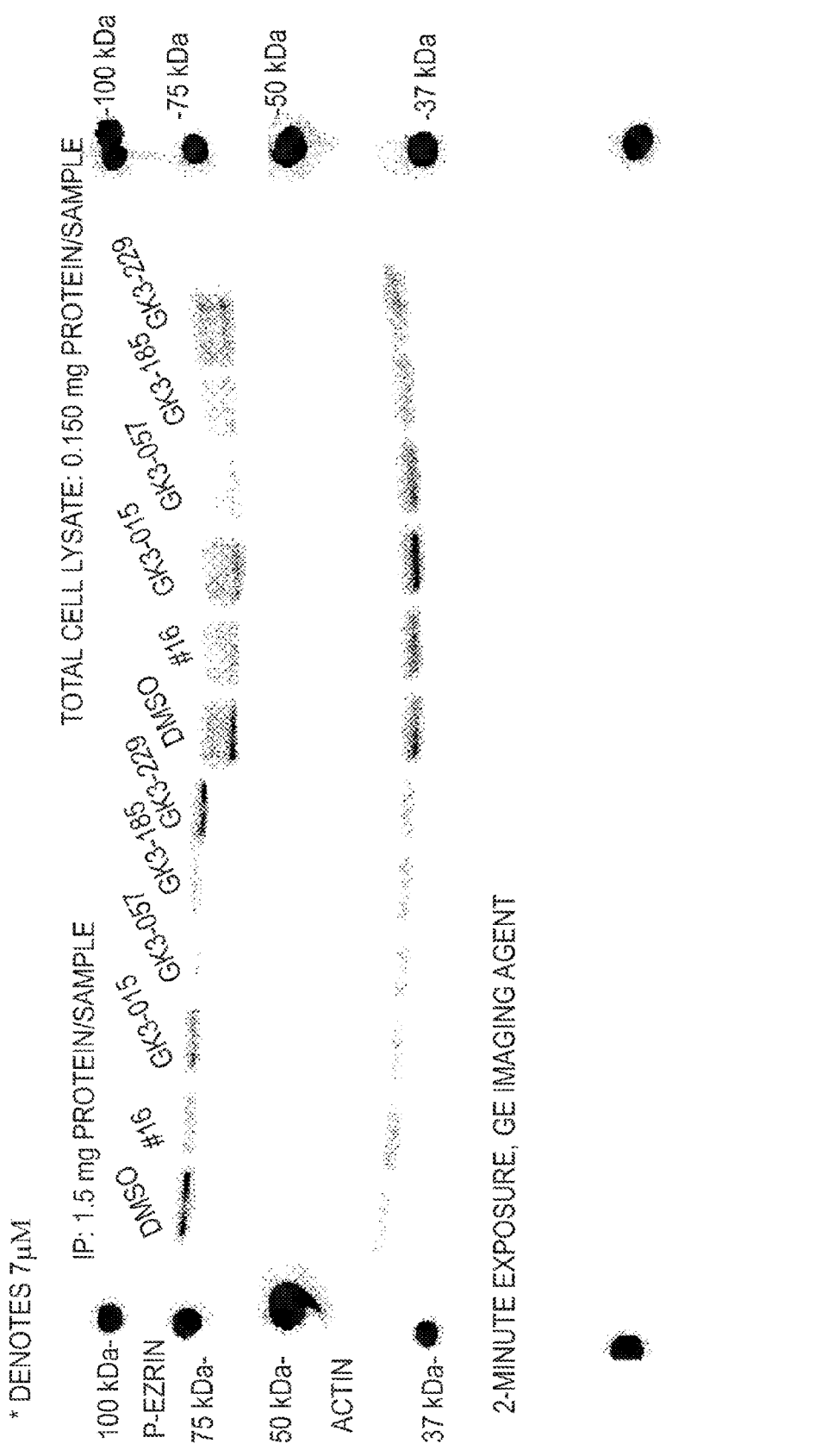

MNNG is a human OS cell line and maintains its metastatic phenotype even after inhibition of ezrin expression by siRNA (data not shown). MNNG cells were used as a negative control for ezrin-dependent specificity. Animals injected with GFP expressing MNNG cells by tail vein and treated with NSC305787 and NSC668394 did not demonstrate any difference in survival between control and treatment groups. Median survival of vehicle, NSC305787 and NSC668394 treated MNNG cells were 50.5, 49, and 48.5 days, respectively (FIG. 6c). We did not observe a difference between the vehicle, NSC305787 and NSC668394 treated groups for their number of GFP expressing metastatic foci in lung tissues (FIG. 6d).

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited, the entire disclosures of which are incorporated herein by reference.

What is claimed is:

1. A compound of

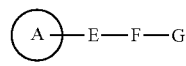

Formula I or pharmaceutically acceptable salts thereof, wherein
E, F and G are present;

is

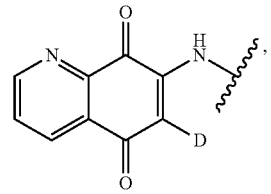

wherein
D is H, OH, $NO_2$, CN, carboxy, SH, $CF_3$, $C_1$ to $C_{10}$ alkoxy, $NH_2$, or $NR_{13}R_{14}$; wherein $R_{13}$ and $R_{14}$ are each independently H, $C_1$ to $C_{15}$ linear chain or branched chain alkyl;
E is —$(CH_2)_2$—;
F is a bond, O, S,

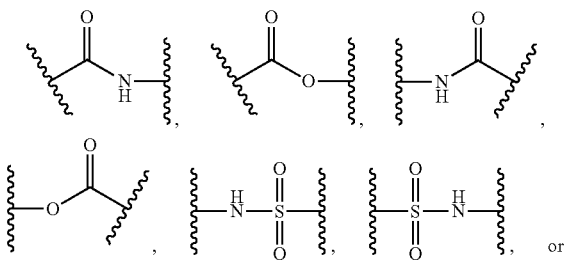

or

SEQUENCE LISTING

```
<160> NUMBER OF SEQ ID NOS: 1

<210> SEQ ID NO 1
<211> LENGTH: 22
<212> TYPE: DNA
<213> ORGANISM: Artificial Sequence
<220> FEATURE:
<223> OTHER INFORMATION: Translation blocking anti-ezrin morpholino
      oligonecleotide (MO)

<400> SEQUENCE: 1
cgcgaacatt tactggttta gg                                              22
```

-continued

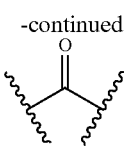

and
G is

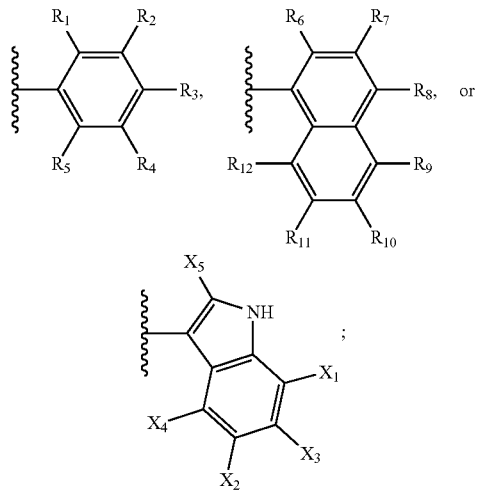

wherein
R₁ and R₅ are each indepdently H, halogen, $NO_2$, CN, carboxy, SH, $CF_3$, $C_1$ to $C_5$ alkoxy, $C_1$ to $C_5$ alkyl group, $NHCONH_2$, $NH-SO_2CH_3$, $NH-NH-NH_2$, $NH_2$, or $NR_{13}R_{14}$, and $R_3$, $R_6$-$R_{12}$ and $X_1$-$X_5$ are each independently selected from H, halogen, OH, $NO_2$, CN, carboxy, SH, $CF_3$, $C_1$ to $C_5$ alkoxy, $C_1$ to $C_5$ alkyl group, $NHCONH_2$, $NH-SO_2CH_3$, $NH-NH-NH_2$, $NH_2$, or $NR_{13}R_{14}$, and $R_2$ and $R_4$ are each independently selected from H, halogen, OH, $NO_2$, CN, carboxy, SH, $CF_3$, $C_1$ to $C_5$ alkyl group, $NHCONH_2$, $NH-SO_2CH_3$, $NH-NH-NH_2$, $NH_2$, or $NR_{13}R_{14}$;
with the proviso that when $R_3$ is OH and

is

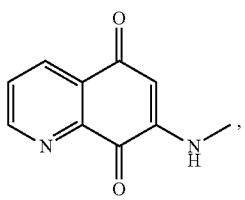

R₂ and R₄ are not both H, OH, or the same halogen.

2. The compound of claim 1, wherein D is hydrogen.
3. The compound of claim 1, wherein D is $NH_2$ or $NR_{13}R_{14}$.
4. The compound of claim 1, wherein
D is H, F is a bond; and
G is

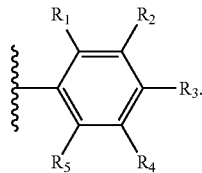

5. The compound of claim 1, wherein $R_3$ is hydroxy or methoxy.
6. A method of inhibiting ezrin protein in a cell comprising administering to the cell the compound of claim 1, or a pharmaceutically acceptable salt thereof.
7. A method of inhibiting the growth of a cancer cell comprising administering to the cell an amount of at least one compound of claim 1 wherein the cancer cell is an osteosarcoma cell or a lung cancer cell.
8. The method of claim 7 wherein the cancer cell is an osteosarcoma cell.
9. The method of claim 8, wherein the osteosarcoma cell is in a subject.
10. The compound of claim 1, wherein the compound is selected from the group consisting of GK2-013
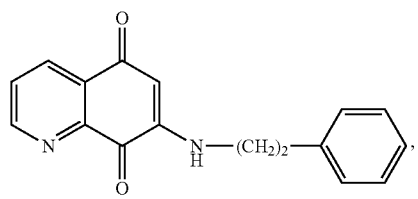

GK2-037
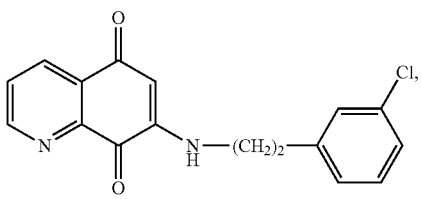

GK2-043
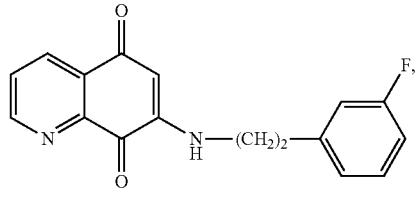

GK2-047
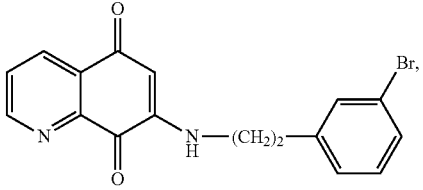

GK2-057
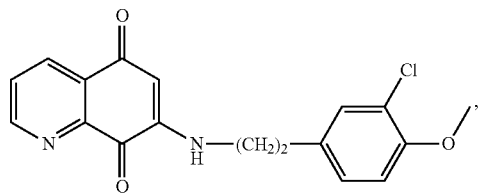
GK2-059
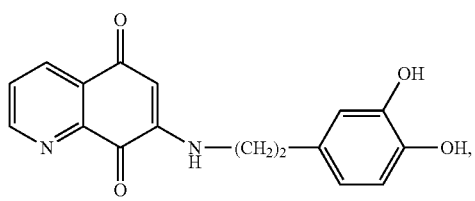
GK3-025
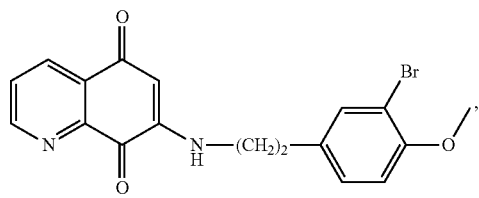
GK 2-085
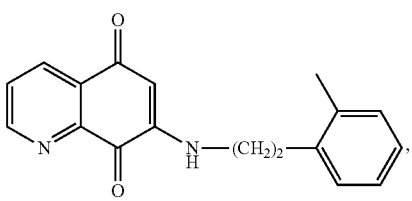
GK2087
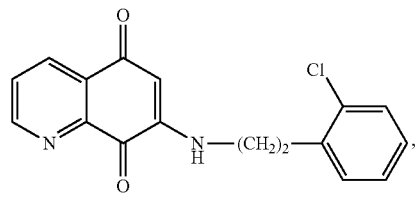
GK2-095
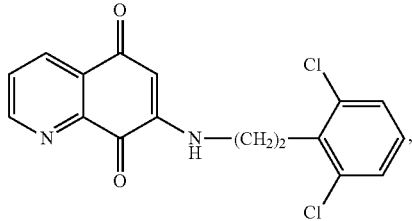
GK2-107
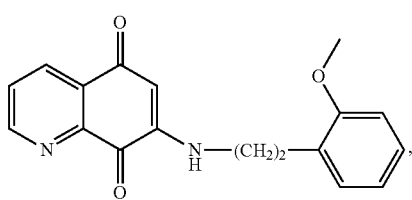
GK2-109
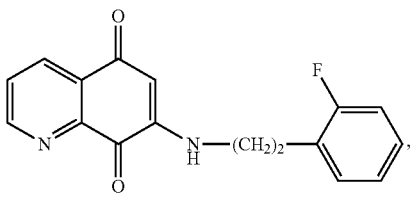
GK2-217
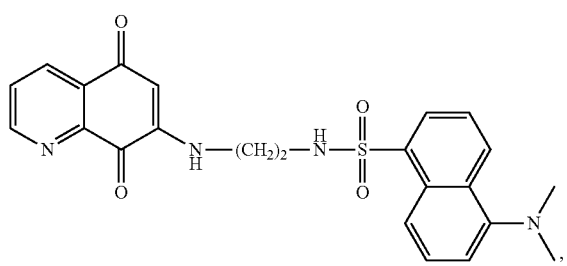
GK2-081
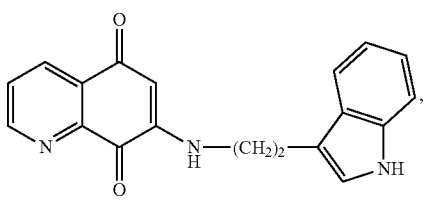
GK2-115
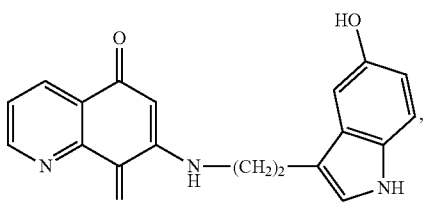
GK2-123
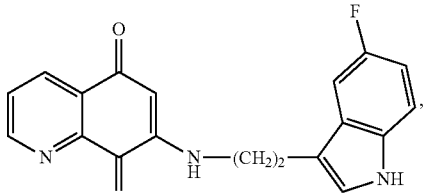
GK2-127
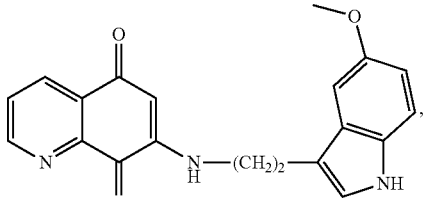
GK2-135
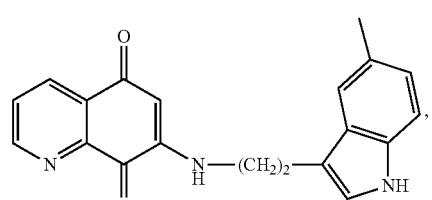
and GK3-209
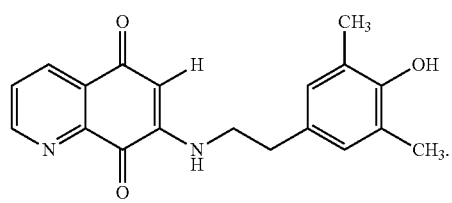
* * * * *

UNITED STATES PATENT AND TRADEMARK OFFICE
CERTIFICATE OF CORRECTION

| | | |
|---|---|---|
| PATENT NO. | : 9,522,908 B2 | Page 1 of 1 |
| APPLICATION NO. | : 14/047362 | |
| DATED | : December 20, 2016 | |
| INVENTOR(S) | : Milton L. Brown et al. | |

It is certified that error appears in the above-identified patent and that said Letters Patent is hereby corrected as shown below:

On the Title Page

Item (72) Inventors:
Delete "Gullay" and insert --Gulay--.

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*